United States Patent
Kawakami

(10) Patent No.: US 11,729,493 B2
(45) Date of Patent: Aug. 15, 2023

(54) IMAGE CAPTURE APPARATUS AND IMAGE CAPTURE METHOD

(71) Applicant: SONY GROUP CORPORATION, Tokyo (JP)

(72) Inventor: Hiro Kawakami, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 7 days.

(21) Appl. No.: 17/440,779

(22) PCT Filed: Feb. 10, 2020

(86) PCT No.: PCT/JP2020/005088
§ 371 (c)(1),
(2) Date: Sep. 19, 2021

(87) PCT Pub. No.: WO2020/195246
PCT Pub. Date: Oct. 1, 2020

(65) Prior Publication Data
US 2022/0182555 A1 Jun. 9, 2022

(30) Foreign Application Priority Data
Mar. 28, 2019 (JP) ................................. 2019-062937

(51) Int. Cl.
*H04N 23/63* (2023.01)
*G06T 7/13* (2017.01)

(52) U.S. Cl.
CPC ............ *H04N 23/633* (2023.01); *G06T 7/13* (2017.01)

(58) Field of Classification Search
CPC ......... H04N 5/232939; H04N 5/23212; H04N 2005/2255; H04N 23/633; H04N 23/67;
(Continued)

(56) References Cited

U.S. PATENT DOCUMENTS

| 4,680,639 A | 7/1987 | Isono et al. |
| 2015/0326797 A1* | 11/2015 | Ohyama ................ H04N 5/265 348/239 |

(Continued)

FOREIGN PATENT DOCUMENTS

| CA | 1244126 A | 11/1988 |
| CN | 104038699 A | 9/2014 |

(Continued)

OTHER PUBLICATIONS

International Search Report and Written Opinion of PCT Application No. PCT/JP2020/005088, dated Apr. 28, 2020, 09 pages of ISRWO.

(Continued)

*Primary Examiner* — Kelly L Jerabek
(74) *Attorney, Agent, or Firm* — Chip Law Group

(57) ABSTRACT

An image capture apparatus according to an embodiment of the present technology includes an image generation unit, an edge detection unit, and a color control unit. The image generation unit generates a captured image by capturing a subject. The edge detection unit detects an edge portion included in the generated captured image. The color control unit controls a color of a highlighted display for highlighting the edge portion for each detected edge portion based on color information about the edge portion in the captured image.

20 Claims, 19 Drawing Sheets

(58) Field of Classification Search
CPC ........ H04N 23/555; G06T 7/13; G03B 15/14; G03B 13/30; A61B 1/00009; A61B 1/00039
See application file for complete search history.

(56) References Cited

U.S. PATENT DOCUMENTS

| | | | | |
|---|---|---|---|---|
| 2016/0323500 | A1* | 11/2016 | Kamiya | H04N 5/142 |
| 2017/0019589 | A1* | 1/2017 | Moon | H04N 5/23293 |
| 2017/0104937 | A1* | 4/2017 | Yamada | H04N 5/23212 |
| 2018/0164542 | A1 | 6/2018 | Wakazono | |
| 2019/0014255 | A1 | 1/2019 | Zhao et al. | |

FOREIGN PATENT DOCUMENTS

| | | |
|---|---|---|
| EP | 0171764 A1 | 2/1986 |
| EP | 3148179 A1 | 3/2017 |
| JP | 06-145691 A | 3/1986 |
| JP | 06-028392 B2 | 4/1994 |
| JP | 10-51647 A | 2/1998 |
| JP | 2001-008065 A | 1/2001 |
| JP | 2007-028380 A | 2/2007 |
| JP | 2010-135865 A | 6/2010 |
| JP | 2012-109897 A | 6/2012 |
| JP | 2014-103450 A | 6/2014 |
| WO | 2015/196896 A1 | 12/2015 |
| WO | 2016/203692 A1 | 12/2016 |

OTHER PUBLICATIONS

Extended European Search Report of EP Application No. 20777693.1, dated Feb. 25, 2022, 08 pages.

* cited by examiner

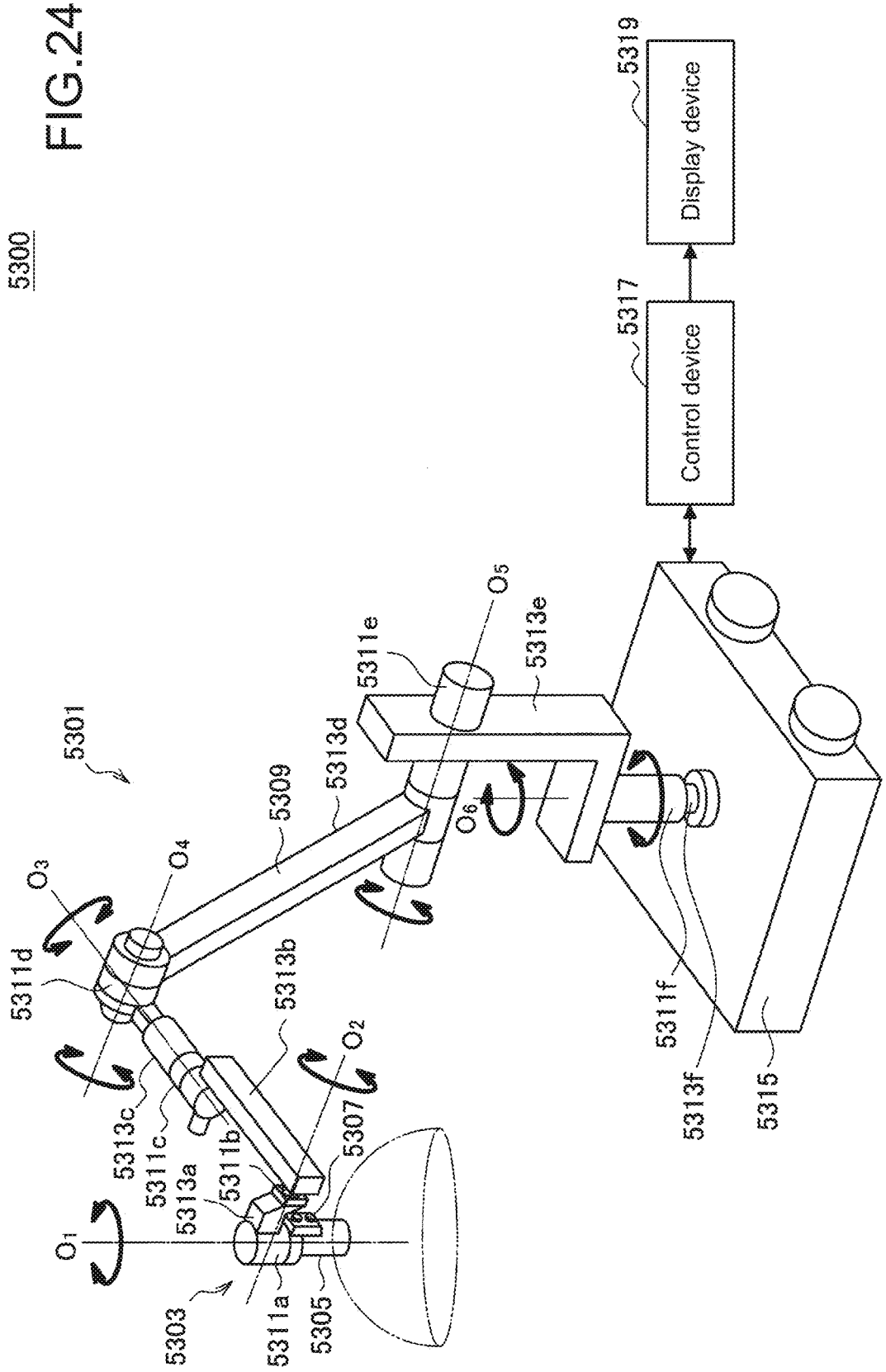

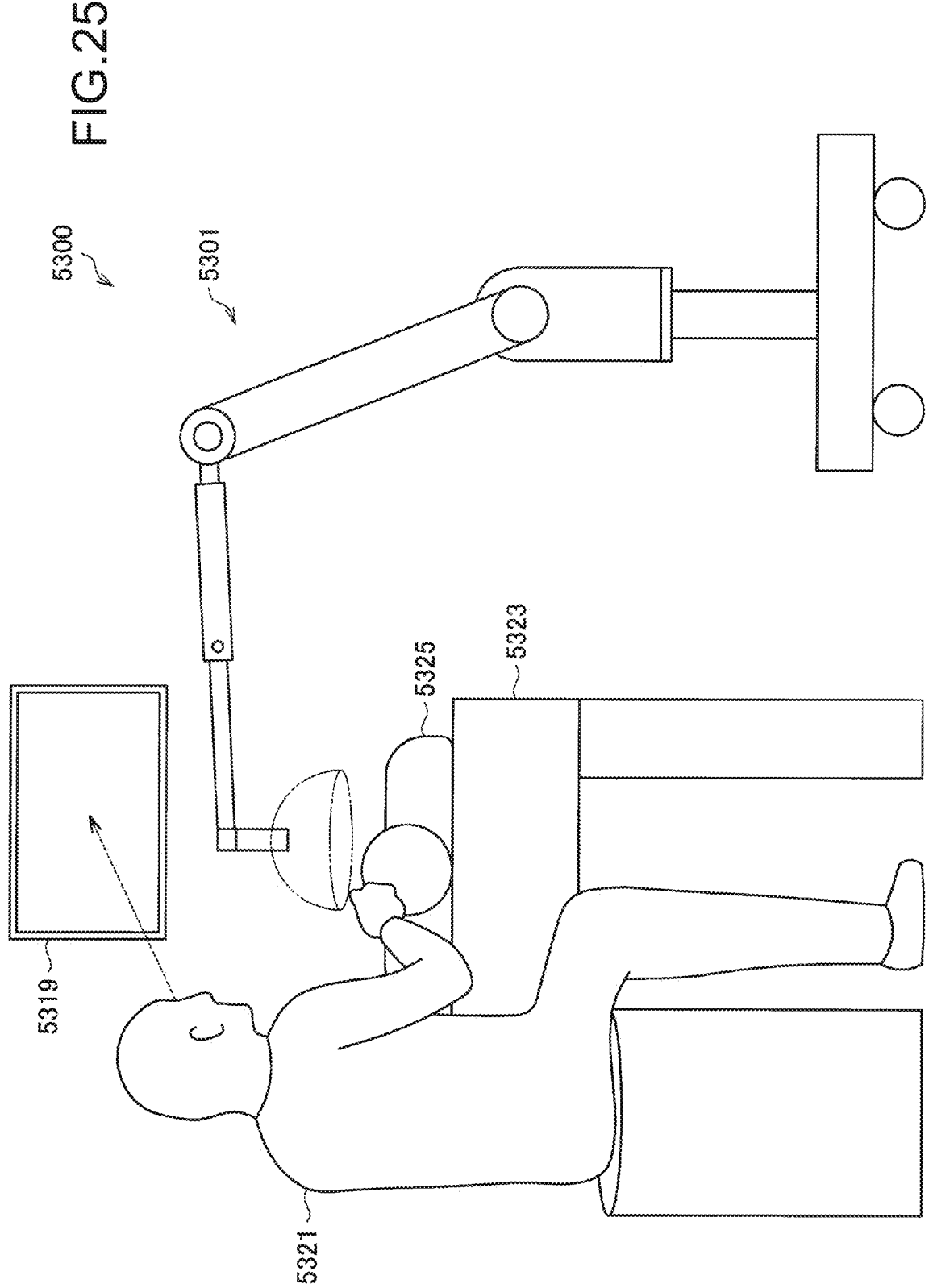

IMAGE CAPTURE APPARATUS AND IMAGE CAPTURE METHOD

CROSS REFERENCE TO RELATED APPLICATIONS

This application is a U.S. National Phase of International Patent Application No. PCT/JP2020/005088 filed on Feb. 10, 2020, which claims priority benefit of Japanese Patent Application No. JP 2019-062937 filed in the Japan Patent Office on Mar. 28, 2019. Each of the above-referenced applications is hereby incorporated herein by reference in its entirety.

TECHNICAL FIELD

The present technology relates to an image capturing apparatus, an image capture method, and a program for capturing an image of a subject.

BACKGROUND ART

Conventionally, a technique to assist a focus operation in capturing an image of a subject has been developed. For example, in a focused portion, the image becomes clear, and it is possible to detect a contour (edge) of the subject. An image or the like representing a focus state is generated using such a detection result.

Patent Literature 1 discloses a video signal processing apparatus for highlighting a contour portion of an image using a contour highlighting signal extracted from a video signal. In this video signal processing apparatus, the contour highlighting signal is generated in which the level becomes higher as it is closer to a just focus. For example, the contour highlighting signal is added to a color difference signal in accordance with its level. Therefore, when the focus is approached from an out-of-focus state to the just focus, the color of the contour becomes darker. This makes it possible to visually grasp a change in the focus state (paragraphs [0020] [0068] [0081], FIGS. 1 and 8 and the like of Patent Literature 1).

CITATION LIST

Patent Literature

Patent Literature 1: Japanese Patent Application Laid-open No. 2010-135865

DISCLOSURE OF INVENTION

Technical Problem

It is possible to perform a focus operation by visually highlighting and displaying edge portions in focus, and there has been a demand for a technique capable of smoothly improving visibility of such highlighted display.

In view of the above circumstances, an object of the present technology is to provide an image capture apparatus, an image capture method, and a program capable of improving visibility of highlighted display of edge portions.

Solution to Problem

In order to achieve the above object, an image capture apparatus according to an embodiment of the present technology includes an image generation unit, an edge detection unit, and a color control unit.

The image generation unit generates a captured image by capturing a subject.

The edge detection unit detects an edge portion included in the generated captured image.

The color control unit controls a color of a highlighted display for highlighting the edge portion for each detected edge portion based on color information about the edge portion in the captured image.

In this image capture apparatus, the captured image of the subject is generated, and the edge portion included in the captured image is detected. Furthermore, for each detected edge portion, the color of the highlighted display for highlighting the edge portion is controlled by using the color information about the edge portion in the captured image. This makes it possible to improve visibility of the highlighted display of the edge portion.

The color control unit may control the color of the highlighted display so that a color difference between an edge color represented by the color information about the edge portion and the color of the highlighted display becomes large.

The color control unit may control the color of the highlighted display so that the edge color and the color of the highlighted display are colors far in a hue plane or a brightness direction.

The color control unit may set the color of the highlighted display from a plurality of color candidates.

The plurality of color candidates may include chromatic color candidates. In this case, the color control unit may set a color candidate having a hue farthest from the hue of the edge color among the plurality of color candidates as the color of the highlighted display.

The plurality of color candidates may include a first color candidate and a second color candidate different in hue from the first color candidate.

The first and second color candidates may be set to be complementary to each other.

The plurality of color candidates may include achromatic color candidates. In this case, the color control unit may set a color candidate having brightness farthest from the brightness of the edge color among the plurality of color candidates as the color of the highlighted display.

The plurality of color candidates may include black and white. The color control unit may set the color of the highlighted display to the black color when the brightness of the edge color is larger than a predetermined threshold, and may set the color of the highlighted display to the white color when the brightness of the edge color is smaller than the predetermined threshold.

The plurality of color candidates may be set by a user.

The plurality of color candidates may be set according to the subject.

The edge detection unit may detect a pixel position of the edge portion. In this case, the color control unit may set the color of the highlighted display for each of the detected pixel positions.

The color information about the edge portion may include pixel information of a reference pixel included in a predetermined pixel region surrounding the pixel position of the edge portion.

The color control unit may calculate the hue of the edge color or the brightness of the edge color based on the pixel information of the reference pixel.

The color control unit may calculate an average hue of the reference pixel as the hue of the edge color.

The predetermined pixel region may be set according to the subject.

The color control unit may generate a peaking image in which the edge portion of the captured image is highlighted by the color of the highlighted display.

In the peaking image, a color of a portion different from the edge portion may be set to the same color as that of the captured image.

The color control unit may control the color of the highlighted display so that the display of the edge portion of the peaking image changes dynamically.

An image capture method according to an embodiment of the present technology is an image capture method executed by a computer system, and includes generating a captured image in which an image of a subject is captured.

An edge portion included in the generated captured image is detected.

A color of a highlighted display for highlighting the edge portion for each detected edge portion is controlled based on color information about the edge portion in the captured image.

A program according to an embodiment of the present technology causes a computer system to execute the following steps of:

generating a captured image in which an image of a subject is captured;

detecting an edge portion included in the generated captured image; and controlling a color of a highlighted display for highlighting the edge portion based on color information about the edge portion in the captured image.

BRIEF DESCRIPTION OF DRAWINGS

FIG. 24 is a diagram showing an example of a schematic configuration of a microscope surgery system.

FIG. 25 is a diagram showing surgery using a microscope surgery system shown in FIG. 24.

MODE(S) FOR CARRYING OUT THE INVENTION

Embodiments according to the present technology will be described below with reference to the drawings.

[Configuration of Image Capturing Apparatus]

Figure 1:
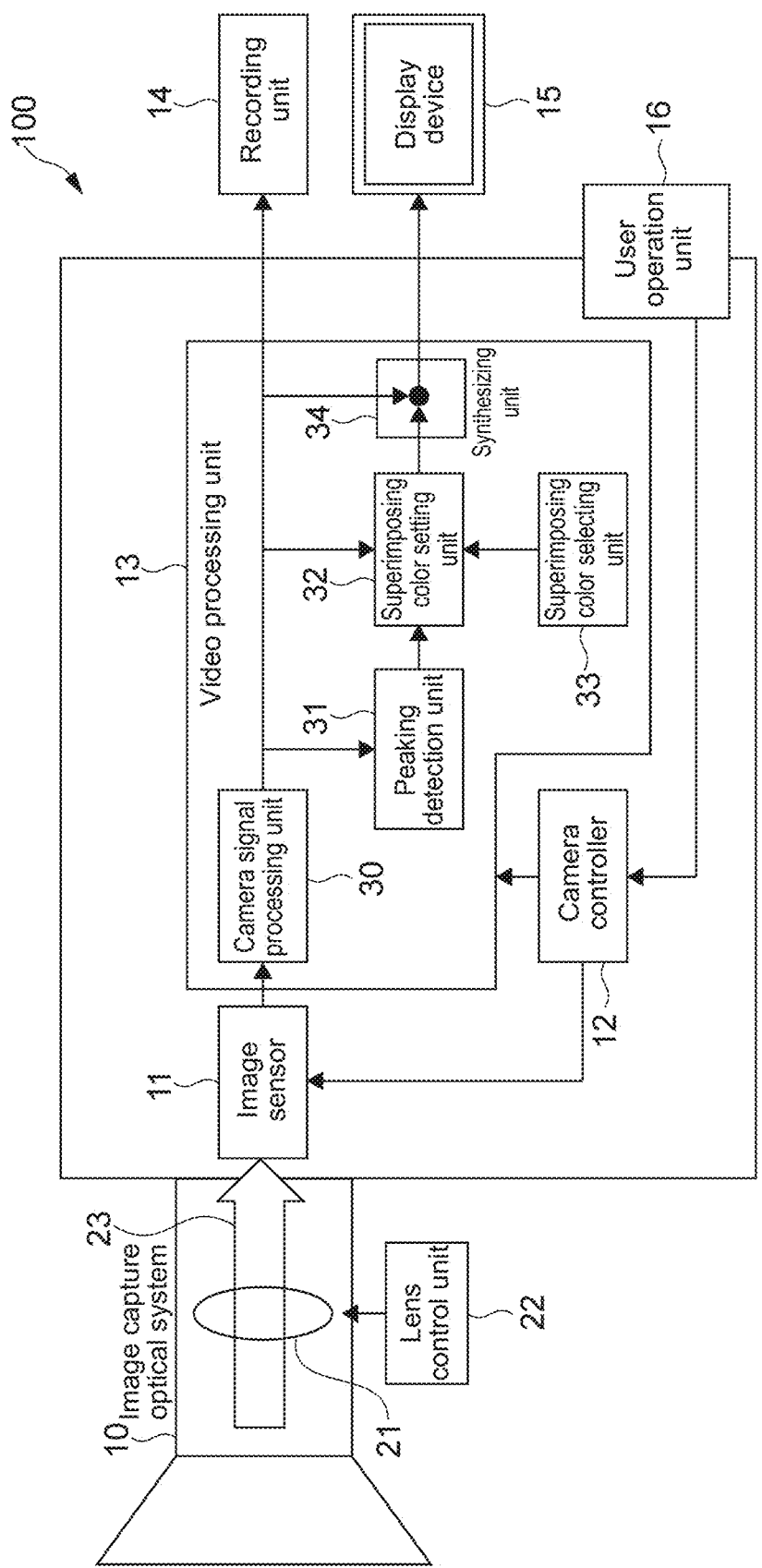
FIG. 1 is a schematic diagram showing a configuration example of an image capture apparatus according to an embodiment of the present technology.

FIG. 1 is a schematic diagram showing a configuration example of an image capture apparatus according to an embodiment of the present technology. An image capture apparatus 100 is a camera apparatus for capturing an image of a subject (camera system). The image capture apparatus 100 is configured as, for example, a video camera or a digital still camera.

The image capture apparatus 100 includes an image capture optical system 10, an image sensor 11, a camera controller 12, a video processing unit 13, a recording unit 14, a display device 15, and a user operation unit 16. Incidentally, the recording unit 14 and the display device 15 may be provided outside the image capture apparatus 100.

The image capture optical system 10 includes a lens unit 21 and a lens control unit 22. The lens unit 21 is, for example, an optical system including a plurality of lenses arranged in a lens barrel, and condenses light incident on the lens barrel on a light receiving surface of the image sensor 11 to be described later. A specific configuration of the lens unit 21 is not limited and a lens according to, for example, a type of the subject and an application of the image capture apparatus 100 may be appropriately used.

The lens control unit 22 is an operation mechanism for adjusting optical characteristics of the lens unit 21 (focus, magnification, aperture, etc.). The lens control unit 22 is configured to correspond to, for example, a manual focus. By operating the lens control unit 22, for example, the positions of the plurality of lenses are changed, and an operation of adjusting the focus (focus operation) becomes possible. A specific configuration of the lens control unit 22 is not limited and a mechanism or the like for adjusting, for example, the lens positions or the like by electronic control may be used.

The image sensor 11 is an image capture element for receiving light incident on the light receiving surface. The image sensor 11 is arranged with the light receiving surface toward the lens unit 21, and generates image data by receiving the subject light 23 passing through the lens unit 21. The image data is sequentially generated, for example, at a predetermined frame rate. As the image sensor 11, for example, the image capture element such as a CCD (Charge Coupled Device) sensor and a CMOS (Complementary Metal-Oxide Semiconductor) sensor is used.

The image data is data constituting a captured image by capturing an image of the subject. In the present disclosure, generating the image data constituting the captured image corresponds to generating the captured image. The image data includes pixel data for representing a plurality of pixels constituting the captured image. The pixel data is transmitted as, for example, a digital signal (pixel signal). Therefore, it can be said that the image data is generated as a set (image signal) of a plurality of pixel signals. In the present embodiment, the pixel data corresponds to pixel information.

Each pixel data includes RGB data indicating the intensity of red light, green light, and blue light included in the subject light 23, for example. Note that the RGB data can be uniquely converted into, for example, YCrCb data representing colors by brightness Y, a red color difference Cr, and a blue color difference Cb. In this manner, a configuration or the like may be used in which image data representing colors is generated by the brightness and the color difference. In addition, a format, a type, and the like of the image data are not limited.

The camera controller 12 is an arithmetic unit that controls an operation of each unit of the image capturing apparatus 100, and has a configuration necessary for a computer such as a CPU, a memory (RAM, ROM), or the like. The camera controller 12 controls operations of the image sensor 11 and the video processing unit 13 based on, for example, parameters input through the user operation unit 16 to be described later. In addition, an electronic control of the lens control unit 22, an operation control of the display device 15 or the like may be performed.

The video processing unit 13 is an arithmetic unit that performs various types of processing on image data (video data) generated by the image sensor 11 at the predetermined frame rate. The video processing unit 13 includes, for example, a register (memory) for recording settings for performing various types of arithmetic processing. By rewriting the register and implementing a predetermined program, desirable digital signal processing can be executed.

The video processing unit 13 is constituted by using an IC (Integrated Circuit) for video processing such as an imaging processor. Incidentally, the camera controller 12 may be configured on the imaging processor together with the video processor 13. For example, by installing and executing the program according to the present embodiment in the RAM of the camera controller 12 and the register of the video processing unit 13, the image capture method according to the present embodiment is executed by each unit of the image capture apparatus 100.

As shown in FIG. 1, the video processing unit 13 includes a camera signal processing unit 30, a peaking detection unit 31, a superimposing color setting unit 32, a superimposing color selecting unit 33, and a synthesizing unit 34. Each of these blocks is configured, for example, in the imaging processor. In addition, the blocks may be configured using dedicated devices such as a PLD (Programmable Logic Device) such as an FPGA (Field Programmable Gate Array) or an ASIC (Application Specific Integrated Circuit).

The camera signal processing unit 30 executes correction processing, conversion processing, and the like for the image data generated by the image sensor 11. That is, it can be said that the camera signal processing unit 30 generates the image data (captured image) to which various types of processing are applied.

In the camera signal processing unit 30, a correction processing, e.g., an image capture system correction such as brightness correction (shading correction), a gain correction of each pixel data (pixel signal), a gamma correction for corresponding to a monitor gamma, and a normalization correction (knee correction) for normalizing a signal level changed by each correction or the like, is executed. The correction processing is sequentially executed, for example, so that the captured image is appropriately generated. Alternatively, the camera signal processing unit 30 may perform the conversion processing or the like for converting the RGB data into YCrCb data or the like. In addition, the type, etc. of each processing on the image data is not limited.

Thus, the image capture apparatus 100 generates the captured image by capturing the image of the subject by the image sensor 11 and the camera signal processing unit 30. In the present embodiment, the image sensor 11 and the camera signal processing unit 30 function as an image generating unit.

The image data to which each processing is applied by the camera signal processing unit 30 is output to a main line of the image capture apparatus 100, for example, as data recorded in the recording unit, or as data used in broadcasting or the like. Furthermore, as shown in FIG. 1, in the image capture apparatus 100, based on the image data output by the camera signal processing unit 30, processing of other units of the video processing unit 13 is executed. Hereinafter, the image data output from the camera signal processing unit 30 will be referred to as original image data, and the image constituted of the captured image data will be referred to as an original image.

The peaking detection unit 31 detects a portion of the original image to be subjected to a peaking display. The peaking display is a highlighted display for coloring a focused portion in the image. Specifically, the peaking detection unit 31 detects the edge portion included in the original image (captured image) generated by the image sensor 11 and the cam era signal processing unit 30. In the present embodiment, the peaking detection unit 31 corresponds to an edge detection unit.

For example, for each pixel included in the original image, high-pass filter processing is performed to extract components in a high frequency band. More specifically, the original image data (pixel signal) is input to the high-pass filter, and edge detection data representing the position of the pixel including the high-frequency component is generated. A pixel including the high-frequency component is detected as the edge portion. Thus, the peaking detection unit detects a pixel position of the edge portion. Thus, it is possible to specify each position of the edge portion with high accuracy. Incidentally, the method of detecting the edge portion is not limited, and arbitrary edge detection processing may be used.

The superimposing color setting unit 32 controls, for each edge portion detected by the peaking detection unit 31, the color of the highlighted display for highlighting the edge portion based on color information about the edge portion in the original image. That is, the superimposing color setting unit 32 sets the color of the highlighted display of each edge portion (superimposing color with respect to original image)

in consideration of the original image. Hereinafter, the highlighting color may be referred to as a superimposing color.

The color information about the edge portion is information representing the color of the edge portion in the original image and the color around the edge portion. As the color information, information included in the pixel data of the original image is typically used. For example, information indicating an RGB intensity (RGB data, etc.) or information indicating brightness and a color difference (YCrCb data, etc.) of each pixel of the original image is the color information.

Setting of the superimposing color is performed for each edge portion. Therefore, each edge portion included in the original image is not necessarily highlighted by a single color, and the superimposing color may be different for each edge portion. This makes it possible to sufficiently highlight each edge portion regardless of, for example, the color of each edge portion in the original image.

In the present embodiment, the superimposing color is set for each pixel position detected as an edge portion. For example, the superimposing color is set for each pixel of the edge portion specified by the edge detection data, and edge enhancement data representing the superimposing color and the pixel position is generated. The edge enhancement data constitutes a superimposed image superimposed on the original image in the peaking display.

The superimposing color setting unit 32 sets a superimposing color (highlighting color) from a plurality of color candidates. That is, each edge portion is highlighted using any of the plurality of color candidates. As described above, by setting the plurality of color candidates in advance, the processing of setting the superimposing color is processing of selecting the color candidates. This makes it possible to easily set the superimposing color of each edge portion.

In the present embodiment, the plurality of color candidates is set by a user. For example, the plurality of color candidates is set by the user, and information of each color candidate is held by the superimposing color selecting unit 33 described below. Based on the color candidates set by the user, the superimposing color of each edge portion is set.

Each of the color candidates is set via the user operation unit 16. For example, a plurality of colors is displayed on the display device 15, and a candidate color is selected from among the colors. For example, another candidate color may be automatically set by selecting one of the basic colors by the user. In addition, a method of setting the plurality of candidate colors is not limited.

In this manner, since the user himself/herself can set the candidates of the superimposing colors, it is possible to easily visually recognize the highlighted edge portion. The method of setting the superimposing color (highlighting color) and the type of the candidate colors will be described in detail later.

The superimposing color selecting unit 33 accepts selection of the plurality of color candidates by the user. For example, information about the color candidates set by operating the user operation unit 16 by the user, which will be described later, is input to the superimposing color selection unit 33 via the camera controller 12. The superimposing color selecting unit 33 holds the input information of the color candidates and outputs it to the superimposing color setting unit 32, as appropriate. Note that a default candidate may be set as the plurality of color candidates and stored in the superimposing color selecting unit 33.

The synthesizing unit 34 synthesizes an image in which the superimposed image (edge enhancement data) generated by the superimposing color setting unit 32 is superimposed on the original image (original image data) generated by the camera signal processing unit 30. Therefore, the image synthesized by the synthesizing unit 34 is a peaking image in which a focused portion (edge portion) in the original image is displayed in a superimposing color. In this manner, the synthesizing unit generates the peaking image in which the edge portion of the original image is highlighted by the superimposing color.

For example, the image data in which the pixel data of the pixel corresponding to the edge portion of the original image data is replaced with the pixel data representing the superimposing color is generated as the peaking image. The method of synthesizing the original image and the superimposed image is not limited, and a circuit or the like capable of superimposing another display or the like on the image, for example, may be used, as appropriate.

As described above, the peaking image is an image in which the color of the edge portion is set to the superimposing color, and the color of the portion different from the edge portion is set to the same color as the original image. That is, the peaking display is limited to the edge portion, and a normal image (original image) is used as it is except for the edge portion. This allows the user to utilize the peaking display without discomfort.

The peaking image 40 generated by the synthesizing unit 34 is output to the display device 15. In the present embodiment, the superimposing color setting unit 32, the superimposing color selecting unit 33, and the synthesizing unit 34 function as the color control unit.

The recording unit 14 is a nonvolatile recording device. The recording unit 14 is connected to the main line of the image capture apparatus 100 and records the original image (original image data) output by the camera signal processing unit 30. As the recording unit 14, for example, a magnetic tape, an optical disk, a HDD (Hard Disk Drive), an SSD (Solid State Drive), and the like are used. The specific configuration of the record unit 14 is not limited.

The display device 15 is a display device for displaying the peaking image. As the display device 15, for example, a viewfinder (VF) of a video camera (image capture apparatus 100) is used. Furthermore, for example, an external display using a liquid crystal, an organic EL, or the like may be used as the display device 15. The external display may be a sub-display of an image capture apparatus 100 main body, or may be a display provided separately from the image capture apparatus 100.

For example, the user is a photographer (cameraman), and views the peaking image displayed on the display device 15 and operates the lens control unit 22 or the like, to thereby operating the focus of image capture apparatus 100. In the peaking image, the focused portion is highlighted by the superimposing color. This makes it possible for the user to photograph the subject while confirming the position where the focus is in the screen.

Note that it is conceivable that a resolution of the display device 15 is different from a resolution of the image sensor 11. For example, the image sensor 11 is 4K resolution (horizontal 3840 pixels, vertical 2160 pixels), and the display device 15 is an HD resolution (horizontal 1920 pixels, vertical 1080 pixels). Of course, the present technology is also applicable to the case where other configurations are used.

A resolution of a small display device 15 such as a viewfinder may be lower than that of the image sensor 11. In this case, for example, by the camera signal processing unit 30, the original image (original image data) or the like which is down-converted in accordance with the resolution of the display device 15 may be generated. Processing of the peaking detection unit 31, the superimposing color setting unit 32, and the synthesizing unit 34 is appropriately performed on the down-converted original image to generate the peaking image suitable for the resolution of the display device 15. Alternatively, the peaking image output from the synthesizing unit 34 may be down-converted.

The user operation unit 16 accepts a user operation on the image capture apparatus 100. For example, the color candidates of the above-described superimposing colors are set via the user operation unit 16. The user operation unit 16 includes, for example, various switches such as buttons and levers, a slider, a rotary knob, and the like. Furthermore, for example, the display device 15 functioning as a touch screen may be configured as the user operation unit 16. In addition, the specific configuration of the user operation unit 16 is not limited.

Basic Operation of Image Capture Apparatus

Figure 2:
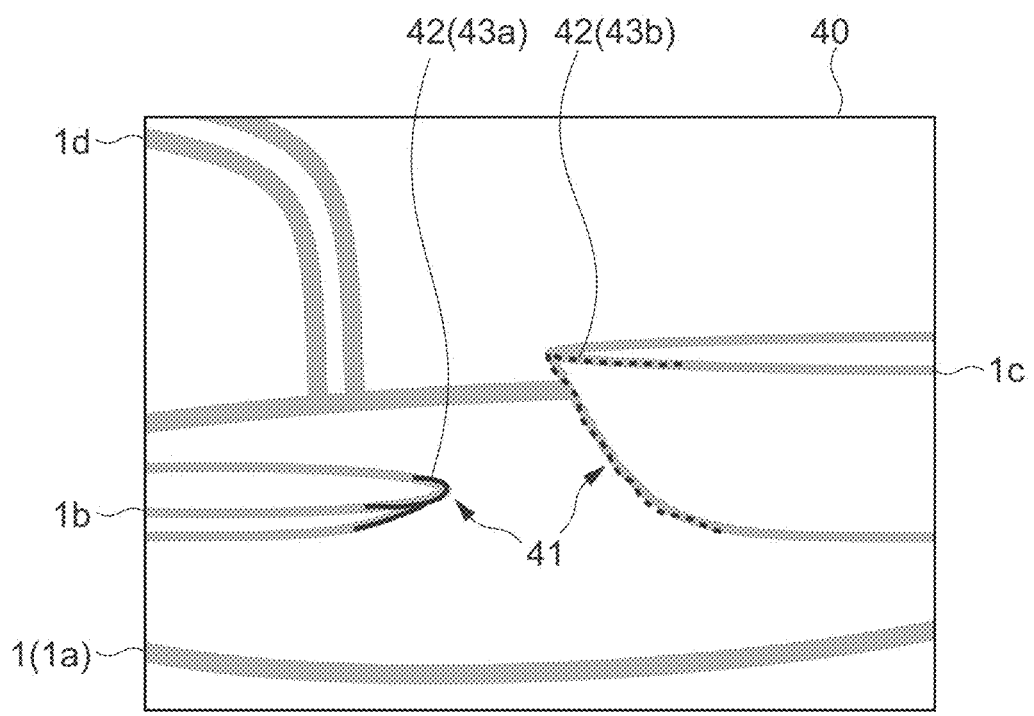
FIG. 2 is an example of a peaking image in which each edge portion of each subject is highlighted.

FIG. 2 is an example of the peaking image in which each edge portion of each subject is highlighted. Hereinafter, a basic operation of the image capture apparatus 100 will be described with reference to the peaking image 40 or the like shown in FIG. 2.

FIG. 2, as a subject 1, a table 1a, a left side dish 1b and a right side dish 1c arranged thereon, and a chair 1d placed in the back of the table 1a are schematically shown using gray lines. Among them, it is assumed that the image capturing apparatus 100 is focused on a part of the left dish 1b and a part of the right dish 1c.

Black lines in the figure represent highlighted displays 42 of edge portions 41. As shown in FIG. 2, the highlighted displays 42 are superimposed and displayed on a part of the subject 1 (edge portion 41). In the example shown in FIG. 2, two types of color candidates are used as the colors of the highlighted displays 42. In the following, the two types of color candidates are described as a first color candidate 43a and a second color candidate 43b. The highlighted displays 42 in which the first and second color candidates 43a and 43b are set to the superimposing colors are represented by a black solid line and a black dotted line. The peaking image 40 is typically a color image.

For example, light from the subject 1 (subject light 23) enters the image sensor 11 through the lens unit 21, and an image of the subject 1 is captured. The image data generated by the image sensor 11 is processed by the camera signal processing unit 30 and is recorded in the recording unit 14 as the original image data (original image). The original image data is displayed on the display device 15 as the peaking image 40 after being subjected to peaking display processing. Thus, the user can perform the operation of the lens control unit 22, while viewing the peaking image 40 displayed on the display device 15.

In the peaking display processing, the edge portion 41 of the original image is detected by the peaking detection unit 31. The edge portion 41 becomes a focus position is in focus. The superimposing color setting unit 32 sets the superimposing color of the edge portion 41 in consideration of the color of the original image. Specifically, the superimposing color is selected from the plurality of color candidates 43 (e.g., first and second color candidates 43a and 43b) set by the user and held in the superimposing color selecting unit 33 in accordance with the color in the original image.

The setting of the superimposing color is performed based on an edge color of the edge portion 41 in the original image. Here, the edge color is a color represented by the color information about the edge portion 41. For example, it is assumed that a certain pixel is detected as the edge portion 41. The color represented by the color information of the pixel serving as the edge portion 41, that is, the color of the pixel in the original image is used as the edge color. In this case, the edge color is the color of the edge portion 41 itself.

Furthermore, for example, a color represented by the color information including peripheral pixels around the edge portion 41 may be used as the edge color. For example, based on the color information of the pixels included in the periphery, an average of the colors of the respective pixels is calculated and used as the edge color. In this case, the edge color is an average color including peripheral portions of the edge portion.

In the image capturing apparatus 100, the superimposing color is set such that the edge color and the superimposing color are far from each other. In the present disclosure, the colors far from each other are, for example, colors far from each other in a hue plane or colors far in brightness from each other. It can also be said that the color difference is large in the colors far from each other. Therefore, the superimposing color is set to a color whose hue or brightness is not similar to that of the edge color (color having large difference). That is, the color candidate that does not resemble the edge color is selected as the superimposing color.

For example, in the peaking image 40 shown in FIG. 2, it is assumed that the first color candidate 43a is set to red and the second color candidate is set to light blue. At this time, it is assumed that the dish 1b on the left side is blue and the dish c on the right side is orange. In this case, the edge color of the edge portion 41 detected by the left dish 1b is a color having many blue components. The edge color of the edge portion 41 detected by the right dish 1c is a color having many red and yellow components.

For example, in the highlighted display 42 of the edge portion 41 of the left dish 1b, the first color candidate 43a (red) which is a color far from the color having many blue components is set as the superimposing color. On the other hand, in the highlighted display 42 of the edge portion 41 of the right dish 1c, the second color candidate 43b (light blue), which is a color far from the color having many red components, is set as the superimposing color.

For example, it is assumed that the first color candidate 43a is set to white and the second color candidate 43b is set to black. For example, if the edge portion 41 of the left dish 1b is a dark color, the first color candidate 43a having high brightness is set as the superimposing color. If the edge portion 41 of the right dish 1c has a bright color, the second color candidate 43b having low brightness is set as the superimposing color.

Note that the above description is merely an example, and the edge color of each edge portion 41 is not simply determined by the color or the brightness of the subject 1. In any case, the edge color is calculated using color information in the original image, and the color candidate apart from the edge color is appropriately selected.

As described above, in the present embodiment, the superimposing color is controlled such that the difference between the edge color represented by the color information about the edge portion 41 and the superimposing color becomes large. Thus, the highlighted display 42 in the peaking image 40 can be made sufficiently conspicuous, and the position of the edge portion 41 can be clearly represented. As a result, visibility of the highlighted display 42 is improved, and it is possible to sufficiently support a focus operation.

[Peaking Display by Colored Superimposing Color]

Hereinafter, a case in which a chromatic color having a hue is used as the superimposing color (plural color candidates 43) will be described.

Figure 3:
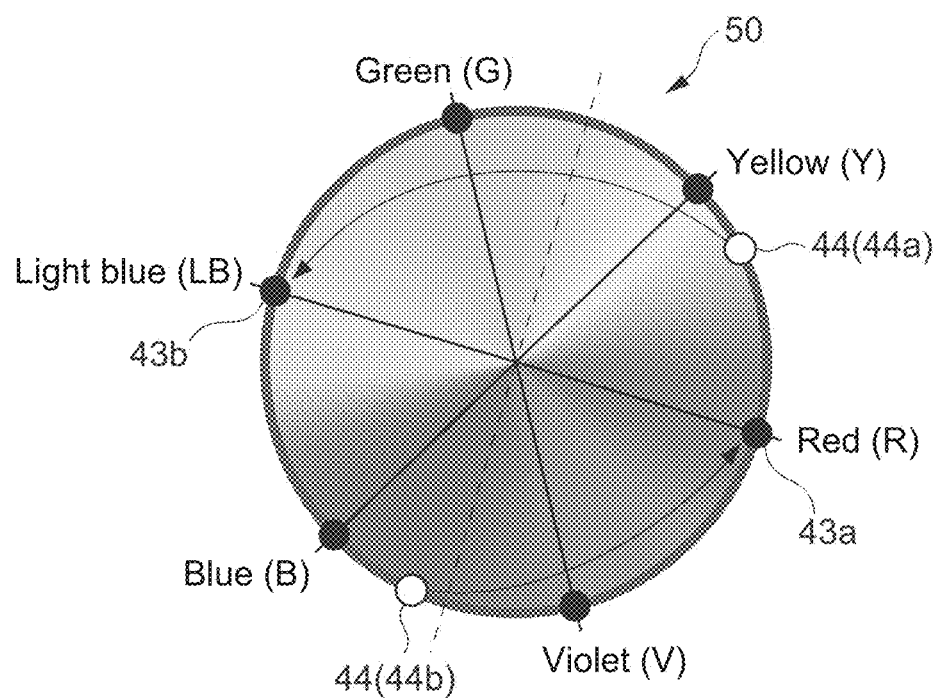
FIG. 3 is a schematic diagram for explaining a hue ring.

FIG. 3 is a schematic diagram for explaining a hue ring. The hue ring 50 is one in which hues are arranged in a circular shape. In FIG. 3, the hue ring 50 is schematically shown using a gray scale, but in reality, the hue ring 50 is represented by colors. The hue of each chromatic color can be calculated based on an RGB value, a color difference value, or the like.

FIG. 3 shows colors at respective positions (angles) of the hue ring 50. For example, in the hue ring 50, each of purple (V), blue (B), light blue (LB), green (G), and yellow (Y) is arranged at each position rotated by 60° in the clockwise direction with reference to red (R) (black circles in FIG. 3). Hereinafter, a plane formed by arranging the hues in the ring shape will be referred to as a hue plane.

For example, the color farthest from red R in the hue plane is light blue LB. The red R and the light blue LB are complementary colors arranged at diametrically opposite positions in the hue ring 50. Similarly, green G and purple V become complementary colors, and blue B and yellow Y become complementary colors.

In the present embodiment, it is possible to set a colored (chromatic color) superimposing color. In this case, the plurality of color candidates includes chromatic color candidates. The chromatic color candidates are set, for example, from the same hue ring 50 (colors in which brightness and intensity are set to be equal to each other). The plurality of color candidates are set to have different hues.

Hereinafter, a case in which two color candidates are mainly used will be described. In other words, the plurality of color candidates are set to include the first color candidate 43a and the second color candidate 43b having a different hue from the first color candidate 43a. In this case, the edge portion 41 is displayed using two colors in the peaking image 40. This makes it possible to realize a simple highlighted display with high visibility. In addition, by suppressing the number of colors of the highlighted display 42, the user can perform the focus operation by concentrating on only two colors, and excellent operability can be exhibited.

In this embodiment, the first and second color candidates 43a and 43b are set to be complementary colors to each other. That is, the first and second color candidates 43a and 43b are set to be hues rotated by 180° in the hue ring 50.

For example, two colors complementary to each other may be set by the user. Furthermore, for example, the color selected by the user may be set as the first color candidate 43a, and the second color candidate 43b serving as the complementary color may be automatically set. As a result, since the edge portions 41 (highlighted displays 42) are represented using colors having the furthest hues from each other (complementary colors), it is possible to make the edge portions 41 sufficiently conspicuous.

As will be described later, a color far from an edge color 44 in the hue plane is set as the superimposing color of the edge portion 41 among the two color candidates that are complementary to each other. That is, the superimposing color setting unit 32 controls the superimposing color such that the edge color 44 and the superimposing color are colors far in the hue plane. In FIG. 3, the hue of the edge color 44 is schematically shown by white circles.

For example, it is assumed that the first color candidate 43a is set to red R and the second color candidate 43b is set to light blue LB. For example, when the edge color 44a close to yellow Y between red R and yellow Y is calculated, the second color candidate 43b (light blue), which is a color far from the edge color 44a in the hue plane, is selected as the superimposing color. Furthermore, for example, when the edge color 44b close to blue B between blue B and violet V is calculated, the first color candidate 43a (red) which becomes a color far from the edge color 44b in the hue plane is selected as the superimposing color.

That is, in the hue ring, in the edge color 44 included in the range of ±90° from the first color candidate 43a, the second color candidate 43b is set to the superimposing color, and in the edge color 44 included in the range of ±90° from the second color candidate 43b, the first color candidate 43a is set to the superimposing color. As a result, since each edge portion 41 is displayed in the superimposing color far from the edge color 44, the visibility of the highlighted possible 42 of the edge portion 41 can be greatly improved regardless of the edge color 44 in the original image.

Note that the two color candidates 43 (first and second color candidates 43a and 43b) that are not in a complementary color relationship may be set. Even in this case, the color candidate 43 far from the edge color 44 in the hue ring 50 is set as the superimposing color. Thus, the user can perform the peeking display using any two colors, and it is possible to realize the highlighted display 42 with high degree of freedom.

It is also possible to set two or more color candidates 43. For example, three color candidates 43 may be set. In this case, for example, the three color candidates 43 are set to have an angle (120°) which is the farthest from each other in the hue ring 50. Similarly, it is possible to appropriately set four color candidates 43, five color candidates 43, and the like. Even if the two or more color candidates 43 are set as described above, the superimposing color is selected from the plurality of color candidates 43 such that the edge color 44 and the superimposing color are colors far in the hue plane. This makes it possible to sufficiently highlight the visibility of the highlighted display 42 regardless of the hue of the edge portion 41.

Figure 4:
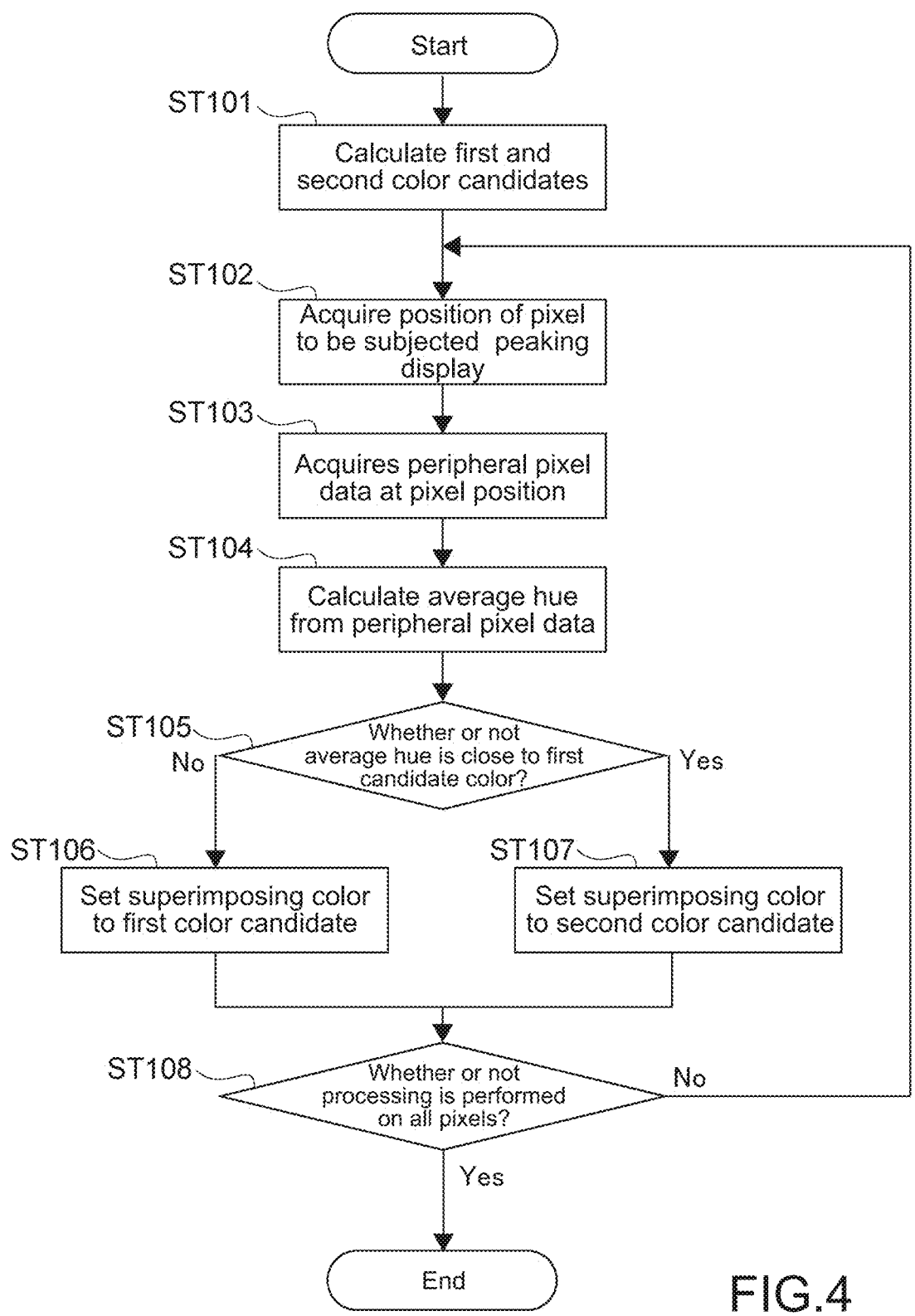
FIG. 4 is a flowchart showing an example of a peaking display using a colored superimposing color.
Figure 5:
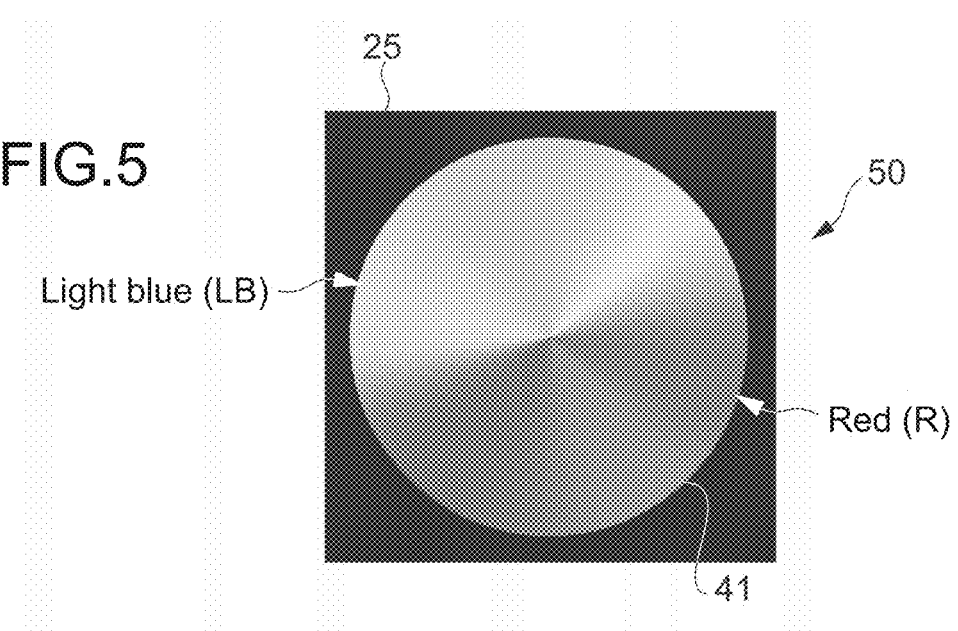
FIG. 5 is an image of the hue ring as an example of an original image.

FIG. 4 is a flowchart showing an example of the peaking display using the colored superimposing color. FIG. 5 is an image of the hue ring 50 as an example of the original image. Hereinafter, the peaking display processing using the colored superimposing color will be described with reference to FIG. 4 by taking an original image 25 shown in FIG. 5 as an example.

FIG. 5 shows a captured image (original image 25) by capturing the hue ring 50 as an example of the subject 1. The periphery (background) of hue ring 50 is black. The hue ring 50 shown in FIG. 5 has the same angular arrangement as the hue ring 50 described in FIG. 3. In the original image 25 shown in FIG. 5, the focus of the image capture apparatus 100 is focused on the entire hue ring 50.

The processing shown in FIG. 4 is, for example, processing performed on one original image 25. In the image capture apparatus 100, for example, each time the original image 25 is generated at the predetermined frame rate, the processing shown in FIG. 4 is executed, and the peaking display for each original image 25 is executed.

First, the hue components of the two color candidates 43 (first and second color candidates 43a and 43b) set by the user are calculated (Step 101). Each hue component is a hue value H representing the hue and can be represented by an angle in the hue ring 50, for example. For each of the color candidates 43a and 43b, the hue value H is calculated. The hue value H is calculated by, for example, the superimposing color selecting unit 33.

For example, when the color candidate is the RGB data, the hue value H is calculated based on each intensity of RGB. When the color candidate is color difference data, for example, the hue value H is calculated based on a red color difference Cr and a blue color difference Cb. In addition, the hue value H may be appropriately calculated in accordance with a format of the data of the color candidates.

Hereinafter, a case in which the first color candidate 43a is set to red R and the second color candidate 43b is set to light blue LB will be described. In this case, as the hue component of the first color candidate 43a, the angle at the hue ring corresponding to the position of red R is calculated as the hue value H. Furthermore, as the hue component of the second color candidate 43b, the angle at the hue ring 50 corresponding to the position of the light blue LB is calculated as the hue value H. Since the respective color candidates 43a and 43b are complementary colors, the hue values H of the color candidates 43a and 43b are shifted by 180° from each other.

When the hue value H is calculated, loop processing shown in Steps 102 to 108 is executed. The loop processing is performed sequentially for each pixel included in the original image 25, for example. Alternatively, for a plurality of pixels included in one column (horizontal line or vertical line), the processing may be performed in parallel.

The position of the pixel to be subjected the peaking display is acquired by the superimposing color setting unit 32 (Step 102). Specifically, based on a detection result of the edge portion 41 detected from the original image 25 by the peaking detection unit 31 (edge detection data), the pixel position of the pixel corresponding to the edge portion 41 is appropriately read.

Figure 6:
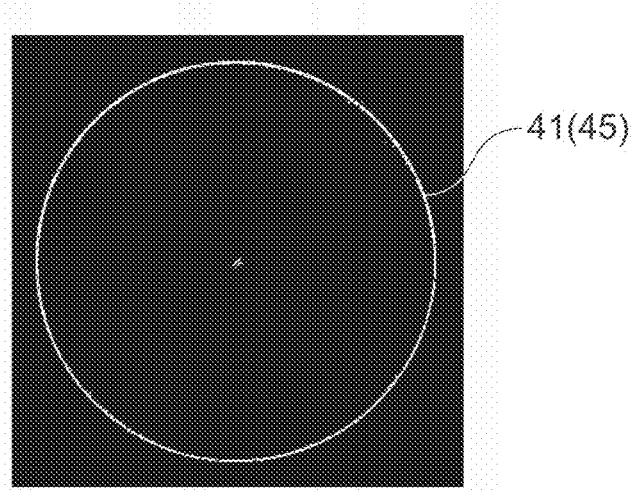
FIG. 6 is an image showing the edge portion detected from the original image shown in FIG. 5.

FIG. 6 is an image showing the edge portion 41 detected from the original image 25 shown in FIG. 5. In FIG. 6, a pixel (edge pixel 45) corresponding to the edge portion 41 of the original image 25 including the hue ring 50 is shown in white. In the original image 25 including the hue ring 50, an outer edge portion of the hue ring 50 is detected as the edge portion 41. Thus, as shown in FIG. 6, the edge pixel 45 of the hue ring 50 will be distributed in a circular shape. In the superimposing color setting unit 32, each pixel position of each edge pixel 45 is sequentially acquired.

The superimposing color setting unit 32 acquires peripheral pixel data around the pixel position (edge pixel 45) in Step 102 (Step 103). The peripheral pixel data is pixel data of the pixel included in a predetermined pixel region surrounding the edge pixel 45. In the following, the pixels included in the predetermined pixel region will be described as reference pixel.

Figure 7:
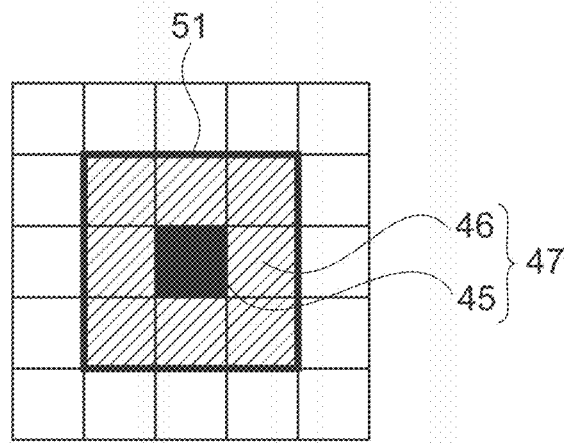
FIG. 7 is a schematic diagram showing an example of a pixel arrangement around an edge pixel.

FIG. 7 is a schematic diagram showing an example of a pixel arrangement around the edge pixel 45. A pixel arrangement shown in FIG. 7 is a pixel arrangement of the original image 25 around the edge pixel 45 at the center. Each pixel is represented by using a square arranged adjacent to the matrix in the vertical and horizontal directions. A black pixel is the edge pixel 45. The predetermined pixel region 51 is shown using a black thick line.

The predetermined pixel region 51 includes the edge pixel 45, and peripheral pixels 46 arranged around the edge pixel 45. The edge pixels 45 and the peripheral pixels 46 will be the reference pixel 47. In the example shown in FIG. 7, as the predetermined pixel region 51, a 3×3 pixel region centered on the edge pixel 45 is set. In this case, eight pixels arranged around the edge pixel 45 become the peripheral pixels 46.

The size, shape, position, and the like of the predetermined pixel region 51 are not limited. For example, a 5×5 or 7×7 pixel region centered on the edge pixel 45 may be set. Also, a 2×2 or 4×4 pixel region, and a 2×3 and 5×4 pixel region may be set. The edge pixel 45 may be deviated from the center of the pixel region. In addition, any region including the edge pixel 45 may be set as the predetermined pixel region 51.

For example, when the pixel position of the edge pixel 45 is read, the pixel positions of the other pixels (peripheral pixels 46) included in the predetermined pixel region 51 are calculated. Then, based on each pixel position, the pixel data of the reference pixel 47 (edge pixel 45 and peripheral pixels 46) from the original image 25 is read, respectively.

The pixel data of the reference pixel 47 includes information representing a color of each pixel in the predetermined pixel region 51. Therefore, the pixel data of the reference pixel 47 includes color information around the edge pixel 45 (edge portion 41). In a colored peaking display, the pixel data is used as the color information about the edge portion 41. Thus, the color information about the edge portion 41 includes the pixel data of the reference pixel 47 included in the predetermined pixel region 51 surrounding the pixel position of the edge portion 41. Furthermore, the color represented by the pixel data of the reference pixel 47 is the edge color 44.

The superimposing color setting unit 32 calculates an average hue from the peripheral pixel data (pixel data of reference pixel 47) (Step 104). That is, the average of the hue values of the predetermined pixel region 51 that is the periphery of the edge portion 41 is calculated.

Processing of calculating one hue value from the pixel data of the reference pixel 47 corresponds to processing of calculating the hue of the edge color 44 represented by the pixel data of the reference pixel 47. Thus, in the image capture apparatus 100, the superimposing color setting unit 32, calculates the hue of the edge color 44 based on the pixel data of the reference pixel 47. This makes it possible to set the superimposing color in accordance with a tendency of the hue around the edge portion, and to make the superimposing color sufficiently conspicuous.

As described above, in the present embodiment, the average hue of the reference pixel 47 is calculated as the hue of the edge color 44. For example, based on the pixel data read in Step 103, the hue values of the reference pixel 47 (edge pixel 45 and peripheral pixel 46) are calculated. The average hue is calculated by averaging these hue values.

Figure 8:
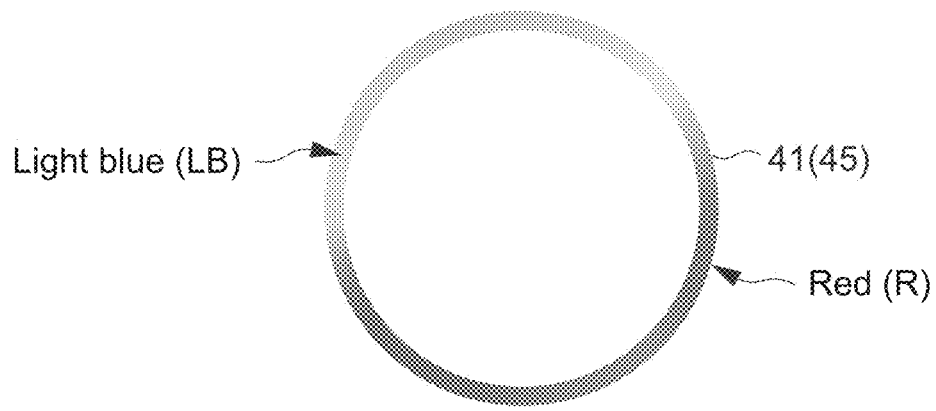
FIG. 8 is a schematic diagram showing an example of an average hue of the edge portion shown in FIG. 6.

FIG. 8 is a schematic diagram showing an example of the average hue of the edge portion 41 shown in FIG. 6. In FIG. 8, for clarity of view, a region corresponding to the edge portion 41 shown in FIG. 6 is schematically shown using a wide annular region. The average hue calculated at each pixel position of the edge portion 41 (edge pixel 45) is represented using a gray scale.

As shown in FIG. 8, the average hue calculated by each edge pixel 45 is a hue reflecting the hue of the hue ring 50 of the original image 25. For example, in the edge pixel 45 of red R, the average hue close to red R is calculated, and in the edge pixel 45 of the light blue LB, the average hue close to the light blue LB is calculated. In practice, various average hues are calculated for each edge pixel 45 according to the subject or a color of a background.

A method of calculating the hue (average hue) of the edge color 44 is not limited. For example, filtering processing such as an averaging filter or a Gaussian filter may be performed on the original image 25, and the hue may be calculated by acquiring the pixel data after applying the filter for each edge pixel 45. The filtering processing is performed, for example, for each target pixel region 51. Thus, it is possible to reduce an influence of noise or the like, and it is possible to stably calculate the hue value of the edge color representing the color of each edge pixel 45.

Note that the predetermined pixel region 51 may be set according to the subject 1. For example, based on a technique such as image recognition, a type of the subject 1 and a surface state of the subject 1 are detected, and the size or the like of the pixel region 51 is set based on a detection result thereof.

For example, when an image of the subject 1 or the like having a fine color pattern on the surface is captured, the pixel region 51 is set to be small. Thus, an influence of colors other than the edge portion 41 is reduced, it is possible to accurately calculate the edge color 44. In a case where the color of the subject is uniform, the pixel region 51 is set to be large. As a result, it is possible to appropriately calculate the edge color 44 in which the color of the periphery of the edge portion 41 is also taken into consideration.

The superimposing color setting unit 32 determines whether or not the average hue of the edge pixel 45 is close to the first color candidate 43a (Step 105). The determination of whether or not the average hue is close to the first color candidate 43a is performed by determining whether or not the average hue is close to either the first color candidate 43a (red R) or the second color candidate 43b (light blue LB) in the hue ring 50. Based on the determination, the superimposing color of the edge pixel 45 is set.

Figure 9A:
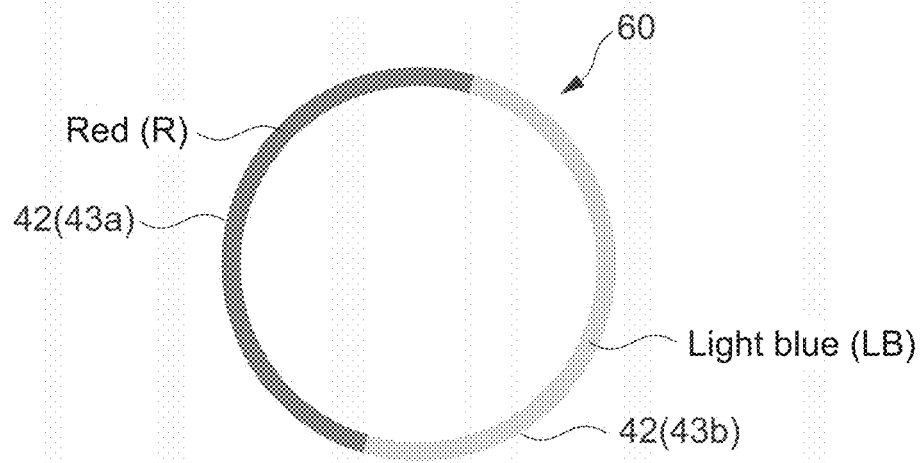
FIGS. 9A and 9B are schematic diagrams each showing an example of the peaking display by the colored superimposing color.
Figure 9B:
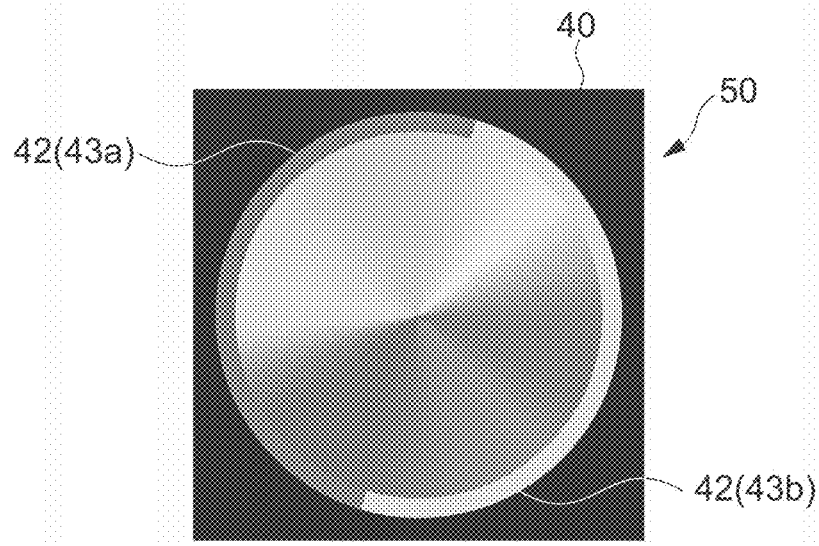

FIGS. 9A and 9B are schematic diagrams each showing an example of the peaking display by colored superimposing color. FIG. 9A is an example of a superimposed image 60 in which the edge portion 41 is displayed in the superimposing color. FIG. 9B is an example of the peaking image 40 obtained by synthesizing the original image 25 and the superimposed image 60.

For example, when the average hue of the edge pixel 45 is far from the first color candidate 43a and is close to the second color candidate 43b (No in Step 105), the superimposing color of the edge pixel 45 is set to the first color candidate 43a (Step 106).

For example, when the average hue outside the range of ±90° with respect to the first color candidate 43a (red R), that is, within the range of ±90° with respect to the second color candidate 43b (light blue LB), is calculated, the superimposing color of the edge pixel 45 is set to the first color candidate 43a (see FIG. 3). Therefore, as shown in FIG. 9A, to the edge pixel 45 where the edge color 44 (average hue) close to the light blue LB is calculated, the highlighted display 42 of red R is set.

Furthermore, for example, when the average hue of the edge pixel 45 is close to the first color candidate 43a and far from the second color candidate 43b (Yes in Step 105), the superimposing color of the edge pixel 45 is set to the second color candidate 43b (Step 107).

For example, when the average hue included in the range of ±90° with respect to the first color candidate 43a (red R), that is, outside the range of ±90° with respect to the second color candidate 43b (light blue LB), is calculated, the superimposing color of the edge pixel 45 is set to the second color candidate 43b (see FIG. 3). Therefore, as shown in FIG. 9B, to the edge pixel 45 where the edge color 44 close to red R (average hue) is calculated, the highlighted display 42 of the light blue LB is set.

As described above, the superimposing color of the edge pixel 45 is set to the second color candidate 43b having the complementary color relationship when the hue value of the average hue is close to the hue value of the first color candidate 43a, and is set to the first color candidate 43a when the average hue value is far therefrom. That is, the superimposing color setting unit 32 sets the color candidate 43 having the hue farthest from the hue of the edge color 44 among the plurality of color candidates as the superimposing color.

FIG. 9B schematically shows the peaking image 40 in which the edge-portion 41 of the hue ring 50 included in the original image 25 is highlighted. For example, in the edge portion 41 (left side in FIG. 9B) of the light blue LB in the hue ring 50, the superimposing color is red R (first color candidate 43a). Therefore, it is possible to easily distinguish the light blue portion of the hue ring 50 from the highlighted display 42 (red) of the edge portion 41. Furthermore, for example, in the edge portion 41 (right side FIG. 9B) of red R in the hue ring 50, the superimposing color becomes the light blue LB (second color candidate 43b). This makes it possible to easily distinguish the red portion of the hue ring 50 from the highlighted display 42 (light blue) of the edge portion 41.

When the superimposing color of the edge pixel 45 is set to one of the first and second color candidates 43a and 43b, it is determined whether or not the processing is performed on all the pixels of the original image 25 (Step 108). If there remains a pixel for which the processing is not performed (No in Step 108), the processing in Step 102 or later is repeated. If the processing is performed on all the pixels (Yes in Step 109), the processing on the original image 25 is completed. Then, the processing of the peaking display for the next original image 25 is started.

Figure 10A:
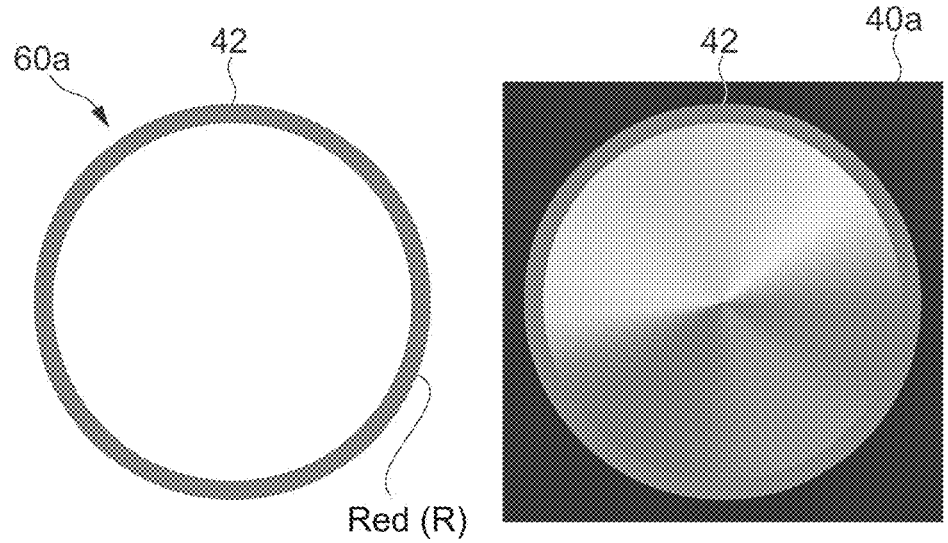
FIGS. 10A and 10B are schematic diagrams each showing an example of the peaking display as a comparative example.
Figure 10B:
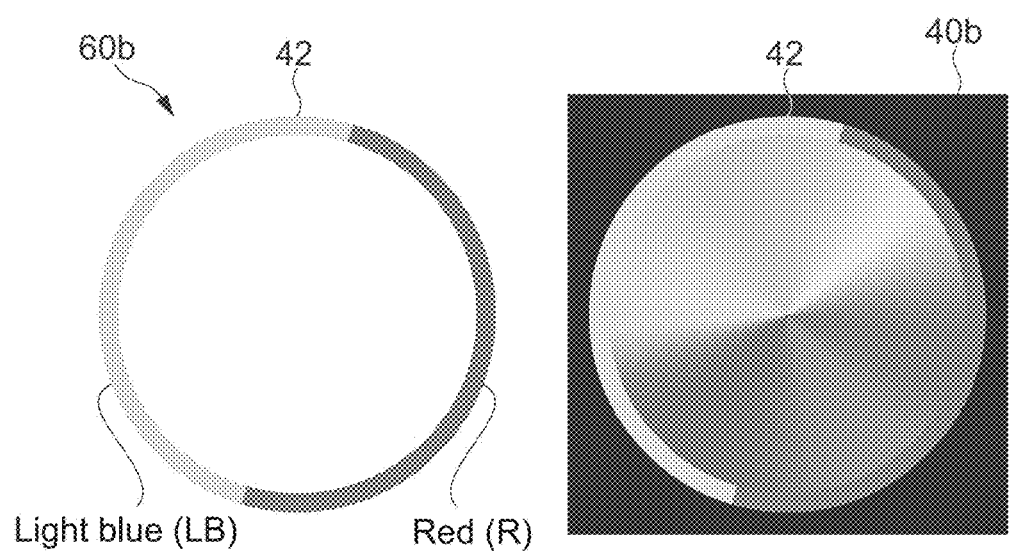

FIGS. 10A and 10B are schematic diagrams showing examples of the peaking display as a comparative example. The left and right diagrams of FIG. 10A show a superimposed image 60a and a peaking image 40a when a single superimposing color (red R) is used. As shown in FIG. 10A, when the superimposing color is represented only by red R, a hue difference between red-based edge portions 41 in the hue ring 50 is small, so that it is difficult to distinguish the portion of the highlighted display 42 (peaking) from the portion of the subject 1 (hue ring 50).

The left and right diagrams of FIG. 10B are a superimposed image 60b and a peaking image 40b when a color close to the hue of the edge color 44 form red R and light blue LB is the superimposing color. In FIG. 10B, in the hue ring 50, the superimposing color of the light blue LB is set in blue-based edge portion 41 and the superimposing color of red R is set in red-based edge portion 41. Therefore, the hue difference is decreased both in the red-based and blue-based edge portions 41, and the visibility of the highlighted display 42 is lowered.

In contrast, in the peaking image 40 shown in FIG. 9B, the superimposing color is set such that the hue difference with respect to the edge color 44 becomes large. Therefore, the visibility of the peaking display (highlighted display 42) is improved for any edge portion 41 regardless of the hue. Thus, it is possible to easily determine where a focus of an imaging range, and it is possible to sufficiently support the focus operation of the image capture apparatus 100.

[Peaking Display by Black and White Superimposing Color]

Hereinafter, a case in which an achromatic color (black and white, etc.) having no hue is used as the superimposing color (plural color candidates 43) will be described.

In the present embodiment, the superimposing color of the achromatic colors can be set. In this case, the plurality of color candidates 43 include color candidates 43 of the achromatic colors. The achromatic color candidates 43 are set from colors such as white, black, and gray represented by predetermined brightness. Each of the color candidates 43 is set to have a different brightness. Hereinafter, a case in which black and white are used as the achromatic color candidates 43 will be described. That is, the plurality of color candidates 43 include black and white.

In the peaking display using a black-and-white superimposing color (color candidates 43), a color whose brightness (luminance) is far from the edge color 44 is set as the superimposing color of the edge portion 41 out of the two color candidates (black and white). That is, the superimposing color is controlled such that the edge color 44 and the superimposing color are colors far in a brightness direction.

The edge color 44 is a color represented by color information (pixel data, etc.) about the edge portion 41 of the original image 25, and is typically a chromatic color. Therefore, in a black-and-white peaking display, the superimposing color is controlled based on the brightness (luminance) of the colored edge color 44.

For example, if the edge color 44 is brighter than a predetermined threshold value, black having low brightness is set to the superimposing color of the edge portion 41. Furthermore, for example, if the edge color 44 is darker than the predetermined threshold value, white having high brightness is set to the superimposing color of the edge portion. Thus, since each edge portion 41 is displayed in the superimposing color having brightness far from the edge color 44, it is possible to greatly improve the visibility of the highlighted display 42 of the edge portion 41.

Figure 11:
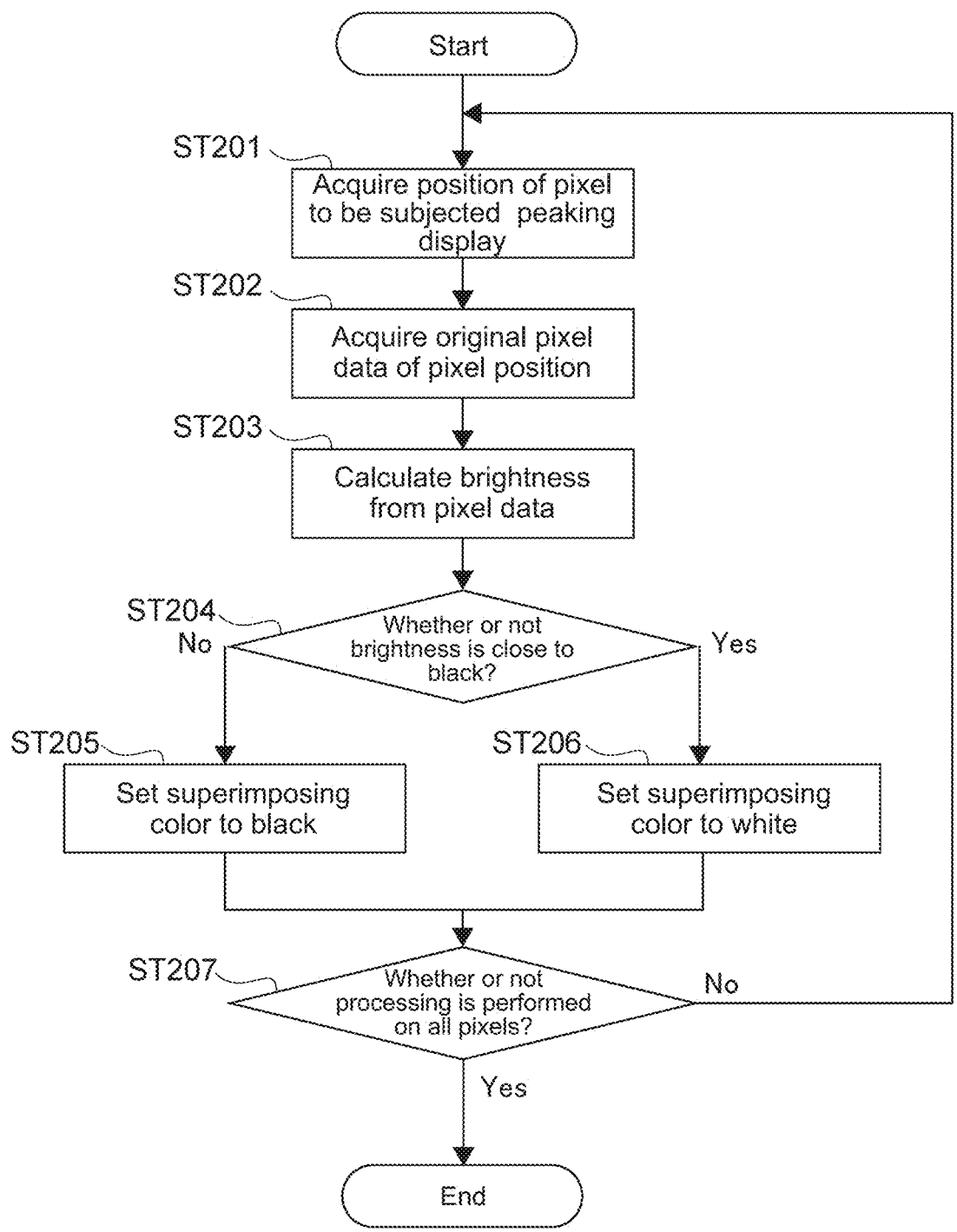
FIG. 11 is a flowchart showing an example of a peaking display using a black-and-white superimposing color.
Figure 12:
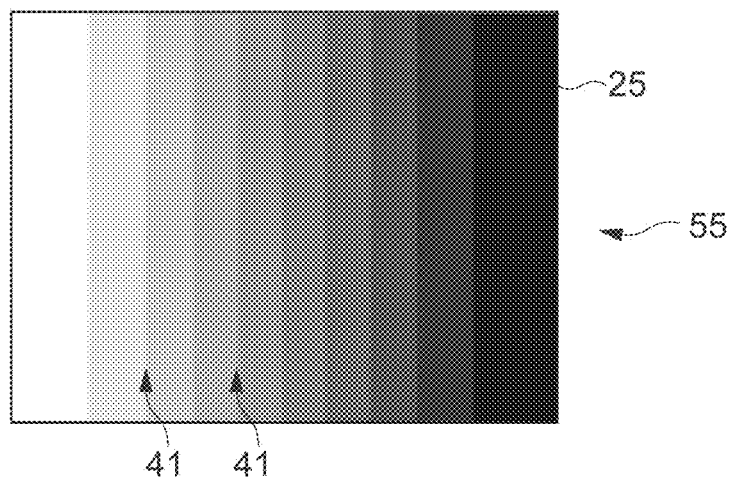
FIG. 12 shows an image of a stripe pattern which is an example of the original image.

FIG. 11 is a flowchart showing an example of the peaking display using the black-and-white superimposing color. FIG. 12 shows an image of a stripe pattern 55, which is an example of the original image. Hereinafter, the peaking display processing using the black-and-white superimposing color will be described with reference to FIG. 11 by taking the original image 25 shown in FIG. 12 as an example.

FIG. 12 shows a captured image (original image 25) in which a stripe pattern 55 is captured as an example of the subject 1. The stripe pattern 55 is a pattern in which rectangular regions in the form of strips are continuously arranged in the lateral direction in FIG. 12. Each rectangular region is filled in such a manner as to have a gradation from white to black in order from the left side. That is, the stripe pattern 55 is a gray scale gradation pattern.

First, the positions of the pixels to be subjected to the peaking display are acquired by the superimposing color setting unit 32 (Step 201). Specifically, the pixel positions of the edge pixel 45 corresponding to the edge portions 41 are read.

Figure 13:
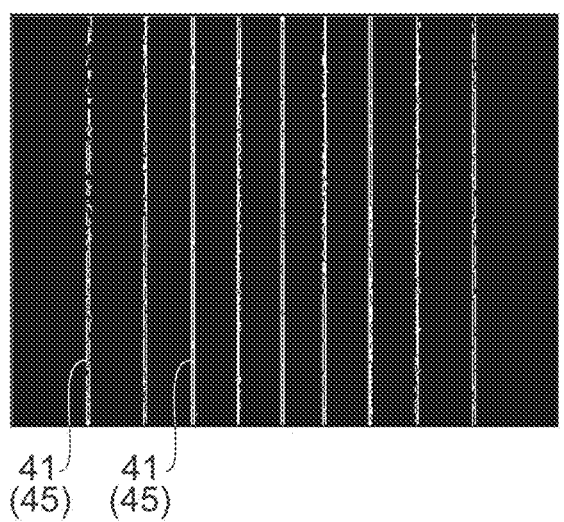
FIG. 13 is an image showing the edge portion detected from the original image shown in FIG. 12.

FIG. 13 is an image showing the edge portion 41 detected from the original image 25 shown in FIG. 12. In FIG. 13, the pixels (edge pixels 45) corresponding to the edge portions 41 of the original image 25 including the stripe pattern 55 are shown in white. From the stripe pattern 55, boundaries of the respective rectangular regions are detected as the edge portions 41. Thus, as shown in FIG. 13, the edge pixels 45 of the stripe pattern 55 will be distributed along the lines in the vertical direction corresponding to the boundaries of the respective rectangular regions.

The pixel data of the pixel positions acquired in Step 201 is acquired (Step 202). That is, the pixel data (color information) of the edge pixels 45 is read from the original image 25. Then, the brightness of the pixel data of the edge pixels 45 is calculated by the superimposing color setting unit (Step 203). Thus, in the processing shown in FIG. 11, the pixel data of the edge pixels 45 becomes the color information about the edge portions 41, each color of the edge pixels 45 becomes the edge color 44. The brightness of the edge color 44 is appropriately calculated.

For example, if the original image 25 as in FIG. 12 is the gray scale image, a gradation value of the pixel data is calculated as the brightness of the edge pixel 45. If the pixel data is the RGB data, brightness is calculated based on each intensity value of RGB.

Figure 14:
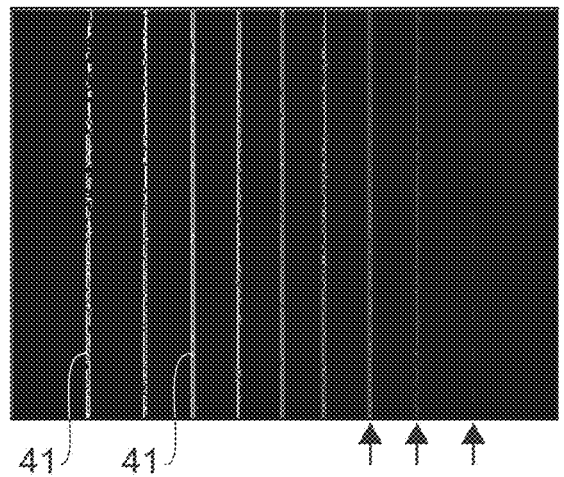
FIG. 14 is a schematic diagram showing an example of brightness in the original image of the edge portions 41 shown in FIG. 13.

FIG. 14 is a schematic diagram showing an example of the brightness in the original image 25 of the edge portions 41 shown in FIG. 13. As shown in FIG. 14, for example, at the boundaries of the white rectangular regions (edge portions 41 of left end in FIG. 14), bright brightness is calculated. The brightness calculated at each boundary (edge portion 41) becomes darker as it is closer to the right side. In FIG. 14, since the background is displayed in black, although a brightness display of the edge portion 41 on the right side in FIG. 14 is no longer visible, in fact, the brightness close to black in the position indicated by arrows is calculated.

In the example shown in FIG. 14, the brightness of the pixels corresponding to the edge portions 41 (edge pixels 45) is calculated as it is, but is not limited thereto. For example, the predetermined pixel region 51 described with reference to FIG. 7 may be set. In this case, (reference pixel 47) pixel data of the edge pixel 45 and the peripheral pixels 46 included in the pixel region 51 is acquired, the average brightness or the like in the pixel region 51 is calculated. That is, based on the pixel data of the references pixel 47, the brightness of the edge color 44 may be calculated. This makes it possible to set the superimposing color in accordance with the brightness of the periphery.

The superimposing color setting unit 32 determines whether or not the brightness of the edge pixel 45 is close to black (Step 204). This is performed by determining that the brightness of the edge pixel 45 (brightness of edge color 44) is close to black and white in the brightness direction.

In the present embodiment, the superimposing color setting unit 32 sets the superimposing color to black when the brightness of the edge color 44 is larger than the predetermined threshold value, and sets the superimposing color to white when the brightness of the edge color 44 is smaller than the predetermined threshold value. Based on this determination, the superimposing color of the edge pixel 45 is set.

The predetermined threshold value is set to, for example, an intermediate value between black and white. For example, when the brightness of each color is represented by 256 gradations (when brightness of black is 1 and brightness of white is 256), the predetermined threshold value is set to 128. When the brightness of each color is represented by 128 gradations, the predetermined brightness is set to 64. The predetermined threshold value is not limited to this, and may be appropriately set in accordance with, for example, the brightness of a screen or the like.

Figure 15A:
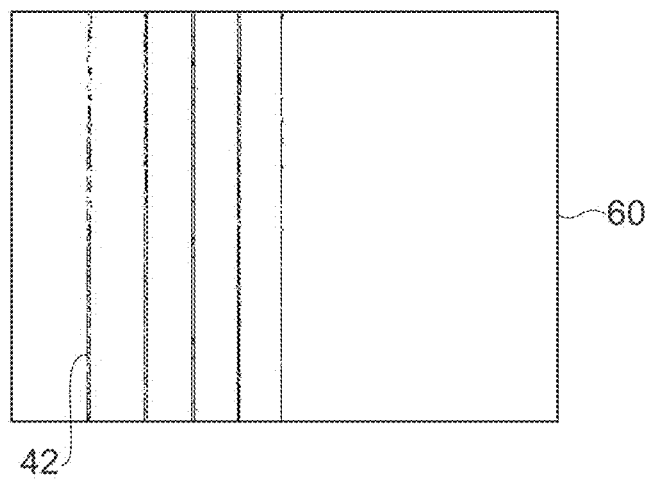
FIGS. 15A, 15B, and 15C are schematic diagrams each showing an example of the peaking display using the black-and-white superimposing color.
Figure 15B:
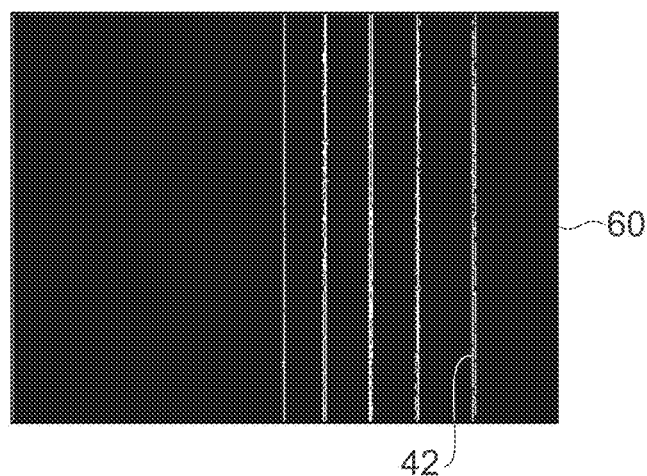
Figure 15C:
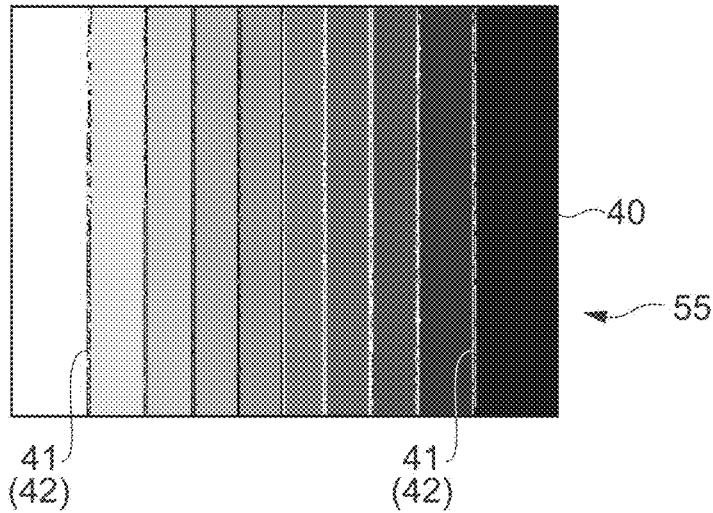

FIGS. 15A, 15B, and 15C are schematic diagrams each showing an example of the peaking display using the black-and-white superimposing color. FIGS. 15A and 15B are examples of the superimposed images 60 in which the edge portions 41 are displayed in the black-and-white superimposing colors. FIG. 15C is an example of the peaking image 40 obtained by synthesizing the original image 25 and the superimposed image 60.

For example, if the brightness of the edge pixel 45 is higher than the predetermined threshold value and closer to white than black (No in Step 204), the superimposing color of the edge pixel 45 is set to black (Step 205). For example, at the edge pixel 45 on the left side of the stripe pattern 55, the brightness close to white is calculated (see FIG. 14).

Thus, as shown in FIG. 15A, at the edge pixel 45 brightness close to white is calculated (left edge pixel 45 of stripe pattern 55), the black highlighted display 42 is set.

Furthermore, for example, if the brightness of the edge pixel 45 is lower than the predetermined threshold value and is close to black (Yes in Step 204), the superimposing color of the edge pixel 45 is set to white (Step 206). For example, at the edge pixel 45 on the right side of the stripe pattern 55, the brightness close to black is calculated (see FIG. 14). Thus, as shown in FIG. 15B, at the edge pixel 45 brightness close to black is calculated (left edge pixel 45 of stripe pattern 55), the white highlighted display 42 is set.

In a central boundary portion of the stripe pattern 55, both the edge pixel 45 close to white and the edge pixel 45 close to black are detected. In this case, even at the same boundary, for the edge pixel 45 that is brighter than the predetermined threshold value, the superimposing color of black is set, and for the dark edge pixel 45, the superimposing color of white is set.

As described above, the superimposing color of the edge pixel 45 is set to white if the brightness thereof is close to black, and is in contrast set to black if the brightness thereof is close to white. That is, the superimposing color setting unit 32 sets the color candidate 43 having the brightness farthest from the brightness of the edge color 44 among the plurality of color candidates 43 (black and white) as the superimposing color.

FIG. 15C schematically shows the peaking image 40 in which the edge portions 41 of the stripe pattern 55 included in the original image 25 are highlighted. For example, in the stripe pattern 55, the superimposing color is black at the right boundary (edge portion 41) close to white. At the right boundary (edge portion 41) close to black, the superimposing color is white. Thus, as shown in FIG. 15C, it is possible to sufficiently improve the visibility of the peaking display from a high brightness portion to a low brightness portion.

When the superimposing color of the edge pixel 45 is set to either black or white, it is determined whether or not the processing is performed on all the pixels of the original image 25 (Step 208). If there remains a pixel for which the processing is not performed (No in Step 208), the processing in Step 201 and later is repeated. When the processing is performed on all the pixels (Yes in Step 208), the processing on the original image 25 is completed. Thus, the superimposition pattern of black and white is determined for each pixel of the peaking display shown in FIG. 15C. Then, the processing of the peaking display for the next original image 25 is started.

Figure 16:
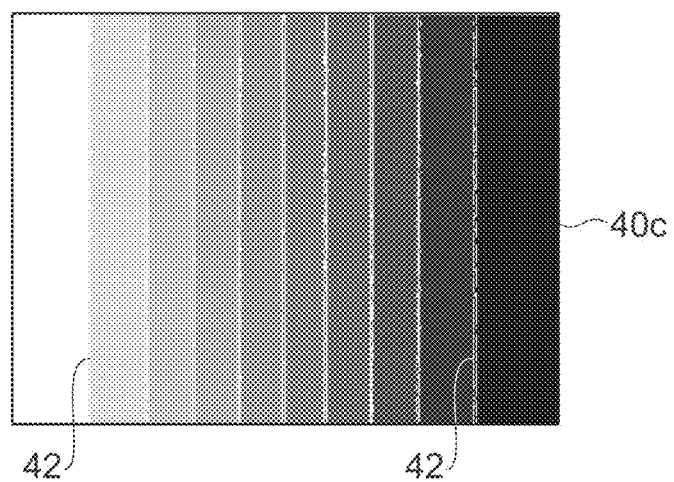
FIG. 16 shows a peaking image as a comparative example.

FIG. 16 shows a peaking image 40c as a comparative example. In the peaking image 40c shown in FIG. 16, a single superimposing color (white) is used. If the superimposing color is only white, at the edge portion 41 on the right side having low brightness, the highlighted display 42 can be visually recognized, but at the edge portion 41 on the left side having high brightness, it is difficult to distinguish between the highlighted display 42 and the subject (stripe pattern 55).

In contrast, in the peaking image 40 shown in FIG. 15C, the superimposing color is set such that a brightness difference with the edge color 44 increases. Therefore, the visibility of the peaking display (highlighted display 42) is improved for any edge portion 41 regardless of the brightness of the edge portion 41. Thus, it is possible to easily determine where the focus of the imaging range, and it is possible to sufficiently support the focus operation of the image capture apparatus 100.

As described above, in the image capture apparatus 100 according to the present embodiment, the captured image of the subject 1 (original image 25) is generated, and the edge portion 41 included in the original image 25 is detected. Furthermore, for each detected edge portion 41, the color of the highlighted display 42 for highlighting the edge portion 41 is controlled using the color information about the edge portion 41 in the original image 25. This makes it possible to improve the visibility of the highlighted display 42 of the edge portion 41.

As a method of highlighting the edge of the subject, a method of darkening the color of the edge, a method of superimposing a single color, or the like is considered. In this case, depending on the color and background around the edge, it may be difficult to identify the portion of the highlighted edge.

In the present embodiment, the color (superimposing color) of the highlighted display 42 for highlighting the edge portion 41 is set to a color far from the color of the edge portion 41 (edge color 44) in the original image 25. Thus, the superimposing color can be made conspicuous regardless of the color of the edge portion 41 itself in the original image 25 or the color of the periphery of the edge portion 41. Thus, it is possible to improve the visibility of the highlighted display 42.

In colored peaking display, for example, two complementary colors (first and second color candidates 43a and 43b) are set as the superimposing colors. The superimposing colors are automatically selected in accordance with the hue of the edge portion 41 (hue of edge color 44) so as to be the colors that are easy for the user to visually recognize. As described above, since the peaking display is performed with the color having the larger hue difference in accordance with the color around a peaking position, the user can easily recognize the peaking portion with respect to the color of any hue.

In the black-and-white peaking display, for example, the black-and-white superimposing color is automatically selected so as to be the color that is easy for the user to visually recognize, in accordance with the brightness of the edge portion 41 (brightness of edge color 44). This makes it possible to improve the visibility of the peaking display regardless of the brightness or the like of the edge portion 41.

In addition, the superimposing color used for the highlighted display 42 changes in accordance with the change in the color of the peaking position (edge portion 41). This makes it possible to maintain the visibility of the highlighted display 42 even when, for example, a composition of the original image 25, the subject, or the like constantly changes. As a result, it is possible to display the focus position in the color that is easy to visually recognize at all times, and it is possible to exhibit high usability.

In addition, it is possible to perform the peaking display by using the superimposing colors (plural color candidates 43) selected by the user. In the image capturing apparatus 100, the superimposing color corresponding to the color of the edge portion 41 is automatically set using the color candidate 43 selected by the user. This makes it possible to easily recognize the highlighted display 42 of the edge portion 41.

In the image capture apparatus 100, the peaking image 40 is generated by modifying only the edge portion 41 of the original image 25. That is, the peaking display is limited to only the edge portion 41, and the rest is the same as the normal image. As a result, it is possible to realize an imaging state in which the user does not feel uncomfortable without decreasing the visibility of the peaking display. This makes it possible to perform a natural focus operation and exhibit excellent operability.

OTHER EMBODIMENTS

The present technology is not limited to the embodiments described above, and can achieve various other embodiments.

In the above description, a method of setting the display (highlighted display 42) of the edge portion 41 of the peaking image 40 according to the edge color 44 is described. For example, it is possible to control the highlighted display 42 such that the display of the edge portion 41 changes with time. That is, it is possible to control the color of the highlighted display 42 such that the display of the edge portion 41 of the peaking image 40 changes dynamically.

For example, the color of the highlighted display 42 may be set to switch at a constant time. For example, when two color candidates 43 are used, the color candidates 43 set as the respective highlighted displays 42 are switched to become other color candidates 43 at preset time intervals. As a result, since the color of the highlighted display 42 is constantly switched and displayed, the edge portion 41 can be easily detected.

For example, the highlighted display 42 may be displayed to blink at constant time intervals. In this case, a state of displaying the highlighted display 42, and a state of not displaying the highlighted display 42 is repeated alternately. In this manner, the edge portion 41 can be easily detected by blinking the highlighted display 42 of the edge portion 41, that is, by giving a motion to the highlighted display 42. Alternatively, any method of dynamically changing the display of the edge portion 41 may be used.

Figure 17A:
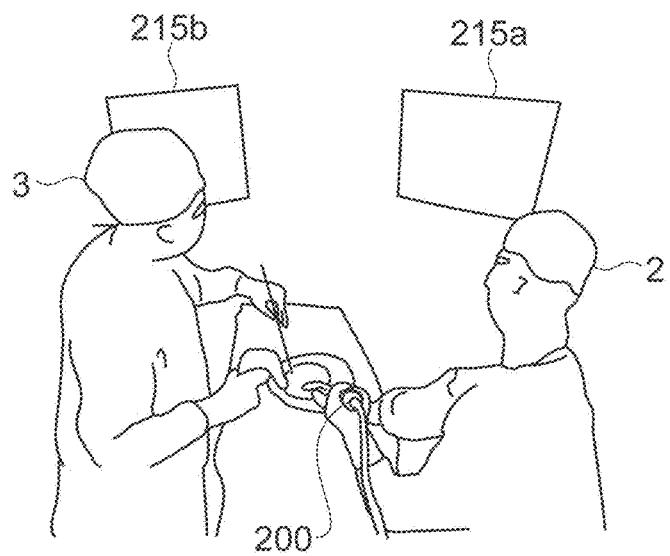
FIGS. 17A, 17B, and 17C are schematic diagrams each for explaining an application example of the peaking display.
Figure 17B:
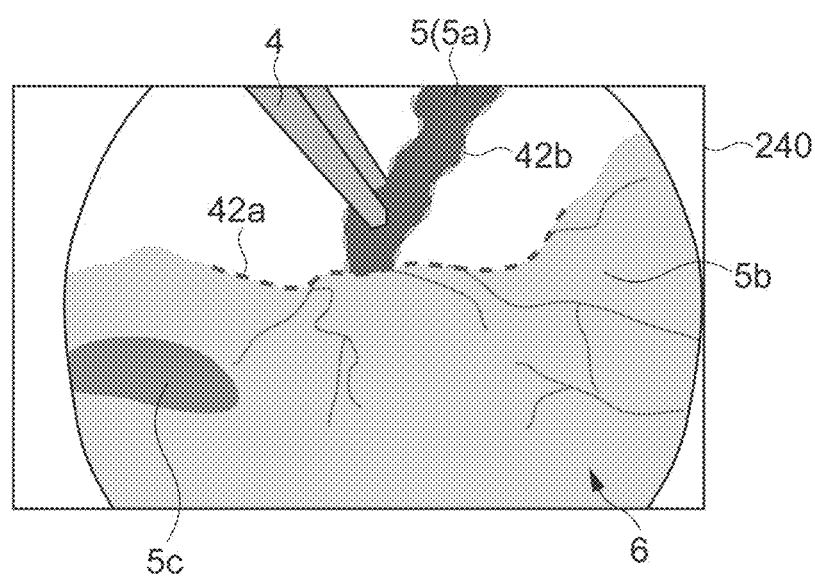
Figure 17C:
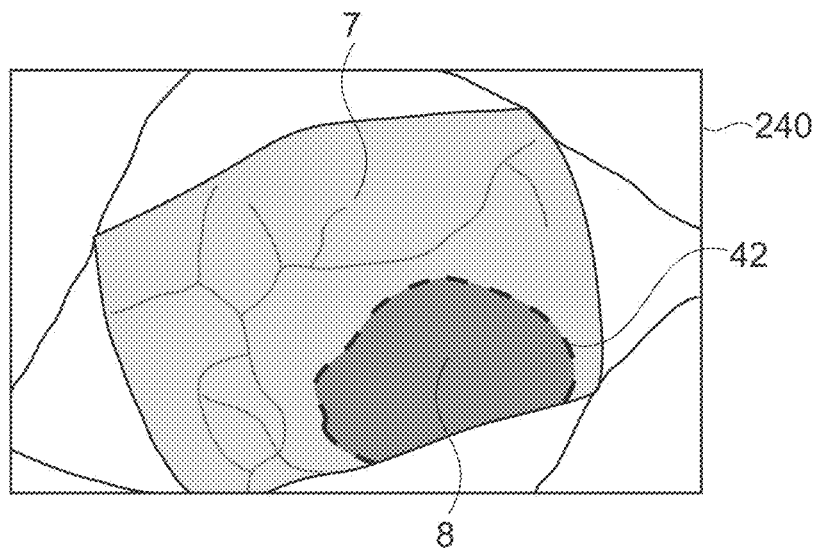

FIGS. 17A, 17B, and 17C are schematic diagrams each for explaining an application example of the peaking display. FIG. 17A schematically shows a state of surgery using the image capture apparatus. FIG. 17B and FIG. 17C are schematic diagrams each showing an example of the peaking displays applied to an image obtained by capturing a surgical field. In FIGS. 17B and 17C, the highlighted displays 42 are schematically shown using dotted lines.

For example, in a case where a double-cavity surgery, a laparotomy, or the like is performed, the image capture apparatus (endoscope camera or the like) for imaging an affected part or the like in a body is used. In addition, for example, when a craniotomy operation or the like is performed, the image capture apparatus that enlarges and captures an image of the affected part is used. The present technology can be suitably applied to such an image capture apparatus.

FIG. 17A shows a state in which a scopist 2 who performs manual focus of an endoscope camera 200 in the surgery performs the focus operation of the endoscope camera 200 while viewing a monitor 215b different from a monitor 215a viewed by a doctor 3 who performs the surgery. In this case, the peaking display using the present technology is performed only on an image displayed on the monitor 215b viewed by the scopist 2, and the peaking display is not performed on an image (monitor 215a) viewed by the doctor 3 who performs the surgery. As a result, the operation of focusing the endoscopic camera 200 on the affected part can be facilitated by the scope 2 without affecting the doctor 3 who performs the surgery.

FIG. 17B is an example of a peaking image 240 obtained by applying the peaking display to an image (intraoperative image) captured by the endoscopic camera 200. FIG. 17B shows a state that a part of an organ 5a is pinched by a forceps 4 operated by the doctor 3. The organ 5a pinched by the forceps 4 is connected to an organ 5b covered by fat 6. Other organ 5c is present on the organ 5b covered with the fat 6.

The superimposing color used for the peaking display can be set according to the organs 5a to 5c (subject 1). That is, the plurality of color candidates 43 which are candidates for the superimposing colors are set in accordance with the subject 1. Hereinafter, a method of setting the color candidates 43 (superimposing colors) according to the subject 1 will be described in detail.

For example, the organs 5, the fat 6, and the like included in the intraoperative image are detected using the image recognition processing or the like. For example, when a periphery of the fat 6 is a surgery target, the fat 6 is set as a target subject. In this case, a color (blue) which becomes a complementary color of a color (yellow) of the fat 6 is set as one color candidate 43. As a result, when the focus is on the periphery of the fat 6, the edge portion 41 is displayed by the blue highlighted display 42a, and the focus position can be easily visually recognized.

Furthermore, for example, the forceps 4 in the intraoperative image may be detected by using the image recognition processing or the like. In this case, the organ (organ 5a) in the vicinity of the forceps 4 is set as the target subject. In this case, the color that becomes the complementary color of the organ 5a that is the target subject is set as the color candidate 43. As a result, it is possible to display a contour or the like of the organ 5a to be performed the surgery by the highlighted display 42b in which the complementary color of the color of the organ 5a is set. Thus, it is possible to easily perform the focus operation on the target subject.

FIG. 17C is an example of the peaking image 240 obtained by applying the peaking display to an intraoperative image in which a tumor portion is imaged. FIG. 17C schematically shows a part of a brain 7 exposed by, for example, a craniotomy, and a tumor 8.

For example, the tumor 8 is detected using image recognition processing or the like. The tumor 8 can be detected using, for example, a difference in color from a normal brain 7. The color of the highlighted display 42 (color candidate 43) is set so as to be complementary to the color of the tumor 8. This makes it possible to highlight the edge portion 41 detected by the tumor 8 with a color that is easy to distinguish. In addition, a method of setting the color candidate 43 according to the subject 1 is not limited.

APPLICATION EXAMPLES

The technology according to the present disclosure is applicable to various products. For example, the technology according to the present disclosure may be applied to an endoscopic surgery system.

Figure 18:
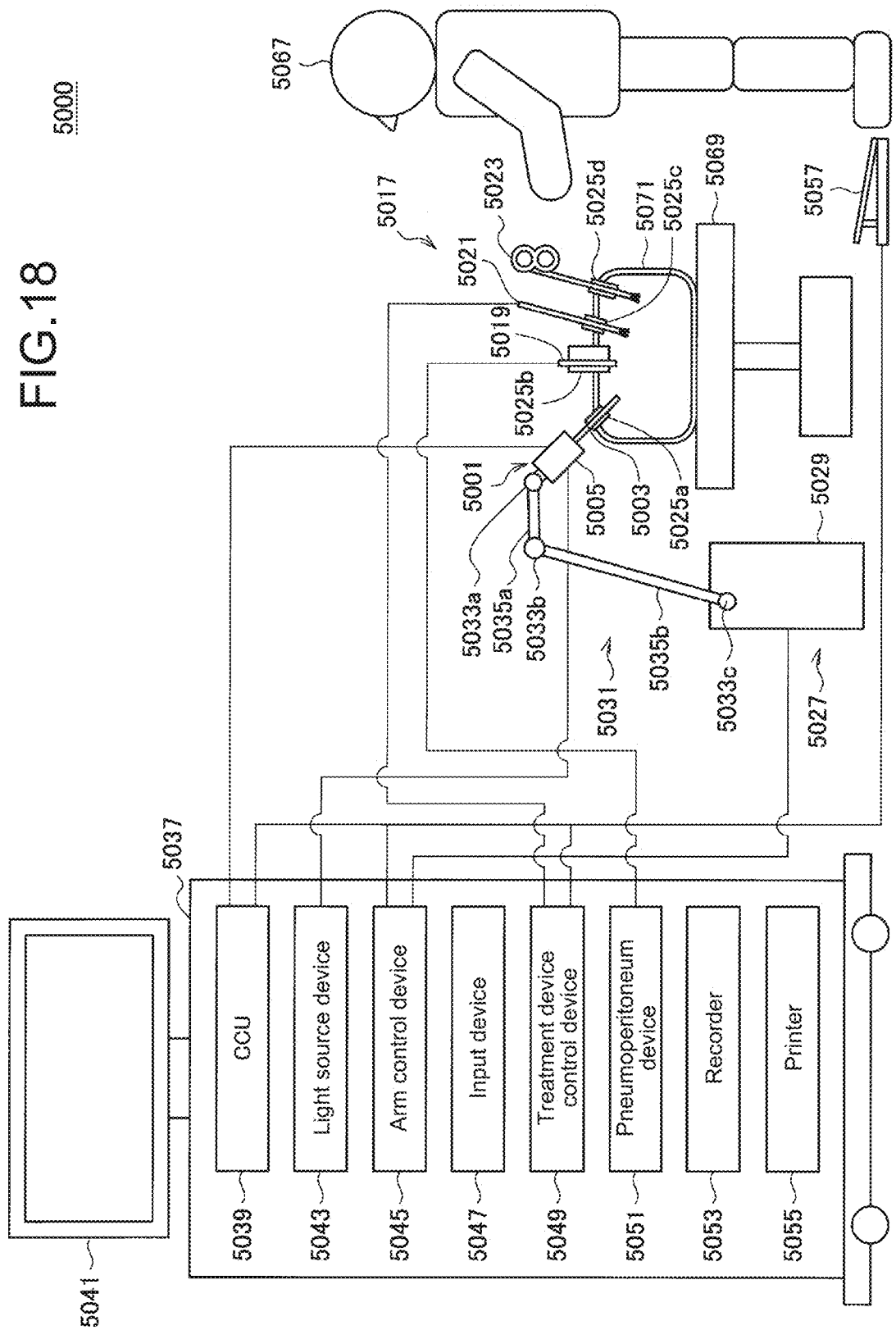
FIG. 18 is a diagram showing an example of a schematic configuration of an endoscopic surgery system.

FIG. 18 is a diagram showing an example of a schematic configuration of an endoscopic surgery system 5000 to which the technologies according to the present disclosure may be applied. FIG. 18 shows a state that an surgeon (doctor) 5067 performs the surgery on a patient 5071 on a patient bed 5069 using the endoscopic surgery system 5000. As shown, the endoscopic surgery system 5000 includes an endoscope 5001, other surgical tools 5017, a support arm device 5027 for supporting the endoscope 5001, and a cart 5037 on which various devices for endoscopic surgery are mounted.

In the endoscopic surgery, instead of incising an abdominal wall, a plurality of cylindrical opening tools called trockers 5025a to 5025d are inserted into the abdominal wall. Then, a lens barrel 5003 of the endoscope 5001 and other surgical tools 5017 are inserted into a body cavity of the patient 5071 from the trockers 5025a to 5025d. In the example shown, as the other surgical tools 5017, a pneumoperitoneum tube 5019, an energy treatment tool 5021, and a forceps 5023 are inserted into the body cavity of the patient 5071. The energy treatment tool 5021 is a treatment tool for performing incision and peeling of tissues, sealing of blood vessels, or the like by high-frequency current or ultrasonic vibration. However, the surgical tools 5017 shown in the drawing is merely an example, and various surgical tools generally used in the endoscopic surgery such as a tweezer and a retractor may be used as the surgical tools 5017.

An image of a surgery part in the body cavity of the patient 5071 imaged by the endoscope 5001 is displayed on a display device 5041. The surgeon 5067 uses the energy treatment tool 5021 and the forceps 5023 to perform treatment such as resection of the affected part while viewing an image of the surgery part displayed on the display device 5041 in real time. Although not shown, the pneumoperitoneum tube 5019, the energy treatment tool 5021, and the forceps 5023 are supported by the surgeon 5067, an assistant, or the like during the surgery.

(Support Arm Device)

The support arm device 5027 includes an arm portion 5031 extending from a base portion 5029. In the example shown, the arm portion 5031 includes joint portions 5033a, 5033b, and 5033c, and links 5035a and 5035b, and is driven under the control of an arm control device 5045. The endoscope 5001 is supported by the arm portion 5031, and its position and posture are controlled. Thus, fixation at a stable position of the endoscope 5001 can be realized.

(Endoscope)

The endoscope 5001 includes the lens barrel 5003 in which a region of a predetermined length from a distal end is inserted into the body cavity of the patient 5071, and a camera head 5005 connected to a base end of the lens barrel 5003. In the example shown, the endoscope 5001 configured as a so-called rigid scope having a rigid lens barrel 5003 is shown, but the endoscope 5001 may be configured as a so-called flexible scope having a flexible lens barrel 5003.

At the distal end of the lens barrel 5003, an opening in which an objective lens is fitted is provided. A light source device 5043 is connected to the endoscope 5001, and light generated by the light source device 5043 is guided to the distal end of the lens barrel by a light guide extending inside the lens barrel 5003, and irradiated to an observation target in the body cavity of the patient 5071 via the objective lens. Note that the endoscope 5001 may be a direct scope or a perspective view scope or a side scope.

Inside the camera head 5005, an optical system and the image capture element are provided, and reflected light from an observation subject (observation light) is focused on the image capture element by the optical system. The observation light is photoelectrically converted by the image capture element, and an electrical signal corresponding to the observation light, i.e. an image signal corresponding to an observation image, is generated. The image signal is transmitted to a camera control unit (CCU) 5039 as RAW data. Incidentally, the camera head 5005 includes a function of adjusting magnification and a focal length by appropriately driving the optical system.

Note that a plurality of image capture elements may be provided in the camera head 5005 in order to cope with, for example, stereoscopic vision (3D display) or the like. In this case, inside the lens barrel 5003, in order to guide the observation light to each of the plurality of image capture elements, a plurality of relay optical systems is provided.

(Various Devices Mounted on Cart)

The CCU 5039 includes the CPU (Central Processing Unit), a GPU (Graphics Processing Unit), and the like, and collectively controls the operations of the endoscope 5001 and the display device 5041. Specifically, the CCU 5039 performs various image processing for displaying an image based on the image signal such as, for example, development processing (demosaicing processing), on the image signal received from the camera head 5005. The CCU 5039 provides the display device 5041 with the image signal to which the image processing is applied. The CCU 5039 also transmits a control signal to the camera head 5005 and controls driving thereof. Such control signal may include information about capturing conditions such as the magnification and the focal length.

The display device 5041 displays an image based on the image signal which is subjected to the image processing by the CCU 5039 by control from the CCU 5039. When the endoscope 5001 is compatible with high-resolution imaging such as 4K (number of horizontal pixels 3840×number of vertical pixels 2160) or 8K (number of horizontal pixels 7680×number of vertical pixels 4320) and/or is compatible with 3D display, the display device 5041 capable of high-resolution display and/or capable of 3D display corresponding thereto can be used. In the case of the display device is compatible with the high-resolution imaging such as 4K or 8K, a more immersive feeling can be obtained by using the display device having a size of 55 inches or more as the display device 5041. In addition, a plurality of display devices 5041 having different resolutions and sizes may be provided depending on the applications.

The light source device 5043 is configured of a light source such as an LED (light emitting diode), for example, and supplies irradiation light to the endoscope 5001 at the time of imaging the surgery part.

The arm control device 5045 is configured of a processor such as the CPU, for example, and operates in accordance with the predetermined program to control driving of the arm portion 5031 of the support arm device 5027 in accordance with a predetermined control method.

An input device 5047 is an input interface to the endoscopic surgery system 5000. The user can input various types of information and instructions to the endoscopic surgery system 5000 via the input device 5047. For example, the user inputs various types of information about the surgery such as body information of the patient and information about a surgical procedure, via the input device 5047. In addition, for example, the user inputs an instruction to drive the arm portion 5031, an instruction to change capturing conditions (type, magnification, focal length, etc.) of the endoscope 5001, an instruction to drive the energy treatment tool 5021, and the like via the input device 5047.

The type of the input device 5047 is not limited, and the input device 5047 may be any of various known input devices. As the input device 5047, for example, a mouse, a keyboard, a touch panel, a switch, a foot switch 5057, a lever, or the like can be used. When the touch panel is used as the input device 5047, the touch panel may be provided on a display surface of the display device 5041.

Alternately, the input device 5047 is a device that is mounted by the user such as a wearable device or an HMD (Head Mounted Display) of the glass type, and various inputs are made according to a gesture or a line of sight of the user detected by the device. The input device 5047 also includes a camera capable of detecting the movement of the user, and various inputs are made according to the gesture or the line of sight of the user detected from an image captured by the camera. Furthermore, the input device 5047 includes a microphone capable of picking up a voice of the user, and various inputs are made by the voice through the microphone. In this manner, by configuring the input device 5047 so as to be able to input various types of information without contact, it is possible for a user belonging to a particularly clean area (for example, surgeon 5067) to operate a device belonging to a dirty area without contact. In addition, the user can operate the device without releasing his or her hand from the device, thereby improving the convenience of the user.

The treatment device control device 5049 controls driving of the energy treatment device 5021 for cauterization of tissues, incision or sealing of blood vessels, and the like. The pneumoperitoneum device 5051 delivers gas into the body cavity of the patient 5071 through the pneumoperitoneum tube 5019 in order to inflate the body cavity for the purpose of securing the field of view by the endoscope 5001 and securing the working space of the surgeon. A recorder 5053 is a device capable of recording various types of information about the surgery. A printer 5055 is a device capable of printing various types of information about the surgery in various formats such as text, images and graphs.

Hereinafter, a configuration particularly characteristic of the endoscopic surgery system 5000 will be described in more detail.

(Support Arm Device)

The support arm device 5027 includes a base portion 5029 serving as a base and an arm portion 5031 extending from the base portion 5029. In the example shown, the arm portion 5031 includes a plurality of joint portions 5033a, 5033b, 5033c, and a plurality of links 5035a, 5035b connected by the joint portion 5033b, but in FIG. 18, the configuration of the arm portion 5031 is shown in a simplified manner for simplicity. Actually, the shapes, the number, and the arrangement of the joint portions 5033a to 5033c and the links 5035a and 5035b, directions of rotation axes of the joint portions 5033a to 5033c, and the like can be appropriately set so that the arm portion 5031 has a desired degree of freedom. For example, the arm portion 5031 may be suitably configured to have six or more degrees of freedom. Thus, since it becomes possible to freely move the endoscope 5001 within a movable range of the arm portion 5031, it is possible to insert the lens barrel 5003 of the endoscope 5001 into the body cavity of the patient 5071 from a desired direction.

The joint portions 5033a to 5033c are provided with actuators, and the joint portions 5033a to 5033c are configured to be rotatable around predetermined rotation axes by driving the actuators. The driving of the actuators is controlled by the arm control device 5045, whereby rotation angles of the joint portions 5033a to 5033c are controlled, and the driving of the arm portion 5031 is controlled. Thus, the position and the posture of the endoscope 5001 can be controlled. In this case, the arm controller 5045 can control the driving of the arm portion 5031 by various known control methods including force control or position control, etc.

For example, the surgeon 5067 may appropriately perform an operation input via the input device 5047 (including foot switch 5057) to appropriately control the driving of the arm portion 5031 by the arm control device 5045 in accordance with the operation input, thereby controlling the position and the posture of the endoscope 5001. With this control, after moving the endoscope 5001 of the distal end of the arm portion 5031 from an arbitrary position to an arbitrary position, it can be fixedly supported at a position after the movement. The arm portion 5031 may be operated by a so-called master-slave method. In this case, the arm portion 5031 can be remotely operated by the user via the input device 5047 installed at a position remote from a surgery room.

When the force control is applied, the arm control device 5045 may perform so-called power assist control in which the actuator of each of the joint portions 5033a to 5033c is driven to receive an external force from the user and move the arm portion 5031 smoothly in accordance with the external force. Thus, when the user moves the arm portion 5031 while touching the arm portion 5031 directly, it is possible to move the arm portion 5031 with a relatively light force. Accordingly, it becomes possible to move the endoscope 5001 more intuitively and with a simpler operation, thereby improving convenience of the user.

Here, in general, in the endoscopic surgery, the endoscope 5001 is supported by a physician called the scopist. In contrast, by using the support arm device 5027, it is possible to more reliably fix the position of the endoscope 5001 without manual intervention, and therefore, it is possible to stably obtain the image of the surgery part and smoothly perform the surgery.

The arm control device 5045 is not necessarily provided in the cart 5037. The arm controller 5045 may not necessarily be one device. For example, the arm control device 5045 may be provided in each of the joint portions 5033a to 5033c of the arm portion 5031 of the support arm device 5027, and the drive control of the arm portion 5031 may be realized by the plurality of arm control devices 5045 cooperating with each other.

(Light Source Device)

The light source device 5043 supplies the irradiation light to the endoscope 5001 when imaging the surgery part. The light source device 5043 is configured of a white light source including, for example, an LED, a laser light source, or a combination thereof. At this time, when the white light source is configured by a combination of RGB laser light sources, it is possible to control an output intensity and an output timing of each color (each wavelength) with high accuracy, and a white balance of the captured image in the light source device 5043 can be adjusted. Furthermore, in this case, by irradiating the laser beam from each RGB laser light source to the observation subject in time division and by controlling the driving of the image capture element of the camera head 5005 in synchronization with the irradiation timing, the image corresponding to each RGB may also be captured in time division. According to this method, a color image can be obtained without providing a color filter in the image capture element.

Furthermore, driving of the light source device 5043 may be controlled to change the intensity of the light to be output at predetermined time intervals. The image is acquired in time division by controlling the driving of the image capture element of the camera head 5005 in synchronization with the timing of the change in the intensity of the light, and is synthesized, it is possible to generate an image of a high dynamic range without so-called white skipping part and a black crushing part.

Furthermore, the light source device 5043 may be configured to be capable of supplying light of a predetermined wavelength band corresponding to the special light observation. In the special light observation, so-called narrow band light observation (Narrow Band Imaging) is performed in which, for example, a predetermined tissue such as a blood vessel of a mucosal surface layer is photographed with high contrasts by irradiating light in a narrow band compared to the irradiation light (that is, white light) in normal observation using the wavelength-dependence of light absorbed in the body tissues. Alternatively, in the special light observation, fluorescence observation for obtaining an image by fluorescence generated by irradiating excitation light may be performed. In the fluorescence observation, there may be performed, for example, by irradiating excitation light to the body tissues and observing fluorescence from the body tissues (autofluorescence observation), or by locally injecting a reagent such as indocyanine green (ICG) into the body tissues and irradiating excitation light corresponding to the fluorescence wavelength of the reagent to obtain a fluorescence image. The light source device 5043 may be configured to be capable of supplying narrowband light and/or excitation light corresponding to the special light observation.

(Camera Head and CCU)

Figure 19:
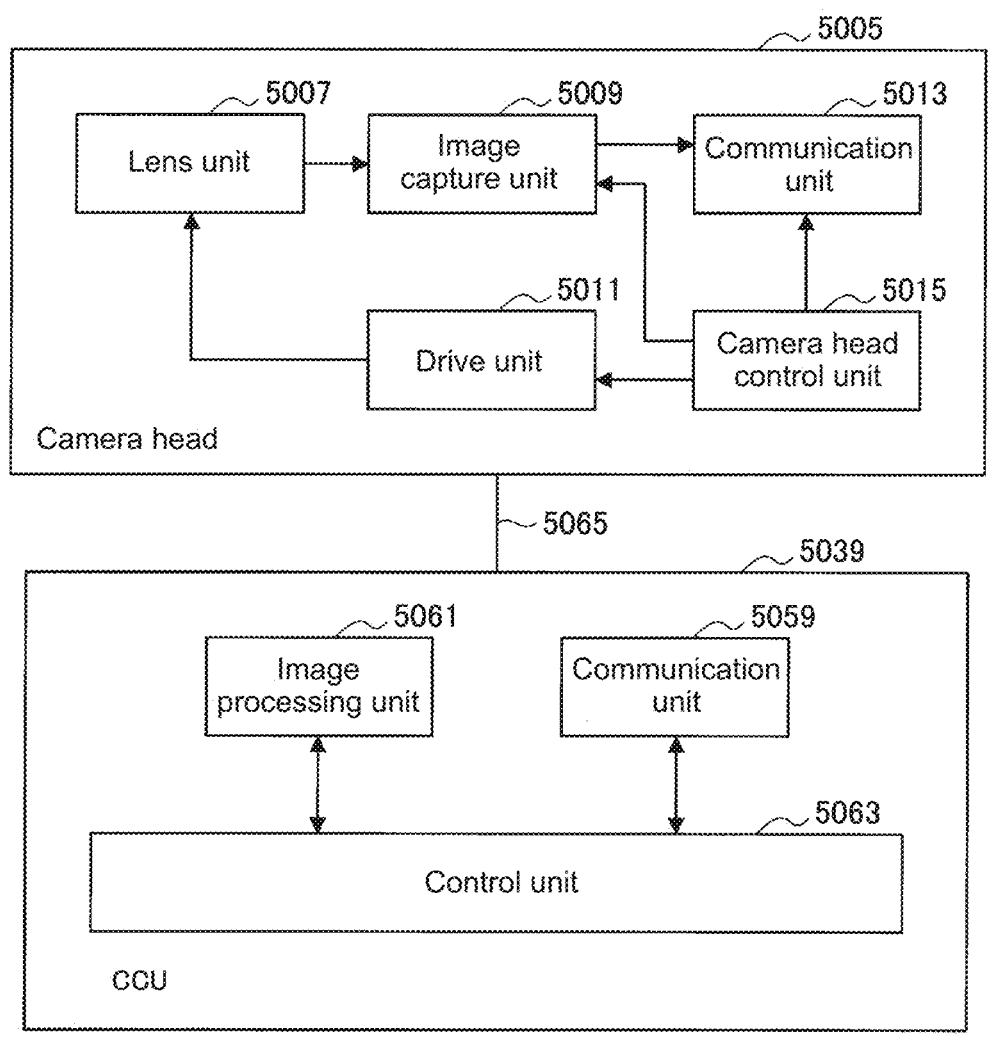
FIG. 19 is a block diagram showing an example of a functional configuration of a camera head and a CCU shown in FIG. 18.

Referring to FIG. 19, functions of the camera head 5005 and the CCU 5039 of the endoscope 5001 will be described in more detail. FIG. 19 is a block diagram showing an example of a functional configuration of the camera head 5005 and the CCU 5039 shown in FIG. 18.

Referring to FIG. 19, the camera head 5005 has, as its functions, a lens unit 5007, an image capture unit 5009, a drive unit 5011, a communication unit 5013, and a camera head control unit 5015. The CCU 5039 has, as its functions, a communication unit 5059, an image processing unit 5061, and a control unit 5063. The camera head 5005 and the CCU 5039 are bi-directionally communicatively connected by a transmission cable 5065.

First, the functional configuration of the camera head 5005 will be described. The lens unit 5007 is an optical system provided in a connection portion between the lens barrel 5003. Observation light taken from a distal end of the lens barrel 5003 is guided to the camera head 5005 enters the lens unit 5007. The lens unit 5007 is configured by combining a plurality of lenses including a zoom lens and a focus lens. Optical characteristics of the lens unit 5007 are adjusted, so as to condense the observation light on a light receiving surface of the image capture element of the image capture unit 5009. Furthermore, the zoom lens and the focal lens are configured to be movable on a position on the optical axis for adjustment of the magnification and the focus of the captured image.

The image capture unit 5009 includes the image capture element and is arranged at a subsequent stage of the lens unit 5007. The observation light passing through the lens unit 5007 is condensed on the light receiving surface of the image capture element, and an image signal corresponding to the observation image is generated by photoelectric conversion. The image signal generated by the image capture unit 5009 is provided to the communication unit 5013.

As the image capture element of the image capture unit 5009, for example, a CMOS (Complementary Metal Oxide Semiconductor) type image sensor capable of taking a color image having a Bayer array is used. As the image capture element, for example, a device capable of capturing a high-resolution image of 4K or more may be used. By obtaining the image of the surgery part with high resolution, the surgeon 5067 can grasp the state of the surgery part in more detail, and can smoothly proceed with the surgery.

Furthermore, the image capture element of the image capture unit 5009 is configured to have a pair of image capture elements for acquiring respective image signals for right-eye and left-eye corresponding to 3D display. By displaying 3D, the surgeon 5067 can more accurately grasp the depth of the living tissues in the surgeon part. Incidentally, when the image capture unit 5009 is constituted by a multi-plate type, corresponding to each image capture element, a plurality of systems of the lens units 5007 is also provided.

Furthermore, the image capture unit 5009 may not necessarily be provided in the camera head 5005. For example, the image capture unit 5009 may be provided inside the lens barrel 5003 immediately after the objective lens.

The driving unit 5011 is constituted by an actuator and moves the zoom lens and the focus lens of the lens unit 5007 by a predetermined distance along the optical axis by control from the camera head control unit 5015. As a result, the magnification and the focus of the captured image by the image capture unit 5009 can be appropriately adjusted.

The communication unit 5013 is configured by a communication device for transmitting and receiving various types of data to and from the CCU 5039. The communications unit 5013 transmits the image signal obtained from the image capture unit 5009 to the CCU 5039 via the transmission cable 5065 as the RAW data. At this time, it is preferable that the image signal is transmitted by optical communication in order to display the captured image of the surgery part with low latency. This is because, at the time of the surgery, the surgeon 5067 performs the surgery while observing the state of the affected part by the captured image, and therefore, for safer and more reliable surgery, it is required that the moving image of the surgery part be displayed in real time as much as possible. When the optical communication is performed, the communication unit 5013 is provide with a photoelectric conversion module for converting the electrical signal into the optical signal. After the image signal is converted into an optical signal by the photoelectric conversion module, the image signal is transmitted to the CCU 5039 via the transmission cable 5065.

Furthermore, the communication unit 5013 receives the control signal for controlling driving of the camera head 5005 from the CCU 5039. The control signal includes, for example, information for specifying a frame rate of the captured image, information for specifying an exposure value at the time of capturing the image, and/or information for specifying the magnification and the focus of the captured image. The communication unit 5013 provides the received control signal to the camera head control unit 5015. Incidentally, the control signal from the CCU 5039 may also be transmitted by the optical communication. In this case, the communication unit 5013 is provided with the photoelectric conversion module for converting the optical signal into the electrical signal, and the control signal is converted into the electrical signal by the photoelectric conversion module and is provided to the camera head control unit 5015.

Incidentally, the above-described capturing conditions such as the frame rate, the exposure value, the magnification, and the focus are automatically set by the control unit 5063 of the CCU 5039 based on the acquired image signal. That is, so-called an AE (Auto Exposure) function, an AF (Auto Focus) function, and an AWB (Auto White Balance) function are mounted on the endoscope 5001.

The camera head control unit 5015 controls the driving of the camera head 5005 based on the control signal from the CCU 5039 received via the communication unit 5013. For example, the camera head control unit 5015 controls the driving of the image capture element of the image capture unit 5009 based on information to specify the frame rate of the captured image and/or information to specify exposure at the time of image capturing. Furthermore, for example, the camera head control unit 5015 appropriately moves the zoom lens and the focal lens of the lens unit 5007 via the driving unit 5011 based on information to specify the magnification and the focus of the captured image. The camera head control unit 5015 may further include a function of storing information for identifying the lens barrel 5003 and the camera head 5005.

Note that by arranging the configurations of the lens unit 5007, the image capture unit 5009, and the like in a hermetically sealed structure having high airtightness and waterproofness, the camera head 5005 can be made resistant to autoclave sterilization processing.

Next, a functional configuration of the CCU 5039 will be described. The communication unit 5059 is configured by a communication device for transmitting and receiving various types of information to and from the camera head 5005. The communication unit 5059 receives the image signal transmitted from the camera head 5005 via the transmission cable 5065. At this time, as described above, the image signal can be suitably transmitted by the optical communication. In this case, corresponding to the optical communication, the communication unit 5059 is provided with the photoelectric conversion module for converting the optical signal into the electrical signal. The communications unit 5059 provides the image signal converted into the electrical signal to the image processing unit 5061.

Furthermore, the communication unit 5059 transmits the control signal for controlling the driving of the camera head 5005 to the camera head 5005. The control signal may also be transmitted by the optical communication.

The image processing unit 5061 performs various image processing on the image signal that is the RAW data transmitted from the camera head 5005. The image processing includes, for example, various known signal processing such as the development processing, image quality enhancement processing (band enhancement processing, super-resolution processing, NR (Noise reduction) processing, and/or camera shake correction processing), and/or enlargement processing (electronic zooming processing). Furthermore, the image processing unit 5061 performs detection processing on the image signal for performing AE, AF, and AWB.

The image processing unit 5061 is configured by a processor such as the CPU and the GPU, and when the processor operates in accordance with the predetermined program, the above-described image processing or the detection processing can be performed. When the image processing unit 5061 is configured by a plurality of GPUs, the image processing unit 5061 divides information about the image signal as appropriate, and performs the image processing in parallel by the plurality of GPUs.

The control unit 5063 performs various controls relating to capturing the image of the surgery part by the endoscope 5001 and display of the captured image. For example, the control unit 5063 generates the control signal for controlling the driving of the camera head 5005. At this time, when the capturing conditions are input by the user, the control unit 5063 generates the control signal based on the input by the user. Alternatively, when the endoscope 5001 has an AE function, an AF function, and an AWB function, the control unit 5063 appropriately calculates an optimal exposure value, a focal length, and a white balance in accordance with a result of the detection processing by the image processing unit 5061, and generates the control signal.

Furthermore, the control unit 5063 displays the image of the surgery part on the display device 5041 based on the image signal that is subjected to the image processing by the image processing unit 5061. At this time, the control unit 5063 recognizes various objects in an image of the surgery 5063 using various image recognition techniques. For example, by detecting the shape, color, and the like of each edge of the objects included in the image of the surgery part, the control unit 5063 can recognize an operative tool such as the forceps, a specific biological site, a hemorrhage, a mist when the energy treatment tool 5021 is used, and the like. When displaying the image of the surgery part on the display device 5041, the control unit 5063 superimposes and displays various types of surgery support information about the image of the surgery part using a recognition result. By superimposing and displaying the operation support information and presenting it to the surgeon 5067, it is possible to proceed with the surgery more safely and reliably.

The transmission cable 5065 for connecting the camera head 5005 and the CCU 5039 is an electric signal cable corresponding to communication by the electric signal, an optical fiber corresponding to the optical communication, or a composite cable thereof.

Here, in the example shown, the communication is made wirelessly using the transmission cable 5065, but the communication between the camera head 5005 and the CCU 5039 may be performed wirelessly. When the communication between the two is performed wirelessly, it is not necessary to lay the transmission cable 5065 in the surgery room, so that a situation in which movements of medical staffs in the surgery room is obstructed by the transmission cable 5065 can be eliminated.

An example of the endoscopic surgery system 5000 to which the technology according to the present disclosure may be applied is described above. Note that, although the endoscopic surgery system 5000 is described as an example here, a system to which the technology according to the present disclosure can be applied is not limited to such an example. For example, the technology of the present disclosure may be applied to a test flexible endoscopic system or a microscope surgery system.

The technology according to the present disclosure is suitably applied to the endoscope 5001, the CCU 5039, the display device 5041, and the like among the configurations described above. For example, the image sensor mounted on the endoscope 5001 functions as the image sensor 11 described with reference to FIG. 1. The image processing unit 5061 of the CCU 5039 functions as the video processing unit 13 described with reference to FIG. 1. The display device 5041 is the display device 15 described with reference to FIG. 1. By applying the technology according to the present disclosure to the endoscope 5001, the CCU 5039, the display device 5041, and the like, the visibility of the peaking display displayed on the display device 5041 can be improved. As a result, a focus adjustment at the time of the surgery can be easily realized, and a safe and highly reliable surgery can be performed.

For example, the technology according to the present disclosure may be applied to a surgery room system.

Figure 20:
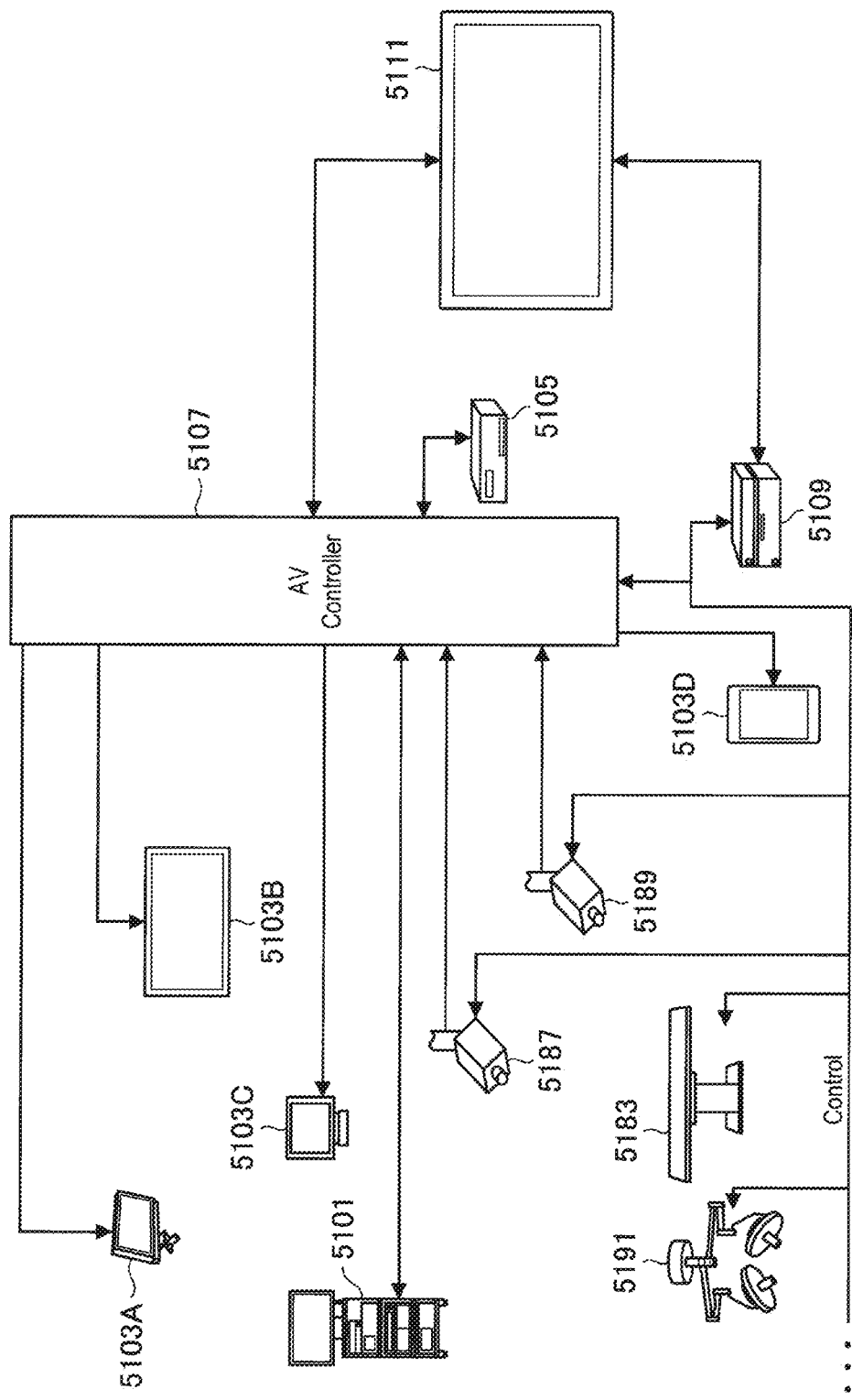
FIG. 20 is a diagram schematically showing an overall configuration of a surgery room system.

FIG. 20 is a diagram schematically showing an overall configuration of a surgery room system 5100 to which technology according to the present disclosure may be applied. Referring to FIG. 20, the surgery room system 5100 is configured such that device groups installed in the surgery room are connected to each other in a coordinated manner via an audio-visual controller (AV Controller) 5107 and a surgery room controller 5109.

Various devices may be installed in the surgery room. FIG. 20 shows, as examples, various devices group 5101 for the endoscopic surgery, a ceiling camera 5187 provided on a ceiling of the surgery room for capturing an image of the surgeon's hand, an surgical field camera 5189 provided on the ceiling of the surgery room for capturing an image of the entire surgery room, a plurality of display devices 5103A to 5103D, a recorder 5105, a patient bed 5183, and lighting 5191.

Among these devices, the devices group 5101 belongs to an endoscopic surgery system 5113 described later, and includes an endoscope, a display device for displaying an image captured by the endoscope, and the like. Each device belonging to the endoscopic surgery system 5113 is also referred to as a medical device. On the other hand, the display devices 5103A to 5103D, the recorder 5105, the patient bed 5183, and the lighting 5191 are devices provided separately from the endoscopic surgery system 5113, for example, in the surgery room. Each device that does not belong to these endoscopic surgery systems 5113 is also referred to as a non-medical device. The audio-visual controller 5107 and/or the surgery room controller 5109 cooperatively control the operation of the medical devices and the non-medical devices.

The audio-visual controller 5107 collectively controls processing relating to the image display in the medical devices and the non-medical devices. Specifically, among the devices included in the surgery room system 5100, the devices group 5101, the ceiling camera 5187, and the surgical field camera 5189 may be devices (hereinafter, also referred to as source devices) having a function of transmitting information (hereinafter, also referred to as display information) to be displayed during the surgery. Each of the display devices 5103A to 5103D may be a device to which the display information is output (hereinafter, also referred to as output device). The recorder 5105 may be a device corresponding to both the source device and the output device. The audio-visual controller 5107 has a function of controlling the operations of the source device and the output device, acquiring the display information from the source device, and transmitting the display information to the output device to display or record the display information. Note that the display information is various images taken during the surgery, various information about the surgery (e.g., patient's body information, past examination results, information about surgical procedure, etc.), and the like.

Specifically, the audiovisual controller 5107 can transmit, as the display information, information about the image of the surgery part in the body cavity of the patient captured by the endoscope from the devices group 5101. Also, information about an image of hands of the surgeon captured by the ceiling camera 5187 may be transmitted from the ceiling camera 5187 as the display information. In addition, as the display information, information about an image indicating the entire state of the surgery room captured by the surgical field camera 5189 can be transmitted from the surgical field camera 5189. When there is other device having a capturing function in the surgery room system 5100, the audiovisual controller 5107 may acquire information about an image captured by the other device as the display information from the other device.

Alternatively, for example, information about these images captured in the past is recorded in the recorder 5105 by the audio-visual controller 5107. The audiovisual controller 5107 can acquire information about the images captured in the past from the recorder 5105 as the display information. The recorder 5105 may also record various types of information related to the surgery in advance.

The audiovisual controller 5107 displays the acquired display information (i.e., images captured during surgery and various types of information about surgery) on at least one of the display devices 5103A to 5103D as the output devices. In the example shown in the drawing, the display device 5103A is a display device installed suspended from the ceiling of the surgery room, the display device 5103B is a display device installed on the wall surface of the surgery room, the display device 5103C is a display device installed on a desk in the surgery room, and the display device 5103D is a mobile device (for example, a tablet PC (Personal Computer)) having a display function.

Although not shown in FIG. 20, the surgery room system 5100 may include devices external to the surgery room. The devices external to the surgery room may be, for example, a server connected to a network built in or outside a hospital, PCs used by the medical staffs, a projector installed in a conference room of the hospital, or the like. When the external devices are outside the hospital, the audio-visual controller 5107 can also cause the display information to be displayed on a display device of another hospital via a videoconference system or the like for telemedicine.

The surgery room control device 5109 collectively controls processing other than the processing relating to the image display in the non-medical devices. For example, the surgery room controller 5109 controls driving of the patient bed 5183, the ceiling camera 5187, the surgical field camera 5189, and the lighting 5191.

The surgery room system 5100 is provided with a centralized operation panel 5111, and the user can give an instruction for the image display to the audiovisual controller 5107 or give an instruction for operation of the non-medical device to the surgery room control device 5109 via the centralized operation panel 5111. The centralized operation panel 5111 is configured by a touch panel provided on the display surface of the display device.

Figure 21:
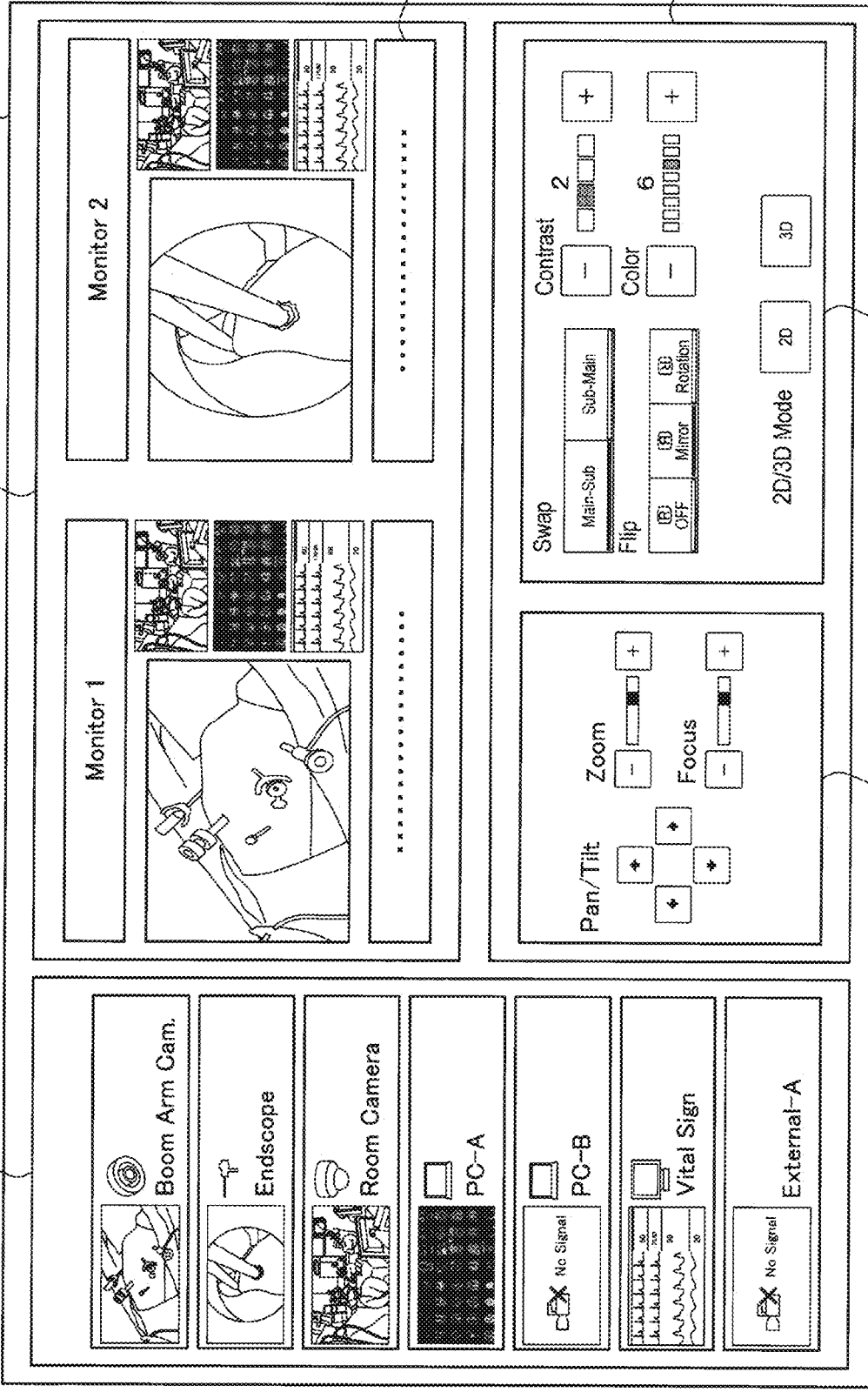
FIG. 21 is a diagram showing a display example of an operation screen on a centralized operation panel.

FIG. 21 is a diagram showing a display example of an operation screen on the centralized operation panel 5111. FIG. 21 shows, as an example, an operation screen corresponding to a case in which two display devices are provided as the output devices in the surgery room system 5100. Referring to FIG. 21, the operation screen 5193 includes a source selection area 5195, a preview area 5197, and a control area 5201.

In the source selection area 5195, the source device provided in the surgery room system 5100 and a thumbnail screen representing the display information included in the source device are displayed in association with each other. The user can select the display information to be displayed on the display device from any of the source devices displayed in the source selection area 5195.

The preview area 5197 displays previews of the screen displayed on the two display devices (Monitor 1, Monitor 2) that are the output devices. In the example shown, four images are PinP displayed on one display device. The four images correspond to the display information transmitted from the source device selected in the source selection area 5195. Of the four images, one is displayed relatively large as a main image and the remaining three are displayed relatively small as sub images. The user can swap the main image and the sub image by appropriately selecting the region where the four images are displayed. In addition, a status display area 5199 is provided below the area in which the four images are displayed, and a status related to the surgery (e.g., elapsed time of surgery, body information of patient, etc.) can be appropriately displayed in the area.

The control area 5201 includes a source operation area 5203 on which GUI (Graphical User Interface) components for operating the source device are displayed and an output operation area 5205 on which GUI components for operating the output device is displayed. In the example shown, the source operation area 5203 includes the GUI components for performing various operations (pan, tilt, and zoom) to the camera in the source device having the capturing function. The user can manipulate the operation of the camera in the source device by appropriately selecting these GUI components. Although not shown, in a case where the source device selected in the source selection area 5195 is the recorder (i.e., in a case where image recorded on recorder in the past is displayed on preview area 5197), the source operation area 5203 may be provided with GUI components for performing operations such as playback, playback stop, rewind, and fast-forward of the image.

Furthermore, the output operation area 5205 is provided with GUI components for performing various operations for the display in the display device which is the output device (swap, flip, color adjustment, contrast adjustment, switching between 2D display and 3D display). The user can operate the display on the display device by appropriately selecting these GUI components.

Note that the operation screen displayed on the centralized operation panel 5111 is not limited to the example shown in the drawing, and the user may be able to input an operation to each device that can be controlled by the audiovisual controller 5107 and the surgery room control device 5109 provided in the surgery room system 5100 via the centralized operation panel 5111.

Figure 22:
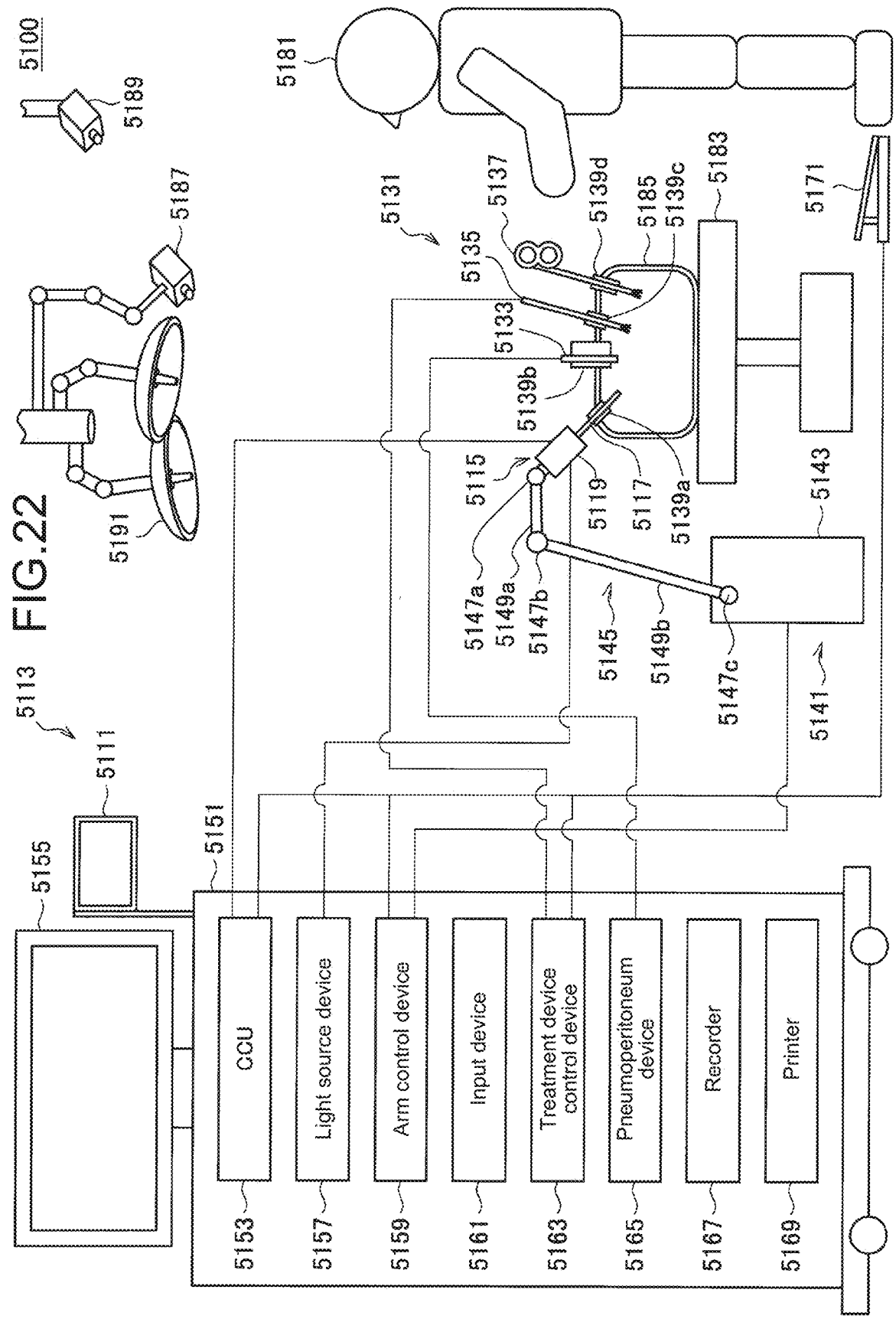
FIG. 22 is a diagram showing an example of a state of surgery to which the surgery room system is applied.

FIG. 22 is a diagram showing an example of a state of the surgery to which the surgery room system described above is applied. The ceiling camera 5187 and the surgical field camera 5189 are provided on the ceiling of the surgery room, and are capable of imaging the hands of the surgeon (doctor) 5181 who performs the treatment on the affected part of a patient 5185 on the patient bed 5183 and the state of the entire surgery room. The ceiling camera 5187 and the surgical field camera 5189 may be provided with a magnification adjustment function, a focal length adjustment function, a imaging direction adjustment function, or the like. The lighting 5191 is provided on the ceiling of the surgery room, and irradiates at least the hand of the surgeon 5181. The lighting 5191 may be capable of appropriately adjusting an amount of irradiation light, a wavelength (color) of the irradiation light, a direction of the irradiation light, and the like.

As shown in FIG. 20, the endoscopic surgery system 5113, the patient bed 5183, the ceiling camera 5187, the surgical field camera 5189, and the lighting 5191 are cooperatively connected to each other via the audiovisual control apparatus 5107 and the surgery room controller 5109 (not shown in FIG. 22). The centralized operation panel 5111 is provided in the surgery room, and as described above, the user can appropriately operate these devices existing in the surgery room via the centralized operation panel 5111.

Hereinafter, the configuration of the endoscopic surgery system 5113 will be described in detail. As shown, the endoscopic surgery system 5113 includes an endoscope 5115, other surgical tools 5131, a support arm device 5141 for supporting the endoscope 5115, and a cart 5151 on which various devices for the endoscopic surgery are mounted.

In endoscopic surgery, instead of incising the abdominal wall, a plurality of cylindrical opening tools called trockers 5139*a* to 5139*d* is inserted into the abdominal wall. Then, a lens barrel 5117 of the endoscope 5115 and other surgical tools 5131 are inserted into the body cavity of the patient 5185 from the trockers 5139*a* to 5139*d*. In the example shown, as the other surgical tools 5131, the pneumoperitoneum tube 5133, the energy treatment tool 5135, and the forceps 5137 are inserted into the body cavity of the patient 5185. The energy treatment tool 5135 is a treatment tool for performing incision and peeling of tissue, sealing of blood vessels, or the like by high-frequency current or ultrasonic vibration. However, the surgical tools 5131 shown in the drawing is merely an example, and various surgical tools generally used in the endoscopic surgery such as the tweezer and the retractor may be used as the surgical tools 5131.

An image of the surgery part in the body cavity of the patient 5185 imaged by the endoscope 5115 is displayed on the display device 5155. The surgeon 5181 uses the energy treatment tool 5135 and the forceps 5137 to perform the treatment such as, for example, resection of the affected part while viewing the image of the surgery part displayed on the display device 5155 in real time. Although not shown, the pneumoperitoneum tube 5133, the energy treatment tool 5135, and the forceps 5137 are supported by the surgeon 5181, the assistant, or the like during the surgery.

(Support Arm Device)

The support arm device 5141 includes an arm portion 5145 extending from the base portion 5143. In the example shown, the arm portion 5145 includes joint portions 5147*a*, 5147*b*, and 5147*c*, and links 5149*a* and 5149*b*, and is driven under the control of the arm control device 5159. The endoscope 5115 is supported by the arm portion 5145, and its position and posture are controlled. Thus, fixation of the stable position of the endoscope 5115 can be realized.

(Endoscope)

The endoscope 5115 includes the lens barrel 5117 in which a region of a predetermined length from a distal end is inserted into the body cavity of the patient 5185, and a camera head 5119 connected to a base end of the lens barrel 5117. In the example shown, the endoscope 5115 configured as the so-called rigid scope having a rigid lens barrel 5117 is shown, but the endoscope 5115 may be configured as the so-called flexible scope having a flexible lens barrel 5117.

The distal end of the lens barrel 5117 is provide with an opening in which the objective lens is fitted. A light source device 5157 is connected to the endoscope 5115, and light generated by the light source device 5157 is guided to the distal end of the barrel by a light guide extending inside the barrel 5117, and is irradiated toward the observation target in the body cavity of the patient 5185 via the objective lens. Note that the endoscope 5115 may be a direct scope, a perspective view scope or a side scope.

Inside the camera head 5119, the optical system and the image capture element are provided, and the reflected light from the observation subject (observation light) is focused on the image capture element by the optical system. The observation light is photoelectrically converted by the image capture element, the electrical signal corresponding to the observation light, i.e. the image signal corresponding to the observation image is generated. The image signal is transmitted to the camera control unit (CCU: Camera Control Unit) 5153 as the RAW data. Incidentally, the camera head 5119 has a function of adjusting the magnification and the focal length by appropriately driving the optical system.

Note that the plurality of image capture elements may be provided in the camera head 5119 in order to cope with, for example, the stereoscopic vision (3D display) or the like. In this case, inside the barrel 5117, in order to guide the observation light to each of the plurality of image capture elements, the plurality of the relay optical systems is provided.

(Various Devices Mounted on Cart)

The CCU 5153 includes the CPU (Central Processing Unit), the GPU (Graphics Processing Unit), and the like, and collectively controls the operations of the endoscopes 5115 and the display device 5155. Specifically, the CCU 5153 performs various image processing for displaying the image based on the image signal such as, for example, the development processing (demosaicing processing), on the image signal received from the camera head 5119. The CCU 5153 provides the image signal to which the image processing is applied to the display device 5155. The CCU 5153 is connected to the audio-visual controller 5107 shown in FIG. 20. The CCU 5153 also provides the image signal to which the image processing is applied to the audiovisual controller 5107. The CCU 5153 also transmits the control signal to the camera head 5119 and controls driving thereof. Such control signal may include information about the capturing conditions such as the magnification and the focal length. The information about the capturing conditions may be input via the input device 5161 or may be input via the above-described centralized operation panel 5111.

The display device 5155, by the control from the CCU 5153, displays the image based on the image signal to which the image processing is applied by the CCU 5153. When the endoscope 5115 is compatible with high-resolution imaging such as 4K (number of horizontal pixels 3840×number of vertical pixels 2160) or 8K (number of horizontal pixels 7680×number of vertical pixels 4320) and/or is compatible with 3D display, the display device 5155 capable of high-resolution display and/or capable of 3D display corresponding thereto can be used. In the case of the display device is compatible with the high-resolution imaging such as 4K or 8K, a more immersive feeling can be obtained by using the display device having a size of 55 inches or more as the display device 5155. In addition, a plurality of display devices 50155 having different resolutions and sizes may be provided depending on the applications.

The light source device 5157 is configured of a light source such as the LED (light emitting diode), for example, and supplies the irradiation light to the endoscope 5115 at the time of imaging the surgery part.

The arm control device 5159 is configured of a processor such as the CPU, for example, and operates in accordance with the predetermined program to control driving of the arm portion 5145 of the support arm device 5141 in accordance with a predetermined control method.

An input device 5161 is an input interface to the endoscopic surgery system 5113. The user can input various types of information and instructions to the endoscopic surgery system 5113 via the input device 5161. For example, the user inputs various types of information about the surgery such as the body information of the patient and information about the surgical procedure, via the input device 5161. In addition, for example, the user inputs an instruction to drive the arm portion 5145, an instruction to change capturing conditions (type, magnification, focal length, etc.) of the endoscope 5115, an instruction to drive the energy treatment tool 5021, and the like via the input device 5135.

The type of the input device 5161 is not limited, and the input device 5161 may be any of various known input devices. As the input device 5161, for example, the mouse, the keyboard, the touch panel, the switch, the foot switch 5057, the lever, or the like can be used. When the touch panel is used as the input device 5155, the touch panel may be provided on a display surface of the display device 5161.

Alternately, the input device 5161 is a device that is mounted by the user such as the wearable device or the HMD (Head Mounted Display) of the glass type, and various inputs are made according to the gesture or the line of sight of the user detected by the device. The input device 5161 also includes the camera capable of detecting the movement of the user, and various inputs are made according to the gesture or the line of sight of the user detected from the image captured by the camera. Furthermore, the input device 5161 includes the microphone capable of picking up the voice of the user, and various inputs are made by the voice through the microphone. In this manner, by configuring the input device 5161 so as to be able to input various types of information without contact, it is possible for the user belonging to the particularly clean area (for example, surgeon 5181) to operate the device belonging to the dirty area without contact. In addition, the user can operate the device without releasing his or her hand from the device, thereby improving the convenience of the user.

The treatment device control device 5163 controls driving of the energy treatment device 5135 for cauterization of tissues, incision or sealing of blood vessels, and the like. The pneumoperitoneum device 5165 delivers gas into the body cavity of the patient 5185 through the pneumoperitoneum tube 5133 in order to inflate the body cavity for the purpose of securing the field of view by the endoscope 5115 and securing the working space of the surgeon. A recorder 5167 is a device capable of recording various types of information about the surgery. A printer 5165 is a device capable of printing various types of information about the surgery in various formats such as text, images and graphs.

Hereinafter, a configuration particularly characteristic of the endoscopic surgery system 5113 will be described in more detail.

(Support Arm Device)

The support arm device 5141 includes a base portion 5143 serving as a base and an arm portion 5145 extending from the base portion 5143. In the example shown, the arm portion 5145 includes a plurality of joint portions 5147a, 5147b, 5147c, and a plurality of links 5149a, 5149b connected by the joint portion 5147b, but in FIG. 22, the configuration of the arm portion 5145 is shown in a simplified manner for simplicity. Actually, the shapes, the number, and the arrangement of the joint portions 5147a to 5147c and the links 5149a and 5149b, directions of rotation axes of the joint portions 5147a to 5147c, and the like can be appropriately set so that the arm portion 5145 has a desired degree of freedom. For example, the arm portion 5031 may be suitably configured to have six or more degrees of freedom. Thus, since it becomes possible to freely move the endoscope 5115 within a movable range of the arm portion 5145, it is possible to insert the lens barrel 5117 of the endoscope 5115 into the body cavity of the patient 5185 from a desired direction.

The joint portions 5147a to 5147c are provided with actuators, and the joint portions 5147a to 5147c are configured to be rotatable around predetermined rotation axes by driving the actuators. The driving of the actuators is controlled by the arm control device 5159, whereby rotation angles of the joint portions 5147a to 5147c are controlled, and the driving of the arm portion 5145 is controlled. Thus, the position and the posture of the endoscope 5115 can be controlled. In this case, the arm controller 5159 can control the driving of the arm portion 5145 by various known control methods including the force control, the position control, etc.

For example, the surgeon 5181 may appropriately perform the operation input via the input device 5161 (including foot switch 5171) to appropriately control the driving of the arm portion 5145 by the arm control device 5159 in accordance with the operation input, thereby controlling the position and the posture of the endoscope 5115. With this control, after moving the endoscope 5115 of the distal end of the arm portion 5145 from an arbitrary position to an arbitrary position, it can be fixedly supported at a position after the movement. The arm portion 5145 may be operated by the so-called master-slave method. In this case, the arm portion 5145 can be remotely operated by the user via the input device 5161 installed at a position remote from the surgery room.

When the force control is applied, the arm control device 5159 may perform the so-called power assist control in which the actuator of each of the joint portions 5147a to 5147c is driven to receive an external force from the user and move the arm portion 5145 smoothly in accordance with the external force. Thus, when the user moves the arm portion 5145 while touching the arm portion 5145 directly, it is possible to move the arm portion 5145 with a relatively light force. Accordingly, it becomes possible to move the endoscope 5115 more intuitively and with a simpler operation, thereby improving convenience of the user.

Here, in general, in the endoscopic surgery, the endoscope 5115 is supported by the physician called the scopist. In contrast, by using the support arm device 5141, it is possible to more reliably fix the position of the endoscope 5115 without manual intervention, and therefore, it is possible to stably obtain the image of the surgery part and smoothly perform the surgery.

The arm control device 5159 is not necessarily provided in the cart 5151. The arm controller 5159 may not necessarily be one device. For example, the arm control device 5159 may be provided in each of the joint portions 5147a to 5147c of the arm portion 5145 of the support arm device 5141, and the drive control of the arm portion 5145 may be realized by the plurality of arm control devices 5159 cooperating with each other.

(Light Source Device)

The light source device 5157 supplies the irradiation light to the endoscope 5115 when imaging the surgery part. The light source device 5157 is configured of the white light source including, for example, the LED, the laser light source, or a combination thereof. At this time, when the white light source is configured by a combination of the RGB laser light sources, it is possible to control the output intensity and the output timing of each color (each wavelength) with high accuracy, and the white balance of the captured image in the light source device 5157 can be adjusted. Furthermore, in this case, by irradiating the laser beam from each RGB laser light source to the observation subject in time division and by controlling the driving of the image capture element of the camera head 5119 in synchronization with the irradiation timing, the image corresponding to each RGB may also be captured in time division. According to this method, the color image can be obtained without providing the color filter in the image capture element.

Furthermore, driving of the light source device 5157 may be controlled to change the intensity of the light to be output at predetermined time intervals. The image is acquired in time division by controlling the driving of the image capture element of the camera head 5119 in synchronization with the timing of the change in the intensity of the light, and is synthesized, it is possible to generate the image of the high dynamic range without the so-called white skipping part and the black crushing part.

Furthermore, the light source device 5157 may be configured to be capable of supplying the light of the predetermined wavelength band corresponding to the special light observation. In the special light observation, the so-called narrow band light observation (Narrow Band Imaging) is performed in which, for example, the predetermined tissue such as the blood vessel of the mucosal surface layer is photographed with high contrasts by the irradiating light in the narrow band compared to the irradiation light (that is, white light) in the normal observation using the wavelength-dependence of light absorbed in the body tissues. Alternatively, in the special light observation, the fluorescence observation for obtaining the image by fluorescence generated by irradiating the excitation light may be performed. In the fluorescence observation, there may be performed, for example, by irradiating the excitation light to the body tissues and observing fluorescence from the body tissues (autofluorescence observation), or by locally injecting the reagent such as the indocyanine green (ICG) into the body tissues and irradiating the excitation light corresponding to the fluorescence wavelength of the reagent to obtain the fluorescence image. The light source device 5157 may be configured to be capable of supplying the narrowband light and/or the excitation light corresponding to the special light observation.

(Camera Head and CCU)

Figure 23:
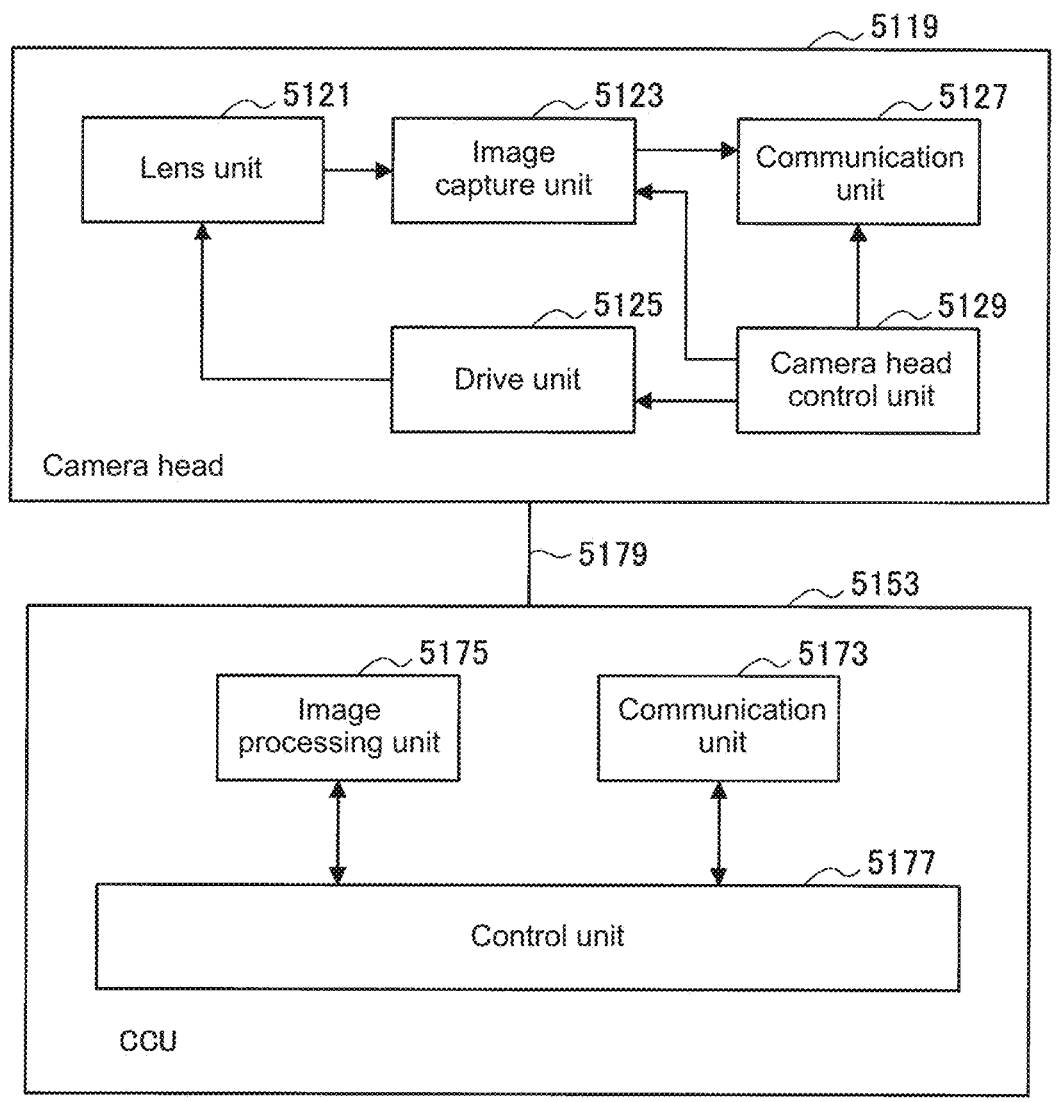
FIG. 23 is a block diagram showing an example of a functional configuration of a camera head and a CCU shown in FIG. 22.

Referring to FIG. 23, functions of the camera head 5119 and the CCU 5153 of the endoscope 5115 will be described in more detail. FIG. 23 is a block diagram showing an example of a functional configuration of the camera head 5119 and the CCU 5153 shown in FIG. 22.

Referring to FIG. 23, the camera head 5119 has, as its functions, a lens unit 5121, an image capture unit 5123, a drive unit 5125, a communication unit 5127, and a camera head control unit 5129. The CCU 5153 has, as its functions, a communication unit 5173, an image processing unit 5175, and a control unit 5177. The camera head 5119 and the CCU 5153 are bi-directionally communicatively connected by a transmission cable 5179.

First, the functional configuration of the camera head 5119 will be described. The lens unit 5121 is an optical system provided in a connection portion between the lens barrel 5117. Observation light taken from a distal end of the lens barrel 5117 is guided to the camera head 5119 enters the lens unit 5121. The lens unit 5121 is configured by combining the plurality of lenses including the zoom lens and the focus lens. Optical characteristics of the lens unit 5121 are adjusted, so as to condense the observation light on a light receiving surface of the image capture element of the image capture unit 5123. Furthermore, the zoom lens and the focal lens are configured to be movable on a position on the optical axis for adjustment of the magnification and the focus of the captured image.

The image capture unit 5123 includes the image capture element and is arranged at a subsequent stage of the lens unit 5121. The observation light passing through the lens unit 5121 is condensed on the light receiving surface of the image capture element, and an image signal corresponding to the observation image is generated by photoelectric conversion. The image signal generated by the image capture unit 5123 is provided to the communication unit 5127.

As the image capture element of the image capture unit 5123, for example, the CMOS (Complementary Metal Oxide Semiconductor) type image sensor capable of taking the color image having the Bayer array is used. As the image capture element, for example, the device capable of capturing the high-resolution image of 4K or more may be used. By obtaining the image of the surgery part with high resolution, the surgeon 5181 can grasp the state of the surgery part in more detail, and can smoothly proceed with the surgery.

Furthermore, the image capture element of the image capture unit 5123 is configured to have a pair of image capture elements for acquiring respective image signals for right-eye and left-eye corresponding to 3D display. By displaying 3D, the surgeon 5181 can more accurately grasp the depth of the living tissues in the surgeon part. Incidentally, when the image capture unit 5123 is constituted by the multi-plate type, corresponding to each image capture element, a plurality of systems of the lens units 5121 is also provided.

Furthermore, the image capture unit 5123 may not necessarily be provided in the camera head 5119. For example, the image capture unit 5123 may be provided inside the lens barrel 5117 immediately after the objective lens.

The driving unit 5011 is constituted by the actuator and moves the zoom lens and the focus lens of the lens unit 5121 by a predetermined distance along the optical axis by control from the camera head control unit 5129. As a result, the magnification and the focus of the captured image by the image capture unit 5123 can be appropriately adjusted.

The communication unit 5127 is configured by the communication device for transmitting and receiving various types of data to and from the CCU 5153. The communications unit 5127 transmits the image signal obtained from the image capture unit 5123 to the CCU 5153 via the transmission cable 5179 as the RAW data. At this time, it is preferable that the image signal is transmitted by optical communication in order to display the captured image of the surgery part with low latency. This is because, at the time of the surgery, the surgeon 5181 performs the surgery while observing the state of the affected part by the captured image, and therefore, for safer and more reliable surgery, it is required that the moving image of the surgery part be displayed in real time as much as possible. When the optical communication is performed, the communication unit 5127 is provide with a photoelectric conversion module for converting the electrical signal into the optical signal. After the image signal is converted into the optical signal by the photoelectric conversion module, the image signal is transmitted to the CCU 5153 via the transmission cable 5179.

Furthermore, the communication unit 5127 receives the control signal for controlling the driving of the camera head 5119 from the CCU 5153. The control signal includes, for example, information for specifying the frame rate of the captured image, information for specifying the exposure value at the time of capturing the image, and/or information for specifying the magnification and the focus of the captured image. The communication unit 5127 provides the received control signal to the camera head control unit 5129. Incidentally, the control signal from the CCU 5153 may also be transmitted by the optical communication. In this case, the communication unit 5127 is provided with the photoelectric conversion module for converting the optical signal into the electrical signal, and the control signal is converted into the electrical signal by the photoelectric conversion module and is provided to the camera head control unit 5129.

Incidentally, the above-described capturing conditions such as the frame rate, the exposure value, the magnification, and the focus are automatically set by the control unit 5177 of the CCU 5153 based on the acquired image signal. That is, so-called the AE (Auto Exposure) function, the AF (Auto Focus) function, and the AWB (Auto White Balance) function are mounted on the endoscope 5115.

The camera head control unit 5129 controls the driving of the camera head 5119 based on the control signal from the CCU 5153 received via the communication unit 5127. For example, the camera head control unit 5129 controls the driving of the image capture element of the image capture unit 5123 based on information to specify the frame rate of the captured image and/or information to specify exposure at the time of image capturing. Furthermore, for example, the camera head control unit 5129 appropriately moves the zoom lens and the focal lens of the lens unit 5121 via the driving unit 5125 based on information to specify the magnification and the focus of the captured image. The camera head control unit 5129 may further include a function of storing information for identifying the lens barrel 5117 and the camera head 5119.

Note that by arranging the configurations of the lens unit 5121, the image capture unit 5123, and the like in a hermetically sealed structure having high airtightness and waterproofness, the camera head 5119 can be made resistant to autoclave sterilization processing.

Next, a functional configuration of the CCU 5153 will be described. The communication unit 5153 is configured by a communication device for transmitting and receiving various types of information to and from the camera head 5119. The communication unit 5173 receives the image signal transmitted from the camera head 5119 via the transmission cable 5179. At this time, as described above, the image signal can be suitably transmitted by the optical communication. In this case, corresponding to the optical communication, the communication unit 5173 is provided with the photoelectric conversion module for converting the optical signal into the electrical signal. The communications unit 5173 provides the image signal converted into the electrical signal to the image processing unit 5175.

Furthermore, the communication unit 5173 transmits the control signal for controlling the driving of the camera head 5119 to the camera head 5119. The control signal may also be transmitted by the optical communication.

The image processing unit 5157 performs various image processing on the image signal that is the RAW data transmitted from the camera head 5119. The image processing includes, for example, various known signal processing such as the development processing, the image quality enhancement processing (band enhancement processing, super-resolution processing, NR (Noise reduction) processing, and/or the camera shake correction processing), and/or the enlargement processing (electronic zooming processing). Furthermore, the image processing unit 5175 performs the detection processing on the image signal for performing the AE, the AF, and the AWB.

The image processing unit 5175 is configured by the processor such as the CPU and the GPU, and when the processor operates in accordance with the predetermined program, the above-described image processing or the detection processing can be performed. When the image processing unit 5175 is configured by the plurality of GPUs, the image processing unit 5175 divides information about the image signal as appropriate, and performs the image processing in parallel by the plurality of GPUs.

The control unit 5177 performs various controls relating to capturing the image of the surgery part by the endoscope 5115 and display of the captured image. For example, the control unit 5177 generates the control signal for controlling the driving of the camera head 5119. At this time, when the capturing conditions are input by the user, the control unit 5177 generates the control signal based on the input by the user. Alternatively, when the endoscope 5115 has the AE function, the AF function, and the AWB function, the control unit 5177 appropriately calculates an optimal exposure value, a focal length, and a white balance in accordance with a result of the detection processing by the image processing unit 5175, and generates the control signal.

Furthermore, the control unit 5177 displays the image of the surgery part on the display device 5155 based on the image signal that is subjected to the image processing by the image processing unit 5175. At this time, the control unit 5177 recognizes various objects in an image of the surgery part using various image recognition techniques. For example, by detecting the shape, the color, and the like of each edge of the objects included in the image of the surgery part, the control unit 5177 can recognize an operative tool such as the forceps, the specific biological site, the hemorrhage, the mist when the energy treatment tool 5135 is used, and the like. When displaying the image of the surgery part on the display device 5155, the control unit 5177 superimposes and displays various types of surgery support information about the image of the surgery part using a recognition result. By superimposing and displaying the operation support information and presenting it to the surgeon 5181, it is possible to proceed with the surgery more safely and reliably.

The transmission cable 5179 for connecting the camera head 5119 and the CCU 5153 is the electric signal cable corresponding to the communication by the electric signal, the optical fiber corresponding to the optical communication, or the composite cable thereof.

Here, in the example shown, the communication is made wirelessly using the transmission cable 5179, but the communication between the camera head 5119 and the CCU 5153 may be performed wirelessly. When the communication between the two is performed wirelessly, it is not necessary to lay the transmission cable 5179 in the surgery room, so that a situation in which movements of medical staffs in the surgery room is obstructed by the transmission cable 5179 can be eliminated.

An example of the endoscopic surgery system 5100 to which the technology according to the present disclosure may be applied is described above. Note that, although the endoscopic surgery system 5100 is described as an example here, a system to which the technology according to the present disclosure can be applied is not limited to such an example. For example, the technology of the present disclosure may be applied to a test flexible endoscopic system or a microscope surgery system.

The technology according to the present disclosure is suitably applied to the endoscope 5115, the CCU 5153, the display device 50155, and the like among the configurations described above. For example, the image sensor mounted on the endoscope 5115 functions as the image sensor 11 described with reference to FIG. 1. The image processing unit 5175 of the CCU 5153 functions as the video processing unit 13 described with reference to FIG. 1. The display device 5155 is the display device 15 described with reference to FIG. 1. By applying the technology according to the present disclosure to the endoscope 5155, the CCU 5153, the display device 5155, and the like, the visibility of the peaking display displayed on the display device 5155 can be improved. As a result, the focus adjustment at the time of the surgery can be easily realized, and the safe and highly reliable surgery can be performed.

For example, the technology according to the present disclosure may be applied a microscope surgery system used for so-called microsurgery, which is performed while observing a fine region of the patient in an enlarged manner.

FIG. 24 is a diagram showing an example of a schematic configuration of a microscope surgery system 5300 to which the technology according to the present disclosure may be applied. Referring to FIG. 24, the microscope surgery system 5300 includes a microscope device 5301, a control device 5317, and a display device 5319. In the following description of the microscope surgery system 5300, a "user" means any medical staff using the microscopic surgery system 5300 such as the surgeon and an assistant.

The microscope device 5301 includes a microscope portion 5303 for magnifying an observation target (surgery part of patient), an arm portion 5309 supporting the microscope portion 5303 at a distal end, and a base portion 5315 supporting a base end of the arm portion 5309.

The microscope portion 5303 includes a cylindrical portion 5305 having a substantially cylindrical shape, an image capture unit (not shown) provided inside the cylindrical portion 5305, an operation unit 5307 provided in a partial region of an outer periphery of the cylindrical portion 5305. The microscope portion 5303 is an electron-image capture type microscope portion (so-called video type microscope portion) that captures an electronically captured image by the image capture unit.

An opening surface of a lower end of the cylindrical portion 5305 is provided with a cover glass for protecting the image capture unit inside. Light from the observation target (hereinafter, also referred to as observation light) passes through the cover glass, and enters the image capture unit inside of the cylindrical portion 5305. Incidentally, the inside of the cylindrical portion 5305 may be provided with the light source, for example, the LED (Light Emitting Diode) or the like. At the time of capturing the image, the light may be irradiated from the light source to the observation target via the cover glass.

The image capture unit includes the optical system for condensing the observation light, and the image capture element for receiving the observation light that is condensed by the optical system. The optical system is configured by combining a plurality of lenses including the zoom lens and the focus lens, the optical characteristics are adjusted so as to image the observation light on the light receiving surface of the image capture element. The image capture element generates a signal corresponding to the observation light, i.e. the image signal corresponding to the observation image by receiving and photoelectric converting the observation light. As the image capture element, for example, a device capable of taking the color image having the Bayer array is used. The image capture element may be a variety of known image capture elements such as the CMOS (Complementary Metal Oxide Semiconductor) image sensor and the CCD (Charge Coupled Device) image sensor. The image signal generated by the image capture element is transmitted as the RAW data to the controller 5317. Here, the transmission of the image signal may be preferably performed by the optical communication. This is because since the surgeon performs the surgery while observing the state of the affected part by the captured image in a surgery on-site, it is required that the moving image of the surgery part be displayed in real time as much as possible for safer and more reliable surgery. By transmitting the image signal with the optical communication, it becomes possible to display the captured image with low latency.

Incidentally, the image capture unit may have a driving mechanism for moving the zoom lens and the focus lens of the optical system along the optical axis. By appropriately moving the zoom lens and the focus lens with the driving mechanism, the magnification of the captured image and the focal length at the time of capturing the image can be adjusted. In addition, various functions that can be generally provided in an electronic image capture type microscope portion such as the AE (Auto Exposure) function and the AF (Auto Focus) function may be mounted on the image capture unit.

Furthermore, the image capture unit may be configured as a so-called single-plate image capture unit having a single image capture element, or may be configured as an image capture unit of the so-called multi-plate type having the plurality of image capture elements. In a case where the image capture unit is configured by the multi-plate type, for example, the image signal corresponding to each of R, G, and B may be generated by each image capture element, and the color image may be obtained by synthesizing the image signal. Alternatively, the image capture unit may be configured to have a pair of image capture elements for acquiring the image signals for the right eye and the left eye corresponding to the stereoscopic vision (3D display), respectively. By displaying 3D, the surgeon can more accurately grasp the depth of the living tissue in the surgery part. Incidentally, when the image capture unit is constituted by a multi-plate type, corresponding to each image capture element, a plurality of optical systems may also be provided.

The operation unit 5307 is constituted by, for example, a cross lever or a switch or the like, and is an input means for receiving the operation input of the user. For example, the user can input an instruction to change the magnification of the observation image and the focal length to the observation target via the operation unit 5307. The magnification and the focal length can be adjusted by appropriately moving the zoom lens and the focus lens by the driving mechanism of the image capture unit according to the instruction. Furthermore, for example, the user can input an instruction to switch an operation mode of the arm portion 5309 (all-free mode and fixed mode (described later)) via the operation unit 5307. When the user intends to move the microscope portion 5303, it is assumed that the user moves the microscope portion 5303 in a state where the user grips the cylindrical portion 5305. Therefore, the operation unit 5307 is preferably provided in a position where it is easily operated by fingers in a state that the user grips the cylindrical portion 5305 so that it is operable while moving the cylindrical portion 5305.

The arm portion 5309 is configured such that a plurality of links (first link 5313a to sixth link 5313f) are rotatably connected to each other by a plurality of joint portions (first joint portion 5311a to sixth joint portion 5311f).

The first joint portion 5311a has a substantially cylindrical shape, and supports an upper end of the cylindrical portion 5305 of the microscope portion 5303 rotatably around a rotation axis (first axis O1) parallel to the central axis of the cylindrical portion 5305 at the distal end (lower end) thereof. Here, the first joint portion 5311a may be configured such that the first axis O1 coincides with the optical axis of the image capture unit of the microscope portion 5303. Thus, by rotating the microscope portion 5303 around the first axis O1, it is possible to change the field of view so as to rotate the captured image.

The first link 5313a fixedly supports the first joint portion 5311a at the distal end. Specifically, the first link 5313a is a rod-shaped member having a substantially L-shaped shape, and is connected to the first joint portion 5311a such that one side on a distal end side thereof extends in a direction orthogonal to the first axis O1 and an end portion of the one side abuts an upper end portion of an outer periphery of the first joint portion 5311a. The second joint portion 5311b is connected to the end of the other side of the first link 5313a on a substantially L-shaped base end side.

The second joint portion 5311b has a substantially cylindrical shape, and supports a base end of the first link 5313a rotatably around a rotation axis (second axis O2) orthogonal to the first axis O1 at the distal end thereof. A distal end of the second link 5313b is fixedly connected to a base end of the second joint portion 5311b.

The second link 5313b is a rod-shaped member having a substantially L-shaped shape, and an end portion of the one side thereof is fixedly connected to the base end of the second joint portion 5311b while one side on a distal end side thereof extends in a direction orthogonal to the second axis O2. The third joint portion 5311c is connected to the other side of the second link 5313b on the substantially L-shaped base end side.

The third joint portion 5311c has a substantially cylindrical shape, and supports the base end of the second link 5313b rotatably around a rotation axis O3 orthogonal to the first axis O1 and the second axis O2 at the distal end thereof. A distal end of the third link 5313c is fixedly connected to a base end of the third joint portion 5311c. By rotating the configuration on the distal end side including the microscope portion 5303 around the second axis O2 and the third axis O3, the microscope portion 5303 can be moved so as to change the position of the microscope portion 5303 in the horizontal plane. That is, by controlling the rotation around the second axis O2 and the third axis O3, it is possible to move the field of view of the captured image in a plane.

The third link 5313c is configured to have a substantially cylindrical shape on its distal end side, and is fixedly connected to a cylindrical shape distal end such that the base end of the third joint portion 5311c has substantially the same central axis. The base end side of the third link 5313c has a prism shape, and the fourth joint portion 5311d is connected to the end portion thereof.

The fourth joint portion 5311d has a substantially cylindrical shape, and supports the base end of the third link 5313c rotatably around a rotation axis (fourth axis O4) orthogonal to the third axis O3 at the distal end thereof.

The fourth link 5313d is a rod-shaped member extending substantially linearly, and is fixedly connected to the fourth joint portion 5311d so that the end portion of the distal end thereof abuts on a substantially cylindrical side surface of the fourth joint portion 5311d while extending orthogonal to the fourth axis O4. The fifth joint portion 5311e is connected to a base end of the fourth link 5313d.

The fifth joint portion 5311e has a substantially cylindrical shape, and supports the base end of the fourth link 5313d rotatably around a rotation axis (fifth axis O5) parallel to the fourth axis O4 on a distal end side thereof. A distal end of the fifth link 5313e is fixedly connected to a base end of the fifth joint portion 5311e. The fourth axis O4 and the fifth axis O5 are rotation axes that can move the microscope portion 5303 in the vertical direction. The height of the microscope portion 5303, that is, the distance between the microscope portion 5303 and the observation target can be adjusted by rotating a distal-end-side configuration including the microscope portion 5303 around the fourth axis O4 and the fifth axis O5.

The fifth link 5313e is configured by combining a first member having a substantially L-shape extending in the vertical direction on one side and extending in the horizontal direction on the other side, and a second member having a rod shape extending in the vertical downward direction from a portion extending in the horizontal direction of the first member. The base end of the fifth joint site 5311e is fixedly connected to a vicinity of an upper end of a portion extending in the vertical direction of the first member of the fifth link 5313e. The sixth joint portion 5311f is connected to the base end (lower end) of the second member of the fifth link 5313e.

The sixth joint portion 5311f has a substantially cylindrical shape, and supports a base end of the fifth link 5313e rotatably around a rotation axis (sixth axis O6) parallel to the vertical direction on a distal end side thereof. A distal end of the sixth link 5313f is fixedly connected to a base end of the sixth joint portion 5311f.

The sixth link 5313f is a rod-shaped member extending in the vertical direction, and its base end is fixedly connected to an upper surface of the base portion 5315.

Rotatable ranges of the first joint portion 5311a to the sixth joint portion 5311f are appropriately set so that the microscope portion 5303 can perform a desired movement. As a result, in the arm portion 5309 having the above-described configuration, a total of six degrees of freedom of movement including three translational degrees of freedom and three rotational degrees of freedom can be realized with respect to the movement of the microscope portion 5303. Thus, by configuring the arm portion 5309 so that six degrees of freedom with respect to the movement of the microscope portion 5303 is realized, it is possible to freely control a position and a posture of the microscope portion 5303 within a movable range of the arm portion 5309. Therefore, it is possible to observe the surgery part from all angles, and it is possible to perform the surgery more smoothly.

Note that the configuration of the arm portion 5309 shown in the drawing is merely an example, and the number and shape (length) of the links constituting the arm portion 5309, the number of joint portions, the arrangement position, the direction of the rotation axis, and the like may be appropriately designed so that a desired degree of freedom can be realized. For example, as described above, in order to freely move the microscope portion 5303, the arm portion 5309 is preferably configured to have six degrees of freedom, but the arm portion 5309 may be configured to have a greater degree of freedom, (i.e., redundant degrees of freedom). When the redundant degree of freedom is present, the arm portion 5309, in a state where the position and the posture of the microscope portion 5303 is fixed, it is possible to change a posture of the arm portion 5309. Therefore, for example, the posture of the arm portion 5309 can be controlled so that the arm portion 5309 does not interfere with the field of view of the surgeon viewing the display device 5319, thereby realizing control with high convenience for the surgeon.

Here, the first joint portion 5311a to the sixth joint portion 5311f may be provided with an actuator on which the driving mechanism such as a motor, an encoder for detecting a rotation angle at each joint portion, and the like are mounted. The control device 5317 appropriately controls the driving of the actuators provided in the first joint portion 5311a to the sixth joint portion 5311f, whereby the posture of the arm portion 5309, that is, the position and the posture of the microscope portion 5303 can be controlled. Specifically, the control device 5317 can grasp a current posture of the arm portion 5309 and a current position and posture of the microscope portion 5303 based on the information about the rotation angle of each joint portion detected by the encoder. The control device 5317 uses the grasped information to calculate a control value (e.g., rotation angle or generated torque, or the like) for each joint portion such as to realize the movement of the microscope portion 5303 in response to the operation input from the user, and to drive the driving mechanism of each joint portion in accordance with the control value. In this case, a control method of the arm portion 5309 by the control device 5317 is not limited, and various known control methods such as the force control or the position control may be applied.

For example, the surgeon performs an appropriate operation input via an input device (not shown), whereby driving of the arm portion 5309 may be appropriately controlled by the control device 5317 in response to the operation input, and the position and the posture of the microscope portion 5303 may be controlled. By the control, the microscope portion 5303 can be moved from an arbitrary position to an arbitrary position, and then fixedly supported at the position after the movement. As the input device, for example, a foot switch or the like, which can be operated even if the surgeon has the surgical tools in his/her hand, is preferably used in consideration of convenience of the surgeon. In addition, an operation input may be performed without contact based on gesture detection or line-of-sight detection using a wearable device or a camera provided in the surgery room. As a result, even a user belonging to a clean area can operate the devices belonging to a non-clean area with a higher degree of freedom. Alternatively, the arm portion 5309 may be operated by a so-called master-slave method. In this case, the arm portion 5309 can be remotely operated by the user via an input device installed at a location remote from the surgery room.

If the force control is applied, so-called power assist control may be performed in which the actuators of the first joint portion 5311a to the sixth joint portion 5311f are driven to receive an external force from the user and move the arm portion 5309 smoothly in accordance with the external force. As a result, when the user tries to directly move the position by holding the microscope portion 5303, the microscope portion 5303 can be moved with a relatively light force. Therefore, it is possible to move the microscope portion 5303 more intuitively and with a simpler operation, and the convenience of the user can be improved.

The driving of the arm portion 5309 may be controlled so as to perform a pivot operation. Here, the pivot operation is an operation of moving the microscope portion 5303 so that the optical axis of the microscope portion 5303 always faces a predetermined point (hereinafter referred to as pivot point) in a space. According to the pivot operation, since the same observation position can be observed from various directions, it is possible to observe the affected part in more detail. When the microscope portion 5303 is configured so as not to be able to adjust the focal length, it is preferable that the pivot operation is performed in a state where the distance between the microscope portion 5303 and the pivot point is fixed. In this case, the distance between the microscope portion 5303 and the pivot point may be adjusted to a fixed focal length of the microscope portion 5303. Thus, the microscope portion 5303 will move on a hemispherical surface (shown schematically in FIG. 24) having a radius corresponding to the focal length around the pivot point, so that a clear captured image can be obtained even if changing the observation direction. On the other hand, when the microscope portion 5303 is configured such that the focal length is adjustable, the pivot operation may be performed in a state where the distance between the microscope portion 5303 and the pivot point is variable. In this case, for example, the control device 5317 may calculate the distance between the microscope portion 5303 and the pivot point based on the information about the rotation angle of each joint portion detected by the encoder, and automatically adjust the focal length of the microscope portion 5303 based on the calculation result. Alternatively, if the AF function is provided in the microscope portion 5303, each time the distance between the microscope portion 5303 and the pivot point is changed by the pivot operation, the focal length may be automatically adjusted by the AF function.

The first joint portion 5311a to the sixth joint portion 5311f may be provided with brakes for restraining rotation thereof. Operations of the brakes can be controlled by the controller 5317. For example, if it is desired to fix the position and the posture of the microscope portion 5303, the control device 5317 operates the brakes of the respective joint portions. Thus, the posture of the arm portion 5309, i.e. since the position and the posture of the microscope portion 5303 can be fixed without driving the actuators, it is possible to reduce a power consumption. If it is desired to move the position and the posture of the microscope portion 5303, the control device 5317 releases the brake of each joint portion, it is sufficient to drive the actuator according to a predetermined control method.

Such operations of the brakes can be performed in response to the operation input by the user via the operation unit 5307 described above. When the user wants to move the position and the posture of the microscope portion 5303, the user operates the operation unit 5307 to release the brakes of the respective joint portions. Thus, the operation mode of the arm portion 5309 is shifted to a mode (all-free mode) capable of freely performing rotation in each joint portion. When the user wants to fix the position and the posture of the microscope portion 5303, the user operates the operation unit 5307 to operate the brakes of the respective joint portions. As a result, the operation mode of the arm portion 5309 shifts to a mode in which the rotation of each joint portion is restrained.

The control device 5317 controls the operations of the microscope apparatus 5301 and the display device 5319, thereby controlling the overall operation of the microscope surgery system 5300. For example, the control device 5317 controls the driving of the arm portion 5309 by operating the actuators of the first joint portion 5311a to the sixth joint portion 5311f in accordance with a predetermined control scheme. Furthermore, for example, the control device 5317 controls the operation of the brakes of the first joint portion 5311a to the sixth joint portion 5311f, to thereby change the operation mode of the arm portion 5309. Furthermore, for example, the control device 5317 performs various signal processing to the image signal acquired by the image capture unit of the microscope portion 5303 of the microscope apparatus 5301, to thereby generating image data for display as well as displaying the image data on the display device 5319. In the signal processing, various well-known signal processing may be performed, for example, the development processing (demosaicing processing), the image quality enhancement processing (band enhancement processing, super-resolution processing, NR (Noise reduction) processing, and/or camera shake correction processing), and/or enlargement processing (i.e., electronic zooming processing).

Incidentally, the communication between the control device 5317 and the microscope portion 5303 and the communication between the control device 5317 and the first to sixth joint portions 5311a to 5311f may be wired communication or wireless communication. In the case of the wired communication, the communication by the electric signal or the optical communication may be performed. In this case, the cable for transmission used in the wired communication may be configured as the electrical signal cable, the optical fiber, or the composite cable thereof depending on the communication method. On the other hand, in the case of the wireless communication, since it is not necessary to lay the transmission cable in the surgery room, it is possible to eliminate a situation in which the movement of the medical staffs in the surgery room is obstructed by the transmission cable.

The controller 5317 may be a processor such as the CPU (Central Processing Unit), the GPU (Graphics Processing Unit), or the like, or a microcomputer or a control board on which the processor and storage elements such as a memory are mixed and loaded. When the processor of the control device 5317 operates in accordance with the predetermined program, the above-described various functions can be realized. In the example shown, the control device 5317 is provided as a device separate from the microscope device 5301, but the control device 5317 may be provided inside the base portion 5315 of the microscope device 5301 and configured integrally with the microscope device 5301. Alternatively, the control device 5317 may be configured by a plurality of devices. For example, the microcomputer, the control board, or the like may be arranged in each of the microscope portion 5303 and the first joint portion 5311a to the sixth joint portion 5311f of the arm portion 5309, and these may be connected to each other so as to be able to communicate with each other, whereby the same function as that of the control device 5317 may be realized.

The display device 5319 is provided in the surgery room and displays an image corresponding to the image data generated by the control device 5317 under control from the control device 5317. In other words, the display device 5319 displays an image of the surgery part captured by the microscope portion 5303. Note that the display device 5319 may display various types of information about the surgery such as the body information of the patient, information about the surgical procedure, and the like, instead of the image of the surgery part or together with the image of the surgery part. In this case, the display of the display device 5319 may be appropriately switched by the operation by the user. Alternatively, a plurality of display devices 5319 may be provided, and each of the plurality of display devices 5319 may display the image of the surgery part and various types of information about the surgery. As the display device 5319, such as the liquid crystal display device or the EL (Electro Luminescence) display device, various known display devices may be applied.

FIG. 25 is a diagram showing the surgery using the microscope surgery system 5300 shown in FIG. 24. In FIG. 25, an surgeon 5321 is schematically shown performing surgery on a patient 5325 on a patient bed 5323 using a microscope surgery system 5300. In FIG. 25, for simplicity, the control device 5317 is omitted from the configuration of the microscope surgery system 5300, and the microscope device 5301 is shown in a simplified manner.

As shown in FIG. 25, at the time of the surgery, the image of the surgery part captured by the microscope device 5301 is enlarged and displayed on the display device 5319 installed on the wall surface of the surgery room by using the microscope surgery system 5300. The display device 5319 is installed at a position facing the surgeon 5321, and the surgeon 5321 performs various types of treatment on the surgery part, such as resection of the affected part, while observing the state of the surgery part by the image projected on the display device 5319.

As described above, an example of the microscope surgery system 5300 to which the technology according to the present disclosure can be applied is described. Note that, although the microscope surgery system 5300 is described as an example here, a system to which the technology according to the present disclosure can be applied is not limited to such an example. For example, the microscope device 5301 may also function as a support arm device that supports other observation devices and other surgical tools instead of the microscope portion 5303 at its distal end. As the other observation apparatus, for example, an endoscope may be applied. As the other surgical tool, the forceps, the tweezer, the pneumoperitoneum tube for pneumoperitoneum, the energy treatment tool for incising tissues or sealing blood vessels by cauterization, or the like can be applied. By supporting the observation apparatus and the surgical tools by the support arm apparatus, it is possible to fix the position more stably than when the medical staff manually supports the observation apparatus and the surgical tools, and it is possible to reduce the burden on the medical staff. The technology according to the present disclosure may be applied to a support arm device supporting a configuration other than such a microscope portion.

The technology according to the present disclosure is suitably applied to the microscope portion 5303, the control device 5317, the display device 5319, and the like among the above-described configurations. For example, the image sensor mounted on the microscope portion 5303 functions as the image sensor 11 described with reference to FIG. 11. The control device 5317 functions as the video processing unit 13 described with reference to FIG. 1. The display device 5319 is the display device 15 described with reference to FIG. 1. By applying the technology according to the present disclosure to the microscope portion 5303, the control device 5317, the display device 5319, and the like, the visibility of the peaking display displayed on the display device 5319 can be improved. As a result, the focus adjustment at the time of the surgery can be easily realized, and the safe and highly reliable surgery can be performed.

At least two of the features of the present technology described above can also be combined. In other words, various features described in the respective embodiments may be combined discretionarily without distinguishing among the embodiments. Furthermore, the various effects described above are not limitative but are merely illustrative, and other effects may be provided.

In the present disclosure, "same", "equal", "orthogonal", and the like are concepts including "substantially same", "substantially equal", "substantially orthogonal", and the like. For example, the states included in a predetermined range (e.g., within range of ±10%) with reference to "completely same", "completely equal", "completely orthogonal", and the like are also included.

(1) An image capture apparatus, including:
an image generation unit that generates a captured image by capturing a subject;
an edge detection unit that detects an edge portion included in the generated captured image; and
a color control unit that controls a color of a highlighted display for highlighting the edge portion for each detected edge portion based on color information about the edge portion in the captured image.

(2) The image capture apparatus according to (1), in which
the color control unit controls the color of the highlighted display so that a color difference between an edge color represented by the color information about the edge portion and the color of the highlighted display becomes large.

(3) The image capture apparatus according to (2), in which
the color control unit controls the color of the highlighted display so that the edge color and the color of the highlighted display are colors far in a hue plane or a brightness direction.

(4) The image capture apparatus according to (2) or (3), in which
the color control unit sets the color of the highlighted display from a plurality of color candidates.

(5) The image capture apparatus according to (4), in which
the plurality of color candidates includes chromatic color candidates, and
the color control unit sets a color candidate having a hue farthest from the hue of the edge color among the plurality of color candidates as the color of the highlighted display.

(6) The image capture apparatus according to (5), in which
the plurality of color candidates includes a first color candidate and a second color candidate having a different hue from the first color candidate.

(7) The image capture apparatus according to (6), in which
the first and second color candidates are set to be complementary colors to each other.

(8) The image capture apparatus according to any one of (4) to (7), in which
the plurality of color candidates includes achromatic color candidates, and
the color control unit sets a color candidate having brightness farthest from brightness of the edge color among the plurality of color candidates as the color of the highlighted display.

(9) The image capture apparatus according to (8), in which
the plurality of color candidates includes black and white, and
the color control unit sets the color of the highlighted display to black when the brightness of the edge color is larger than a predetermined threshold, and sets the color of the highlighted display to white color when the brightness of the edge color is smaller than the predetermined threshold.

(10) The image capture apparatus according to any one of (4) to (9), wherein
the plurality of color candidates is set by a user.

(11) The image capture apparatus according to any one of (4) to (10), in which
the plurality of color candidates is set according to the subject.

(12) The image capture apparatus according to any one of (2) to (11), in which
the edge detection unit detects a pixel position of the edge portion, and
the color control unit sets the color of the highlighted display for each of the detected pixel positions.

(13) The image capture apparatus according to (12), in which
the color information about the edge portion includes pixel information of a reference pixel included in a predetermined pixel region surrounding the pixel position of the edge portion, and
the color control unit calculates the hue of the edge color or the brightness of the edge color based on the pixel information of the reference pixel.

(14) The image capture apparatus according to (13), in which
the color control unit calculates an average hue of the reference pixel as the hue of the edge color.
(15) The image capture apparatus according to (13) or (14), in which
the predetermined pixel region is set according to the subject.
(16) The image capture apparatus according to any one of (1) to (15), in which
the color control unit generates a peaking image in which the edge portion of the captured image is highlighted by the color of the highlighted display.
(17) The image capture apparatus according to (16), in which
in the peaking image, a color of a portion different from the edge portion is set to the same color as that of the original image.
(18) The image capture apparatus according to (16) or (17), in which
the color control unit controls the color of the highlighting so that the display of the edge portion of the peaking image changes dynamically.
(19) An image capture method executed by a computer system, comprising:
generating a captured image in which an image of a subject is captured;
detecting an edge portion included in the generated captured image; and
controlling a color of a highlighted display for highlighting the edge portion for each detected edge portion based on color information about the edge portion in the captured image.
(20) A program that causes a computer system to execute the following steps of:
generating a captured image in which an image of a subject is captured;
detecting an edge portion included in the generated captured image; and
controlling a color of a highlighted display for highlighting the edge portion for each detected edge portion based on color information about the edge portion in the captured image.

REFERENCE SIGNS LIST 1 subject
11 image sensor
13 video processing unit
25 original image
30 camera signal processing unit
31 peaking detection unit
32 superimposing color setting unit
33 superimposing color selecting unit
34 synthesizing unit
40, 240 peaking image
41 edge portion
42, 42a, 42b highlighted display
43 color candidate
43a first color candidate
43b second color candidate
44, 44a, 44b edge color
47 reference pixel
51 predetermined pixel region
100 image capture apparatus

The invention claimed is:
1. An image capture apparatus, comprising:
a central processing unit (CPU) configured to:
generate a captured image by capture of a subject;
detect an edge portion in the generated captured image;
detect a pixel position of the edge portion;
acquire pixel information of a reference pixel in a pixel region surrounding the pixel position of the edge portion;
determine one of a hue of an edge color of the edge portion or a brightness of the edge color based on the pixel information of the reference pixel; and
control a color of a highlighted display to highlight the detected pixel position of the edge portion, wherein the color of the highlighted display for the edge portion is controlled based on the determined one of the hue or the brightness of the edge color of the edge portion in the captured image.
2. The image capture apparatus according to claim 1, wherein the CPU is further configured to control the color of the highlighted display to increase a color difference between the edge color of the edge portion and the color of the highlighted display.
3. The image capture apparatus according to claim 2, wherein the CPU is further configured to control the color of the highlighted display so that the edge color is far from the color of the highlighted display colors far in a hue plane or a brightness direction.
4. The image capture apparatus according to claim 2, wherein the CPU is further configured to set the color of the highlighted display from a plurality of color candidates.
5. The image capture apparatus according to claim 4, wherein
the plurality of color candidates includes a plurality of chromatic color candidates, and
the CPU is further configured to set, as the color of the highlighted display, a color candidate having a hue farthest from the hue of the edge color in a hue plane among the plurality of color candidates.
6. The image capture apparatus according to claim 5, wherein
the plurality of color candidates includes a first color candidate and a second color candidate, and
the second color candidate has hue different from that of the first color candidate.
7. The image capture apparatus according to claim 6, wherein the first color candidate is complementary to the second color candidate.
8. The image capture apparatus according to claim 4, wherein
the plurality of color candidates includes a plurality of achromatic color candidates, and
the CPU is further configured to set, as the color of the highlighted display, a color candidate having brightness farthest from the brightness of the edge color in a brightness direction among the plurality of color candidates.
9. The image capture apparatus according to claim 8, wherein
the plurality of color candidates includes black and white, and
the CPU is further configured to set the color of the highlighted display to black in a case where the brightness of the edge color is larger than a threshold; and
set the color of the highlighted display to white in a case where the brightness of the edge color is smaller than the threshold.

10. The image capture apparatus according to claim 4, wherein the CPU is further configured to set a plurality of color candidates based on a user operation.

11. The image capture apparatus according to claim 4, wherein the CPU is further configured to set the plurality of color candidates based on the subject.

12. The image capture apparatus according to claim 2, wherein the CPU is further configured to:
   detect a plurality of pixel positions of the edge portion, wherein the plurality of pixel positions includes the pixel position of the edge portion; and
   set the color of the highlighted display for each pixel position of the detected plurality of pixel positions.

13. The image capture apparatus according to claim 12, wherein the CPU is further configured to calculate an average hue of the reference pixel as the hue of the edge color.

14. The image capture apparatus according to claim 12, wherein the CPU is further configured to set the pixel region based on the subject.

15. The image capture apparatus according to claim 1, wherein the CPU is further configured to generate a peaking image in which the edge portion of the captured image is highlighted by the color of the highlighted display.

16. The image capture apparatus according to claim 15, wherein the CPU is further configured to set a color of a portion, in the peaking image, different from the edge portion to the same color as that of the captured image.

17. The image capture apparatus according to claim 15, wherein the CPU is further configured to control the color of the highlighted display such that a display of the edge portion of the peaking image changes dynamically.

18. An image capture method, comprising:
   generating a captured image by capturing a subject;
   detecting an edge portion in the generated captured image;
   detecting a pixel position of the edge portion;
   acquiring pixel information of a reference pixel in a pixel region surrounding the pixel position of the edge portion;
   determining one of a hue of an edge color of the edge portion or a brightness of the edge color based on the pixel information of the reference pixel; and
   controlling a color of a highlighted display for highlighting the detected pixel position of the edge portion, wherein the color of the highlighted display for the edge portion is controlled based on the determined one of the hue or the brightness of the edge color of the edge portion in the captured image.

19. A non-transitory computer-readable medium having stored thereon, computer-executable instructions which, when executed by a computer, cause the computer to execute operations, the operations comprising:
   generating a captured image by capturing a subject;
   detecting an edge portion in the generated captured image;
   detecting a pixel position of the edge portion;
   acquiring pixel information of a reference pixel in a pixel region surrounding the pixel position of the edge portion;
   determining one of a hue of an edge color of the edge portion or a brightness of the edge color based on the pixel information of the reference pixel; and
   controlling a color of a highlighted display for highlighting the detected pixel position of the edge portion, wherein the color of the highlighted display for the edge portion is controlled based on the determined one of the hue or the brightness of the edge color of about the edge portion in the captured image.

20. An image capture apparatus, comprising:
   a central processing unit (CPU) configured to:
   generate a captured image by capture of a subject;
   detect an edge portion in the generated captured image;
   detect a pixel position of the edge portion;
   calculate an average hue of a reference pixel as a hue of an edge color of the edge portion based on the detected pixel position, wherein the reference pixel is in a pixel region surrounding the pixel position of the edge portion; and
   control a color of a highlighted display to highlight the detected pixel position of the edge portion, wherein
      the color of the highlighted display for the edge portion is controlled based on the calculated average hue of the reference pixel, and
      the color of the highlighted display is controlled to increase a color difference between the edge color of the edge portion and the color of the highlighted display.

* * * * *